(12) United States Patent
    Bakaletz et al.

(10) Patent No.: US 8,236,494 B2
(45) Date of Patent: Aug. 7, 2012

(54) **GENES OF AN OTITIS MEDIA ISOLATE OF NONTYPEABLE *HAEMOPHILUS INFLUENZAE***

(75) Inventors: Lauren O. Bakaletz, Hilliard, OH (US); Robert S. Munson, Jr., Columbus, OH (US); David W. Dyer, Oklahoma City, OK (US)

(73) Assignee: Nationwide Children's Hospital, Inc., Columbus, OH (US)

( * ) Notice: Subject to any disclaimer, the term of this patent is extended or adjusted under 35 U.S.C. 154(b) by 0 days.

(21) Appl. No.: 13/187,989

(22) Filed: Jul. 21, 2011

(65) Prior Publication Data
US 2011/0293624 A1    Dec. 1, 2011

Related U.S. Application Data

(60) Division of application No. 12/860,332, filed on Aug. 20, 2010, now Pat. No. 7,998,490, which is a continuation of application No. 12/646,424, filed on Dec. 23, 2009, now Pat. No. 7,816,086, which is a continuation of application No. 11/770,447, filed on Jun. 28, 2007, now Pat. No. 7,638,282, which is a continuation of application No. 10/795,159, filed on Mar. 5, 2004, now Pat. No. 7,241,867.

(60) Provisional application No. 60/453,134, filed on Mar. 6, 2003.

(51) Int. Cl.
    *C12Q 1/08* (2006.01)
(52) U.S. Cl. ...... 435/6; 435/252.3; 435/320.1; 536/23.7
(58) Field of Classification Search ........................ None
    See application file for complete search history.

(56) References Cited

U.S. PATENT DOCUMENTS 6,797,273 B1    9/2004    Ruelle et al.

FOREIGN PATENT DOCUMENTS

| WO | WO-93/07273 A1 | 4/1993 |
| WO | WO-99/24758 | 5/1999 |
| WO | WO-02/34768 | 5/2002 |

OTHER PUBLICATIONS

Ackerley et al., A genome-scale analysis for identification of genes required for growth or survival of *Haemophilus influenzae*, Proc. Natl. Acad. Sci., 99(2): 966-71 (2002).
Altschul et al., Basic local alignment search tool, *J. Mol. Biol.*, 215: 403-10 (1990).
Anderson et al., Quantitative filter hybridisation, Chapter 4, 73-111, Nucleic Acid Hybridisation: A Practical Approach, IRL Press Limited, Oxford, England, 2002.
Anderson et al., Human serum activities against *Hemophilus influenzae*, Type B, *J. Clin. Invest.*, 51: 31-8 (1972).
Badger et al., Identification of *Escherichia coli* K1 genes contributing to human brain microvascular endothelial cell invasion by differential fluorescence induction, *Molec. Microbiol.*, 36(1): 174-82 (2000).
Bakaletz et al., Evidence for transdutation of specific antibody into the middle ears of parenterally immunized chinchillas after an upper respiratory tract infection with adenovirus, *Clin. Diagnos. Lab. Immunol.*, 4(2):223-5 (1997).
Bakaletz et al., Frequency of fimbriation of nontypable *Haemophilus influenzae* and its ability to adhere to chinchilla and human respiratory epithelium, *Infect. Immun.*, 56(2):331-5 (1998).
Bakaletz et al., Modeling adenovirus type-1 induced otitis media in the chinchilla: Effect on ciliary activity and fluid transport function of eustachian tube mucosal epithelium, *J. Infect. Dis.*, 186:865-72 (1993).
Bakaletz et al., Protection against development of otitis media induced by nontypeable *Haemophilus influenzae* by both active and passive immunization in a chinchilla model of virus-bacterium superinfection, *Infect. Immun.*, 67(6):2746-62 (1999).
Bakaletz et al., Relative immunogenicity and efficacy of two synthetic chimeric peptides of fimbrin as vaccinogens against nasopharyngeal colonization by nontypeable *Haemophilus influenzae* in the chinchilla, *Vaccine*, 15(9):955-61 (1997).
Baldwin, Effects of otitis media on child development, *Am. J. Otol.* 14(2):601-4 (1993).
Baltes et al., *Actinobacillus pleuropneumoniae* iron transport and urease activity: Effects on bacterial virulence and host immune response, *Infect. Immun.*, 69(1):472-8 (2001).
Barenkamp et al., Outer membrane protein and biotype analysis of pathogenic nontypable *Haemophilus influenzae*, *Infect. Immun.*, 36(2):535-40 (1982).
Bartilson et al., Differential fluorescence induction reveals *Streptococcus pneumoniae* loci regulated by competence stimulatory peptide, *Molec. Microbiol.*, 39(1):126-35 (2001).
Berman et al., Theoretical cost effectiveness of management options for children with persisting middle ear effusions, *Pediatrics*, 83(3): (1984).
Black et al., Efficacy, safety and immunogenicity of heptavalent pneumococcal conjugate vaccine in children, *Pediatr. Infect. Dis. J.*, 19:187-95 (2000).
Bosse et al., Urease activity may contribute to the ability of *Actinobacillus pleuropneumoniae* to establish infection, *Can. J. Vet. Res.*, 64:145-50 (2000).
Bright et al., The prevalence of tympanostomy tubes in children in the United States, 1988, *Am. J. Pub. Health*, 83(7): (1993).
Cardillo et al., Synthesis of the phenylserine-leucine dipeptide fragment present in the antibiotic lysobactin from an aziridine-2-imide precursor, *Eur. J. Org. Chem.*, 2489-94 (2000).
Chiang et al., In vivo genetic analysis of bacterial virulence, *Annu. Rev. Microbiol.*, 53: 129-54 (1999).
Chissoe et al., Strategies for rapid and accurate DNA sequencing, *Methods*, 3(1):55-65 (1991).
Cimons, Watchful waiting advised when treating otitis media, *ASM News*, 60(10): 527-8 (1994).
Cormack et al., FACS-optimized mutants of the green fluorescent protein (GFP), *Gene*, 173:33-8 (1996).

(Continued)

*Primary Examiner* — Jennifer Graser
(74) *Attorney, Agent, or Firm* — Marshall, Gerstein & Borun LLP

(57) ABSTRACT

The invention relates to the polynucleotide sequence of a nontypeable stain of *Haemophilus influenzae* (NTHi) and polypeptides encoded by the polynucleotides and uses thereof. The invention also relates to NTHi genes which are upregulated during or in response to NTHi infection of the middle ear and/or the nasopharynx.

8 Claims, 15 Drawing Sheets

OTHER PUBLICATIONS

Davis et al., Liposomes as adjuvants with immunopurified tetanus toxoid: the immune response, *Immunol. Lett.*, 14:341-8 (1986/1987).
Demaria et al., Biotypes of serologically nontypable *Haemophilus influenzae* isolated from the middle ears and nasopharynges of patients with otitis media with effusion, *J. Clin. Microbiol.*, 20(6):1102-4 (1984).
Demaria et al., Immunization with outer membrane protein P6 from nontypeable *Haemophilus influenzae* induces bactericidal antibody and affords protection in the chinchilla model of otitis media, *Infect. Immun.*, 64(12):5187-92 (1996).
Devereux et al., A comprehensive set of sequence analysis programs for the VAX, *Nucl. Acid Res.*, 12(1):387-95 (1984).
Dhandayuthapani et al., Green fluorescent protein as a marker for gene expression and cell biology of mycobacterial interactions with macrophages, *Molec. Microbiol.*, 17(5):901-12 (1995).
Dunn et al., A vector for promoter trapping in *Bacillus cereus*, *Gene*, 226:297-305 (1999).
Ehrlich et al., Mucosal biofilm formation on middle-ear mucosa in the chinchilla model of otitis media, *JAMA*, 287(13):1710-5 (2002).
Erickson et al., Chapter 3: Solid-phase peptide synthesis in the proteins, v.2, Academic Press, New York: 255-527, 2002.
Eskola et al., Efficacy of a pneumococcal conjugate vaccine against acute otitis media, *N. Engl. J. Med.*, 344(6):403-9 (2001).
Eskola et al., Potential of bacterial vaccines in the prevention fo acute otitis media, *Pediatr. Infect. Dis. J.*, 19 (5):72-8 (2000).
Eskra et al., *Brucella abortus* genes identified following constitutive growth and macrophage infection, *Infect. Immun.*, 69(12):7736-7742 (2001).
Fleischmann et al., *Haemophilus influenza* Rd KW20 section 45 of 163 of the complete genome. EMBL: H132730, Database accession No. U32730, L42023 (1995).
Fleischmann et al., Histidine biosynthesis bifunctional protein hisB. UNIPROT: HIS7_HAEIN, Database asscession No. P44327 (1995).
Fleischmann et al., Whole-genome random sequencing and assembly of *Haemophilus influenza* Rd. *Science*, 269: 496-512 (1995).
Giebank, Immunology: Promise of new vaccines, *Pediatr. Infect. Dis. J.*, 13(11):1064-8 (1994).
Goosen et al., The regulation of transcription initiation by integration host factor, *Molec. Microbiol.*, 16(1):1-7 (1995).
Green et al., Certain-site directed, nonenzymatically active mutants of the *Haemophilus influenzae* P4 lipoprotein are able to elicit bactericidal antibodies, *Infect. Immun.*, 73:4454-7 (2005).
Gritsun et al., Analysis of flavivirus envelope proteins reveals variable domains that reflect their antigenicity and may determine their pathogenesis, *Virus Res.*, 35:307-21 (1995).
Holmes et al., Adherence of non-typeable *Haemophilus influenzae* promotes reorganization of the actin cytoskeleton in human or chinchilla epithelial cells in vitro, *Microbial Pathogenesis*, 23:157-66 (1997).
Infante-Rivard et al., Otitis Media in Children: Frequency, risk factors, and research avenues, *Epidemiologic Reviews*, 15(2): 444-65 (1993).
Jansen et al., Immunotoxins: Hybrid molecules combining high specificity and potent cytotoxicity, *Immunological Rev.* 62:185-216 (1982).
Kaplan et al., Overall cost in the treatment of otitis media, *Pediatr. Infect. Dis. J.*, 16(2):S9-11 (1997).
Karma et al., Immunological aspects of otitis media: present views on possibilities of immunoprophylaxis of acute otitis media in infants and children, *Int. J. Pediatr. Otorhinolaryngol.*, 32:S127-34 (1995).
Kennedy et al., Passive transfer of antiserum specific for immungens derived from a nontypeable *Haemophilus influenzae* adhesin and lipoprotein D prevents otitis media after heterologous challenge, *Infect. Immun.* 68(5):2756-2765 (2000).
Klein, Role of nontypeable *Haemophilus influenzae* in pediatric respiratory tract infections, *Pediatr. Infect. Dis. J.*, 16(2):S5-8 (1997).
Kramp et al., Liposomal enhancement of the immunogenicity of adenovirus type 5 hexon and fiber vaccines, *Infect. Immun.* 25(2): 771-3 (1979).
Lee et al., Constitutive and inducible green fluorescent protein expression in *Bartonella henselae*, *Infect. Immun.*, 66(8): 3964-7 (1998).
Lysenko et al., Bacterial phosphorylcholine decreases susceptibility to the antimicrobial peptide LL-37/hCAP18 expressed in the upper respiratory tract, *Infect. Immun.*, 68(3):1664-71 (2000).
Margolis et al., Identification of hearing loss in children with otitis media, *Ann. Otol. Rhinol. Laryngol.*, 103: 59-61 (1994).
Marra et al., Differential fluorescence induction analysis of *Streptococcus pneumoniae* identified genes involved in pathogenesis, *Infect. Immun.*, 70(3):1422-33 (2002).
Marra et al., In vivo characterization of the psa genes from *Streptococcus pneumoniae* in multiple models of infection, *Microbiology*, 148: 1483-91 (2002).
Mason et al., Nontypeable *Haemophilus influenzae* gene expression induced in vivo in a chinchilla model of otitis media, *Infect. Immun.*, 71(6): 3454-62 (2003).
Matteucci et al. Synthesis of deoxyoligonucleotides on a polymer support, *J. Am. Chem.*, 103(11):3185-91 (1981).
Mhlanga-Mutangadura et al., Evolution of the major pilus gene cluster of *Haemophilus influenzae*, *J. Bacteriol.*, 180(17): 4693-703 (1998).
Mitchell et al., Electroporation of *Haemophilus influenzae* is effective for transformation of plasmid but not chromosomal DNA, *Nucl. Acid Res.*, 19(13): 3625-8 (1991).
Miyamoto et al., Selective adherence of non-typeable *Haemophilus influenzae* (NTHi) to mucus or epithelial cells in the chinchilla eustachian tube and middle ear, *Microbial Pathogenesis*, 21: 343-56 (1996).
Musher et al., Opsonizing and bactericidal effects of normal human serum on nontypable *Haemophilus influenzae*, *Infect. Immun.*, 39:(1): 297-304 (1983).
Musser et al., Genetic relationships of serologically nontypable and serotype B strains of *Haemophilus influenzae*, *Infect. Immun.*, 52(1):183-91 (1986).
Nichols et al., Identification of the ADP-L-glycerol-D-mannoheptose-6-epimerase (rfaD) and Heptosyltransferase II (rfaF) biosynthesis genes from nontypeable *Haemophilus influenzae* 2019, *Infect. Immun.*, 65(4):1377-86 (1997).
Novotny et al., Epitope mapping of the outer membrane protein P5-homologous fimbrin adhesion of nontypeable *Haemophilus influenzae*, *Infect. Immun.*, 68(4):2119-28 (2000).
Padmalayam et al., Molecular cloning, sequencing, expression and characterization of an immunogenic 43-kilodalton lipoprotein of *Bartonella bacilliformis* that has homology to N1pD/LppB, *Infect. Immun.*, 68(9): 4972-9 (2000).
Papp, Management of otitis media with effusion in young children, therapeutic controversies, *Ann. Pharmacother.*, 30:1291-7 (1996).
Poolman et al., Developing a nontypeable *Haemophilus influenzae* (NTHi) vaccine, *Vaccine*, 19:S109-15 (2001).
Ray et al., Tricross: Using dot-plots in sequence-id space to detect uncataloged intergenic features, *Bioinformatics*, 17(12):1105-12 (2001).
Rock et al., The licC gene of *Streptococcus pneumoniae* encodes a CTP:phosphocholine cytidylytransferase, *J. Bacteriol.*, 183(16): 4927-4931, Aug. 2001.
Sawitzke et al., Suppression of chromosome segregation defects of *Escherichia coli* muk mutants by mutaions in topoisomerase I, *Proc. Natl. Acad. Sci. USA*, 97(4):1671-6 (2000).
Schneider et al., Virulence gene identification by differential fluorescence induction analysis of *Staphylococcus aureus* gene expression during infection-simulating culture. *Infect. Immun.* 70(3): 1326-33 (2002).
Shen et al., Molecular determinants of disease and resistance in interactions of *Xanthomonas oryzaepv.* oryzae and rice, *Microbes Infect.*, 4:1361-7 (2002).
Snow, Progress in the prevention of otitis media through immunization, Otol. Neurol., 23:1-2 (2002).
Spinola et al., Epidemiology of colonization by nontypable *Haemophilus influenzae* in children: A longitudinal study, *J. Infect. Dis.*, 154(1):100-9 (1986).
Suzuki et al., Synergistic effect of adenovirus type 1 and nontypeable *Haemophilus influenzae* in a chinchilla model of experimental otitis media, *Infect. Immun.* 62(5): 1710-8 (1994).

Teele et al., Otitis media in infancy and intellectual ability, school achievement, speech, and language at age 7 years, *J. Infect. Dis.*, 162:685-94 (1990).

Tomb J-F., A periplasmic protein disulfide oxidoreductase is required fo transformation of *Haemophilus influenzae* Rd, *Proc. Natl. Acad. Sci. USA*, 89:10252-6 (1992).

Tong et al., Evaluation of phase variation of nontypeable *Haemophilus influenzae* lipooligosaccharide during nasopharyngeal colonization and development of otitis media in the chinchilla model. *Infect. Immun.*, 68(8): 4593-7 (2000).

Valdivia et al., Flow cytometry and bacterial pathogenesis, *Curr. Opin. Microbiol.*, 359-63 (1998).

Valdivia et al., Bacterial genetics by flow cytometry: rapid isolation of *Salmonella typhimurium* acid-inducible promoters by differential fluorescence induction, *Molec. Microbiol.*, 22(2):367-78 (1996).

Valdivia et al., Fluouescence-based isolation of bacterial genes expressed within host cells, *Science*, 277:2007-11 (1997).

Van Ulsen et al., Genes of non-typeable *Haemophilus influenzae* expressed during interaction with human epithelial cell lines, *Molec. Microbiol.*, 45(2):485-500 (2002).

Weiser et al., Decoration of lipopolysaccharide with phosphorylcholine: a phase-variable characteristic of *Haemophilus influenzae*, *Infect. Immun.*, 65(3): 943-50 (1997).

Weiser et al., Phosphorylcholine on the Lipopolysaccharide of *Haemophilus influenzae* contributes to persistence in the respiratory tract and sensitivity to serum killing mediated by C-reactive protein, *J. Exp. Med.*, 187(4): 631-40 (1998).

Wilson et al., Identification of listeria monocytogenes in vivo-induced genes by fluorescense-activated cell sorting, *Infect. Immun.*, 69(8): 5016-24 (2001).

Wood, Guide to Molecular Cloning Techniques, 152: Section IX, Chapter 49, 443-57 (1987).

Yamanaka et al., CspD, a novel DNA replication inhibitor induced during the stationary phase in *Escherichia coli*, *Molec. Microbiol.*, 39(6):1572-84 (2001).

Young et al., A Bifunctional urease enhances survival of pathogenic *Yersinia enterocolitica* and *Morganella moganii* at low pH, *J. Bacteriol.*, 178(22):6487-95 (1996).

Zhang et al., Structure of thermotoga maritima stationary phase survival protein SurE: A novel acid phosphatase, *Structure*, 9:1095-106 (2001).

International Search Report dated Feb. 17, 2005 in corresponding PCT application No. PCT/US0224/007001.

Written Opinion for corresponding PCT application No. PCT/US2004/007001.

Figure 3A

SEQ ID NO: 589

TTNAACAAGANATTGGGACAACTCCAGTGAAAAGTTCTTCTCCTTTACTCA
TATGTATATCTCCTTCTTAAATCTAGAGGATCAAGCAACTTAATTTTTGGT
TTGCGACATAGACAATTTTCTTCGGGCTTATGCGGGCAAATGAGTACTTCA
TCAAAGGTAATGCCCTGAGATTCAAATAATGCCATCATTACATTGTGGGG
CTTATCAAAATTTGTTTGCGGAAAAGCATCCGTACCAAGCCCATCTTGATT
AGAAACTATCACAAAACGGTATTTCGCTTTCAGTCTGAGGAGTGCGGGAA
TCACTTTCGGTTCTAATTTTAGTTTCTCTAAACTGTCAATTTGGAAATCAGT
TTTTGGTTCATCAATTAATGTGCCGTCTCGGTCGATAAAAGAGTAGGTTG
CATATTTTTCTCCGTGTATGTTATATGAATGGTATGAGGTTTATCATTTGCT
TTATACAAACAGTATAAAACTAAATAATCTCGAATCGCTCTGTGACTTAA
ATAGGAGGTGGTTCATTTTACCTCCTTAATTGCTTCAACAACTTTCTCACA
CTCATTCCTTGTTCCCACAGTAATGCGAATACAATTTTGT

Nt 80-410 of SEQ ID NO: 589 corresponds to compliment of nt 1-331 of the *hisB* gene.
Nt 80-600 of SEQ ID NO: 589 corresponds to nt 4655-5175 of the contig 532 (SEQ ID NO: 532).

SEQ ID NO: 590

TAACAAGAACTTGGGACAAAGNCCAGTGAAAAGTTCTTCTCCTTTACTCA
TATGTATATCTCCTTCTTAAATCTAGAGGATCAGCATCACATCGGGCGGAA
TAGGAAAAAATATCGCCTCGATAAAACTTACAAAAGAGAGCCAAAAAAC
AGCAAAACGATGTTTTGACCATTCCATCGTTTTATCGTACATCGTGCCGAA
AATTTTCATATTTTTCTCTATTTGGTAAATTCCTGCTCTAACCAATTTTGCA
AAGAAAGCAATGAATGATATGCGGTAAGATCCTCTAGAGTCGACCTGCAG
GCATGCAAGCTTGGCGTAATCATGGTCATAGCTGTTTCCTGTGTGAAATTG
TTATCCGCTCACAATTCCACACAACATACGAGCCGGAAGCATAAAGTGTA
AAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGA
ATCGGCCAACGCGCGGGGAGAGGCGGTTTGCGTATTGGGCGCCAGATACC
GGCCTCCATCGGAGAAACTGTCCGAGGTTATGTTGACCTGCAGGG

Nt 78-210 of SEQ ID NO: 590 corresponds to compliment of nt 1-133 of the *lppB* gene.
Nt 78-285 of SEQ ID NO: 590 corresponds to compliment of nt 1423-1630c of the contig 442 (SEQ ID NO: 442).

Figure 3B

SEQ ID NO: 591

NACAGATTGGGACAACTCCAGTGAAAAGTTCTTCTCCTTTACTCATATGTA
TATCTCCTTCTTAAATCTAGAGGATCCACAATAATATGTTCTATCTTGGCTT
CTTTTTTCCAATAGTTTTCGTTACGCACTAAGCGAACATATTGGTTATATA
CATAATCTTTTACTTGATAAGGCCCTGTGCCTACTGGGTGGGTATCTAATT
GAGCAAGGTTGTCATCTGCGCTTAATTGATAGGCATATTCTTGTGAAAAA
ATAATGGCATACTGGCTGGCAAGATGCGACAAAATGGAGGAATCTGGTGC
AAATAATTCAATTTTTACTTGATAAGGCGAAAGTGCGGTCACAGATTTGAT
TTTTTCGTTAAGTTTAATGCTATCAAAATAAGGAAAACGCACTTTTCTTGC
TTGTTCGTGAAACACTCTATATTGTGGATTACTATAGGNAACCATNCGCCT
CTGCTAAGGTTGGTAAATAAGTATTATGCCCTAATACACGATTAATCGAA
AATACTTCNGTNTTCAGNGNTAAAAACACCNTGNNGGGGNAAANCNANG
GGGTTTGGGGGAAATTTTACCCCCGGGACGTAAATTNAATAAA

Nt 74-514 of SEQ ID NO: 591 corresponds to compliment of nt 369-811 of the *sapA* gene.
Nt 74-514 of SEQ ID NO: 591 corresponds to nt 3458-3897 of the contig 512 (SEQ ID NO: 512).

SEQ ID NO: 592

TTAACAAGNAATTGGGACAACTCCAGTGAAAAGTTCTTCTCCTTTACTCAT
ATGTATATCTCCTTCTTAAATCTAGAGGATCGTAGAACCATAAGGTTTTAC
CATCAGAAATAATCTGGGTTTCTTGAGGGGTTTTAGTCTCCATACGGAATA
AATTTGGGCGTTTAATTTGAAGTTTGCCACTTCCTTGTTGAACATTTTTCC
ACTTCCAGAAGTCACTGTTTGCACAAATTCTGCACTTAATACATCGACTTT
AGCTAAACGCATTTGTAATTCACTTGCCGCATCAGCCAATGCCAAATTACT
CAAACCAAGTAAGGTAAGTGCGGCAAATTTTAAGGTTGTTTTTTTCATTTT
ACTTTCCTTTTAAATTAGTATTCTGGACGATGCGATAAAATTTCACGCTTA
CCATTTTGCATTGGGCTGACAATCCCTTGCTCTTCCATTTGATCCTCTAGAG
TCGACCTGCAGGCATGCAAGCTTGGCGTAATCATGGTCATAGCTGTTTCCT
GTGTGAAATTGNTATCCGNTCACAATTCCCACAACATACGAGCCNGAAGC
ATAAAGTGTAAAGCCTGGGGGGNCTNATGAGGGAGCTA

Nt 78-345 of SEQ ID NO: 592 corresponds to the compliment of nt 11-278 of the *lolA* gene.
Nt 78-454 of SEQ ID NO: 592 corresponds to compliment of nt 1039-1415 of the contig 360 (SEQ ID NO: 360).

Figure 3C

SEQ ID NO: 593

TTAACAGAATTGGGACAACTCCAGTGAAAAGTTCTTCTCCTTTACTCATAT
GTATATCTCCTTCTTAAATCTAGAGGATCTATACCTGCAATTAAAATAACG
AAAGTCATACCCACTGCAATAATCGCATTAACCGAAGTTTGGCGTAAAAT
ATTCAAAATATTATCTACGCTAAAAAAATCAGGATTAATCATTGATACAA
TCGCGATAAGAATAATCAACGCAATAAAAGAACGCTGTTCAATCAAAAAT
CTTCCTATTTGAAAATTAGATGTTTCATTTTTCATCATACTTACCTACTCTT
ATTTACCAATAGCTGCTGCTAATAATTTTTCTTGAGTTGCGTCTTTGCGAG
AAAATTCTGCACTAATTTTACCTTCACGCATTACCAACACTCTATCGCTCA
TACCAAGCACTTCTGGCATATCAGATGAGATCCTCTAGAGTCGACCTGCA
GGCATGCAAGCTTGGCGTAATCATGGTCATAGCTGTTTCCTGTGTGAAATT
GNTATCCGNTCACAATTNCACACAACATACGAGCCNGNAGCATAAAGGG
GAANNCCGGGGGGCCTAANGGGGNGCTACNNNATTNATNGGGTG

Nt 77-290 of SEQ ID NO: 593 corresponds to compliment of nt 1-214 of the *rbsC* gene.
Nt 77-438 of SEQ ID NO: 593 corresponds to compliment of nt 1813-2174 of the contig 445 (SEQ ID NO: 445).

SEQ ID NO: 594

AAGTACTCTGTNTNTCTCCTTCTTAAATCTAGAGGATCGGGATTATCAAGC
ACATTACTCGTTTGGCTTTCACGGAAAGATTGCAAGCGTGAAAGCAACTT
CTGCATCCCAACTTGCTAGAATTTGTGCGGCTAACAATCCAGCATTTGCCG
CACCCGCAGGGCCAATAGCCAATGTTCCGACTGGGATTCCTTTTGGCATTT
GCACAATTGAATAAAGGCTATCTACGCCACTTAACATAGAACTTTTACTG
GCACACCCAGCACAGGCACAAGGGTTTTGGCTGCGATCATGCCGGGTAAA
TGTGCCGCACCGCCAGCCCCAGCAATAATTACTTTATAGCCATTTTTTTGT
GCATTTTCAGCAAATTCAAAAGTTTATCAGGCGTACGATGAGCAGAGAC
GATTTCCACATGATAAGGTACTTTTAATTCATCTAAAATCTGAGTTGCCTC
TTGCATGGTAGCCCAATCGCTTTTGGAACCCATCACAACAGCAATTTGTGC
AGTTTTTGACATGCTATTTTCTCAATTTTCTAATTAAAAGGTGGCGTAGA
ATAGCATAGATTACATATATTGAGCAAACGTTTGCTATNTAT

Nt 105-519 of SEQ ID NO: 594 corresponds to compliment of nt 1-415 of the *purE* gene.
Nt 34-281 of SEQ ID NO: 594 corresponds to compliment of nt 286-40 of the contig 536 (SEQ ID NO: 536).

Figure 3D

SEQ ID NO: 595

TTATGNGACCNTGGGACAAGTCCAGTGAAAAGTTCTTCTCCTTTANTCATA
TGTATATCTCCTTCTTAAATCTAGAGGATCTTCATCATCTAAAACTAATAC
GCCAGTTCCATGTTTGAAAGCATTAATTGCATTAAGTACGCGTTCTTCAGC
GGTGTTGCCGAATGGAGATAAAATTGACTGATTCATAGTAATTTCCTAATT
TGAGATTTCAATTAAATACCAGAATCAGGGCTGAGAAATGCAAATAAAAT
GAACGATTTGGGAACCCAACTCGTTTTATTCTCTTTCATCCAGACTTTACT
GTCGGCTTTGGAATTTCACCAAATCTGCTGACTTTAAAAGTGAAAATCAG
GACAATTTCGCAGGAAAAATTTGCCAAAAATTGACCGCACTTTTAAACGC
TCGTGGGCTTTACCACCGGTAGGGAATTTCACCCTGCCCTGAGAATGCGA
GCTAAGTATAACGCAAAATACCTAGGCACTAAATCAGAACGTGAAAAATA
TTTTCATTTAGCCTACAATAAACACACTCAATTCTTACGCTATCAAGAGCA
GATTATGTCAAAAACAAAAGAGAAAAAAGTCGGTGTCATTTTCG

Nt 78-189 of SEQ ID NO: 595 corresponds to compliment of nt 1-112 of the *ribB*
gene.
Nt 237-565 of SEQ ID NO: 595 corresponds to compliment of nt 2216-2544 of the
contig 290 (SEQ ID NO: 290).

SEQ ID NO: 596

TNACAGNAATTGGGACAACTCCAGTGAAAAGTTCTTCTCCTTTACTCATAT
GTATATCTCCTTCTTAAATCTAGAGGATCTAAGAGATATTTAATTTCACGT
TCTGTGTGATGAACAAGACTAAGTAAATGTCTATTTTTCATATTGAAAGCC
ATAATAATCTCCTTGTGTTTTGACTATACATTGGGGAATAAACATACATCA
TTCGAGATACTGCTTGTTGTTCGAACAGTTGCATTATAAGAGAGGTAAAAT
GAAATTTGTTGTCGTTTTCAACTGGTAATGCCAGTATGTAGAATTTTATT
GCGAGATTTTTAGTATTATTAGAATTTAATAAAAATAATCTAACTCTTTAT
TGTTATTTGTTTGATTTCTAATAGTAGATGAATTTAAACGAAAATATGTTT
TAGTTTATTTTTGATGAAGAGGAATGNGTCTATCTATNCTTAATAAAAGNG
CGGNTATTTTTATTGNAGNTTTTAATATATTGATCCTNTAGAGAGCGACCC
NCACGCNTGCGCNCTTGGGGCGANCATGGGGCATATAGTTGTTCCCTGTG
NNAANGTGTTATCCGTTCACANTTCCCCACAAAANACGAN

Nt 77-155 of SEQ ID NO: 596 corresponds to compliment of nt 1-79 of the *arcB*
gene.
Nt 77-494 of SEQ ID NO: 596 corresponds to compliment of nt 772-1189 of contig
461 (SEQ ID NO: 461).

Figure 3E

SEQ ID NO: 597

AACAGNATTGGGACAACTCCAGTGAAAAGTTCTTCTCCTTTACTCATATGT
ATATCTCCTTCTTAAATCTAGAGGATCAGTACGAGTCCAGTCTAAAACAG
GCATAAAATTGTAACAAACAGTGTCAATTCCGCATTGAGCAAGCATTGCG
AGAGAGTTTGTTTATAGTTATTAATCCATTTTGATAATTTCCAGTACTGA
GTTTTAATCTCTTCATGAACTGGTACACTTTCCACTACTGACCAGCTTAAA
CCAGCATTCTCTATTTCAGTTTTGCAGTTTTTTAATTTCTTCGATACTCCAC
ACTTCACCGTTAGGAATATGGTGAAGTGCAGTGACTATACCAGTTGCGCC
TGCTTGACGAATATCAGATAAAGAAACAGGATCCTCTANAGTCGACCTGC
AGGCATGCAAGCTTGGCGTAATCATGGTCATAGCTGNTTCCTGTGNGAAA
CTGGTATCCGCTCACAATTCCACCNAACATACGAGCCNGAAGNCATAAAG
NGNTAANCCNTGGGGNGCCTAATGAGTGAGCTAACTCACATTAATTGNGT
TGGGCTTACTGCCCGTTTTCAGNNGGGAAACCTGGCGCGCCAGCT

Nt 83-388 of SEQ ID NO: 597 corresponds to compliment of nt 34-335 of the *uxuA* gene.
Nt 156-388 of SEQ ID NO: 597 corresponds to compliment of nt 779-1008 of the contig 5 (SEQ ID NO: 5).

SEQ ID NO: 598

TNACAAGNAATTGGGACAACTCCAGTGAAAAGTTCTTCTCCTTTACTCATA
TGTATATCTCCTTCTTAAATCTAGAGGATCAACCTCGTAACTTAGCAAAAT
CAGTTACCGTTGAATAAAGTGCGGTTGATTTTAATGTAATAAAAAAAACG
GTGAAATTTCACCGTATTTTTTTAGTTAAATAATCTTCTTTGTTTCCGTGTT
TTAATCACTTGTGCGATTAACAATAATGTGAGAATAACCACATATAGTGA
AAAAATAACCACTAGCCATTGCACCATCGTTAAACCAAATAATGACCATT
GGCTTTCATTACAAGAGCCAGTTGGGTTAAATATAAATGGAAACCATTGA
TGAAATGGTAAAGTCTCGGGAAAATTTGGAATAAACTCACATTGTTTCCA
AGGAGCTGGATTCATTTGCAAATCAAGATGACGAAATGAAATCAATAAGC
CCTTAATACTGCTGAATAAACCTAAAGCCAAGGCGATTAATCGAAGTATG
AAAGCAAGAGGTTGAAGTAATGCAATAATGCCCGCTACAAATAAGCCAAT
CATTGCTAAACGTTCATAAACACAGAGCACACAAGGTTGTAAGCCC

Nt 176-600 of SEQ ID NO: 598 corresponds to compliment of nt 108-532 of the *dsbB* gene.
Nt 78-600 of SEQ ID 598 corresponds to nt 819-1341 of the contig 560 (SEQ ID NO: 560).

Figure 3F

SEQ ID NO: 599

NACAAGATTGGGACAACTCCAGTGAAAAGTTCTTCTCCTTTACTCATATGT
ATATCTCCTTCTTAAATCTAGAGGATCGCCCGCCAGCACCCCAGGGGAGG
AGGACATCTGCATCGCATTCAAGCCATTCGCCCACGCATCATCGTAACTTG
GCAACGTTATCACTTTAAACGGTGGCGTCGCAAAGTATTCAGCAAGCTGG
GTTTTACCGCTGGAGGAAAGTTTGGTGGAAAGGGATAATTTGCTGTTCAT
AGATTTTGTAGGGGCTAATTACATTAGCCCCGATATTTCACCAATAATTGG
GCAAATGTAATTTGCCCCTACGATTAACGAACCAAAGATGCAGGTTCTTC
CACATTCTTCAACAACGCATATTTTTCGATCCTCTAGAGTCGACCTGCAGG
CATGCAAGCTTGGCGTAATCATGGTCATAGCTGTTTCCTGTGTGAAATTGT
TATCCGCTCACAATTCCACACAACATACGAGCCGGAAGCATAAAGTGTAA
AGCCTGGGGTGCCTAATGAGTGAGCTAACTCACATTAATTGCGTTGCGCTC
ACTGCCCGCTTTCCAGTCGGGAAACCTGTCGTGCCAGCTGCATT

Nt 75-252 of SEQ ID NO: 599 corresponds to compliment of nt 1-178 of the *ureH* gene.
Nt 75-385 of SEQ ID NO: 599 corresponds to nt 825-1135 of the contig 258 (SEQ ID NO: 258).

SEQ ID NO: 600

TANACAAGNAATTGGGACAACTCCAGTGAAAAGTTCTTCTCCTTTACTCAT
ATGTATATCTCCTTCTTAAATCTAGAGGATCCAATCTCAATACGTATTACT
TGCCCATTACTATTTAAAATCGGTAGCCATTCATTGTGCGTTTTAGAACGG
ATAACCGTGAAATATTTGCTGTGTGATGGTTTCGTTAGAAAAATATTACGA
TTAAGCACTACATCCGCATCAATAACATAACAATCACTAAAGAAGTCTTG
TGCCAGAGAAAAGGAATAAATGCTGTTATATTCGCGATATTTTTCGTTGTA
AATCAAGGTGCAGTCATATTTTTTCTTTAGATACTCGAATTGTTCGTGTAA
ATACCCTGTAACAATGACAATATTGTCGATATTTGCTTGACGTAGAAAAGT
GAGTGTCCGTTCTAAGTTAGGTGTGCCGTGAATATCTAACAATGATTTATG
TGTGCTTTGTGTGATGTCTTTAAAACGACCGGCTTANTCNTGCAGCTAAAA
TAATCGCATTCATTTTTGTTCCCCTTTGNAAAAAAGTGTACCGATCCTCTA
GAGTCGACCTGCAGGCATGCAAGCTTGGCGTAATCATGGN

Nt 82-482 of SEQ ID NO: 600 corresponds to compliment of nt 40-440 of the *licC* gene.
Corresponding sequence not in contig set.

Figure 3G

SEQ ID NO: 601

TNACAAGANTTGGGACAACTCCAGTGAAAAGTTCTTCTCCTTTACTCATAT
GTATATCTCCTTCTTAAATCTAGAGGATCGCTCATTCGAGAGACACCTCCA
ACAGCACGAATATCTGCAGGAATTCGTTCCAAAGCCATCACTGCAGCTGC
ACCAGCAGCTTCTGCAATGCGAGCTTGTTCAGGGTTTTGAACATCCATGAT
AACACCACCTTTGAGCATCTGTGCTAAGTTTTTATTTAGTTCATAACGATT
TTCAGCCATTTCTTTGTCCTCATTATTTGGTTATTTGTATTGATAGCTACGT
TTTTTATTGTAATGTAGAAAAGTCTTTAGAACAAGTTTGAAAAAATGCGTA
TATATTAAAAGGCATAATGTCTAGTGTGCTTAATTTCAGTTTTTTGTATAA
ACGAAGTGTAGAACGTCAGAAGGATTGTCCAATTTAATAATAGAAAAAAG
AGCTACTTTAGCTGAAAGAATTTCGTCCTTAAGTGCCACAATAGTTATTAA
AAAAACCTTGAAATGTTTTTAAAAACCTTTTTCTATGTGGTTAGATTTTCT
GAAATTTAAGAAAAAGCTTGAAAGGGAGTTTACGCTTTCC

Nt 75-263 of SEQ ID NO: 601 corresponds to compliment of nt 1-189 of the HI1647 gene.
Nt 75-600 of SEQ ID NO: 601 corresponds to compliment of nt 1035-1560 of the contig 471 (SEQ ID NO: 471).

SEQ ID NO: 602

TTNACAAGGAATCGGGACAACTAGCAGTGAAAAGTTCTTCTCCTTTACTA
CATATGTATATCTCCTTCTTAAATCTAGAGGATCTGCAAAATTGTTGCAAC
CACTAATACGATGGCTGCTTCACGTACACCACCGAGTTTGTAAGTGATAA
AAAATAAAATTAAAGGGATAAAGTCAAGGAGTTGTTTCATATTGATTAAT
CCTTCATAAATAAGCTGTAGAAACGATAAGTCACTACTAGCATGAAAATA
TTAAGTAATGCGGTGAAAATGCCTATTACCATATCAAATATAGCATTATTG
GAAAATGCGCTTAATTGGAAAATAAGAATTGGCACGAGAAAATAAACCA
GTAGGGTGTAAATAAACAATACGCCTTTTCGAGTATTTCCTCGCATCCAAA
TTTTTCGGATAGTTTGCGAAAGTGCCTCTTGAGTAGAAAGATAATGTACTA
CCGTTAAATTTTAAACGGACAAAGAACCAAACGCCAACAAGCATCGCGAT
AAGTGACATAATAGAGGGCGATTTTTTTGTGAGTAATGCANCAAAGGCTT
CACCAAGNACCAGTAACATTGGTGCAACCATTAATAGATCCTCTTAG

Nt 81-191 of SEQ ID NO: 602 corresponds to compliment of nt 1-111 of the *ispZ* gene.
Nt 81-593 of SEQ ID NO: 602 corresponds to compliment of nt 850-1361 of the contig 418 (SEQ ID NO: 418).

Figure 3H

SEQ ID NO: 603

NACAAGANTTGGGACAACTCCAGTGAAAAGTTCTTCTCCTTTACTCATATG
TATATCTCCTTCTTAAATCTAGAGGATCCTTGAAACATCACCTCAGATTTA
ATCAATCTGTGGATTCTATCCAAGAAAAGTACCACGAAATTTTCTCTTTCC
TCATTACCTATAATGGTTTGAAAATAGAGTTTAGCTATTGATGGCTCAGTA
AATTCCTGTGCACCTTGGTAAAAGGGCTTTTCTTCCATCACTTTAGTTAAA
ATAACCTGTGCCTGTTCTAAAATAGCTTGTTGTTGCTCGTTTAATTTAAAC
ATTCGATATTCCTTCTAAAATAGGGAATATCGCCCATAAGGGATATATCCC
CTATGGGTAAGGTGCGAAAAGAATGCTTATCGCACATTAAAGTTAATGTT
ATTAATCAGAAGTTTTTAAACTGTCGATAATCTGTTTAATTTTTGCTGCAA
ATTCTAAATCGTGCTCAGATTCATCATCTATACAATATTCCAAATAATTAC
TCATATCAGCAATTAGTGCTTCTTTTGTTGGCGAAGGTTGGAACATAATTG
ATCCTCTAGAGTCGACCTGCAGGCATGCAAGCTTGGCGTA

Nt 65-525 of SEQ ID NO: 603 corresponds to compliment of nt 18-477 of the *radC* gene.
Nt 76-564 of SEQ ID NO: 603 corresponds to compliment of nt 23606-23869 of the contig 575 (SEQ ID NO: 576)

SEQ ID NO:604

TTAACAAGNAATTGGGACAACTCCAGTGAAAAGTTCTTCTCCTTTACTCAT
ATGTATATCTCCTTCTTAAATCTAGAGGATCGGCTTCTAACATTTCGCCGT
CTAAACGTTCGTTGTTATAAATTGCAATCGCCAGCAGGAAAACCAAGCGT
TCGGTAGGTAAATTCAAAGAAAACTCGCGATCTTTTGCCCAAGAGACGAG
TTCAGGAATAGTTTGGGATGTTTCAATCATTGAATTGCAAAGCGTTAAAAT
TGAACAAAAAATTGGAAAGATTATACAGGATTTTTTGCGGATCCTCTAGA
GTCGACCTGCAGGCATGCAAGCTTGGCGTAATCATGGTCATAGCTGTTTCC
TGTGTGAAATTGTTATCCGCTCACAATTCCACACAACATACGAGCCGGAA
GCATAAAGTGTAAAGCCTGGGGTGCCTAATGAGTGAGCTAACTCACATTA
ATTGCGTTGCGCTCACTGCCCGCTTTCCAGTCGGGAAACCTGTCGTGCCAG
CTGCATTAATGAATCGGCCAACGCGCGGGGAGAGGCGGTTTGCGTATTGG
GCGCCAGATACCGGNCTCCATNGGANAAACNGTCCCAGGGTNTNT

Nt 79-296 of SEQ ID NO: 604 corresponds to compliment of nt 30-247 of the *mukF* gene.
Nt 79-296 of SEQ ID NO: 604 corresponds to compliment of nt 4026-4243 of the contig 508 (SEQ ID NO: 508).

Figure 31

SEQ ID NO: 605

TAACAGNATTGGGACAACTCCAGTGAAAAGTTCTTCTCCTTTACTCATATG
TATATCTCCTTCTTAAATCTAGAGGATCCACGTAATCAGAATTTTCTGCAG
AAGATGGCGATGCCGCACCACCGTGATGGCGGCGAATTAAATCTAACTCC
GCCAAAATATTCAAATCACGACGAATCGTTTGAGGGCTAACATCTAAGGC
AGCAACCAATTCTTCCGTGCTTAAATAGCCAGATTGTTCCACCAGTTTAAT
AATTTTTTGATGGCGTAACGATTGTTTCATAGCGAATCCTTTATCCAAATT
AAACGGACTTACTCTAGCGAATTTTTGCGCAATTTGCTATCAATAAATCCC
CAAATCAAGCCGACAATCAAGCCTGAAATATGTGCAGCATTTCCCATTTC
AACACCAAATAAGGGGCTAATAAAACCTAATGCGATCCTCTAGAGTCGAC
CTGCAGGCATGCAAGCTTGGCGTAATCATGGTCATAGCTGTTTCCTGTGTG
AAATTGTTATCCGCTCACAATTCCACACAACATACGAGCCGGAAGCATAA
AGTGNAAGCCTGGGGNGCCTAAGGGTGAGCTAACTCACATTATT

Nt 76-283 of SEQ ID NO: 605 corresponds to compliment of nt 1-208 of the *glpR* gene.
Corresponding sequence not in contig set.

---

SEQ ID NO:606

TAACAAGAATTGGGACAACTCCAGTGAAAAGTTCTTCTCCTTTACTCATAT
GTATATCTCCTTCTTAAATCTAGAGGATCACCATTTTCAAGAGATTGAGAA
ATAAACTCTAAAATATCTTTTACCATATTTTCAATTTCTTTTGCAGATAAA
GTTGGCTGTTTTGCTGACAATTTTTCCATAAGTTCTGACTTAGTCATCCTCT
ATACTTCCTTAATATTATTTAAATTAAGATCCTCTAGAGTCGACCTGCAGG
CATGCAAGCTTGGCGTAATCATGGTCATAGCTGTTTCCTGTGTGAAATTGT
TATCCGCTCACAATTCCACACAACATACGAGCCGGAAGCATAAAGTGTAA
AGCCTGGGGTGCCTAATGAGTGAGCTAACTCACATTAATTGCGTTGCGCTC
ACTGCCCGCTTTCCAGTCGGGAAACCTGTCGTGCCAGCTGCATTAATGAAT
CGGCCAACGCGCGGGGAGAGGCGGTTTGCGTATTGGGCGCCAGATACCGG
CCTCCATCGGAGAAACTGTCCGAGGTTATGTTGACCTGCAGGGGGGGGGG
GGCCCCTGAGGTCTGCCTCGNGAAGAAGGGGTTGCTGACTC

Nt 77-200 of SEQ ID NO: 606 corresponds to compliment of nt 1-124 of the *ihfB* gene.
Nt 77-236 of SEQ ID NO: 606 corresponds to compliment of nt 1455-1614 of the contig 408 (SEQ ID NO: 408).

Figure 3J

SEQ ID NO: 607

NACAGNNTTGGGACAACTCCAGTGAAAAGTTCTTCTCCTTTACTCATATGT
ATATCTCCTTCTTAAATCTAGAGGATCAACATCTAAGACAAGATTTTTTAA
TGGACTACTGGTATTGGGAACACTTAATTCATTTGGTAAGCAATAGACCAT
TTCCATTTTTGTATTACGAGTGCGAACCGCACCAAATTTGCTGAGCATTCT
CGATATTTTTGATTGATTAATACCAGTAAAGCCTTGTTTTTTTAAGGCATC
GACAATTTCATTTTGAGAACCAAAGCGTTCTTGATTGAGTAATTCTTTAAA
AGCACGAGTTAAATTGTCAGTCATCTTTATTTTTTAATAGTCAAAATTTGC
ATAAGAATTGCATAAAAATTNNNCTTTCATCAACTGGAATATGGNTTNGN
ACCNNGGGGAAGAAATTTTTTTNNNNAAAATNGGAACNAGATCCNTTNAA
GNCAACCTGCAGGCATGCAAGCTNGGCGNAATCANGGCATAGCTGNTTCC
TGGGNAAATTGNTATCCGTTANAATTCCCNCNACATNCNANCCGNAGCAT
AAGNGAAAGCCTGGGGGCNTANGANGNGGCTACCCCCATNATT

Nt 75-330 of SEQ ID NO: 607 corresponds to compliment of nt 1-256 of the *argR* gene.
Corresponding sequence not found in contig set.

SEQ ID NO: 608

TTTAACAAGGAATCCGGGCACAACTACCAGTGAAAAGTTCTCTCTCCTTTA
CTCATATGTATATCTCCTTCTTAAATCTAGAGGATCCTTTATCGCTGTGGA
GAACTTCAAATTGTACTTTTTGACCTGCTTTTAATGAACGATAGCCGTCCA
TTTCAATCACTGAATAATGTGCAAAAATATCGGCATCTACACCTTCTGCGG
AAATGAAACCAAATCCTTTTGCATTATTGAACCATTTTACAATACCAATTT
CCATAAAAGACCTCTCTAGGCTTAGCCTATTAAAACAATAAATCAACAAG
ACTCTCGCCTTATCACCTACTAATTAGGTCCGTTATGTTTAAATATTTTGAA
CGGTTATGCAACGAGCAATATTCAAAAATGATAAGTAGATCCTCTAGAGT
CGACCTGCAGGCATGCAAGCTTGGCGTAATCATGGTCATAGCTGTTNCCT
GNGTGAAATTGTTATCCGCTCACAATTCCACACAACATACGAGCCGGAAG
CATAAAGTGNTAAGCNTGGGGTGCCTAATGAGTGNNCTAACTNACATAAA
TTGAGTTANGCTCACTGCNCCGTTTTCCAGNNGGNGANACCNG

Nt 84-259 of SEQ ID NO: 608 corresponds to compliment of nt 1-176 of the *ihfB* gene.
Corresponding sequence not found in contig set.

Figure 3K

SEQ ID NO: 609

TAACAGCATTGGGACAACTCCAGTGAAAAGTTCTTCTCCTTTACTCATATG
TATATCTCCTTCTTAAATCTAGAGGATCTATTACAGAACCATCATTTCCCC
AAATCAAGAATAGCTTTGATGAAAATAAGTAAAATCGGTAAGACAATAG
GAATACTCACGACATAGCCCGTAATGGCTAATGCCCATTCTTCCTTTTCT
TACCTAGAAATTTGATAAAACTGAACGCCATTTTTTCAGCAACTGGGCAG
ATTGAAGTTTCACCATGTAAAGGTTCTCGAATAATGCTACTTACAAAGGA
AGAAGTCGCTTTATTTGGTTTTCCTGGACGGATACAAATTGTGAGCAGGCG
AACACAGAGACCATCAACAAAACCTTTTCTTGTATAGTCATTAATAAGTA
ATTCACTCATTGCTTTTGTGCACCATAAGTCGATTGTGGCGTTACAGCAG
TAGAATCCTGAATAATTTCTGGTAAATCACCACCAAATACAGCAAGTGAA
CTAGAAAAAATAAAACGAATTTTAGTATCAGATTCATCAAAATATGAGAA
AGTGGCGACATTCCATATTTGTCCACTAACAAATTTTGATCCTCTA

Nt 93-413 of SEQ ID NO: 609 corresponds to compliment of nt 1-321 of the HI0094 gene.
Nt 76-595 of SEQ ID NO: 609 corresponds to nt 1467-1985 of the contig 379 (SEQ ID NO: 379).

SEQ ID NO: 610

TTNNACAAGNAATTGGGACAACTCCAGTGAAAAGTTCTTCTCCTTTACTCA
TATGTATATCTCCTTCTTAAATCTAGAGGATCATCAAGATAATCAAGTACA
TATTGTTCAATTTGAGGAATGCGATTTAGACTTGGCAACATAGTATTTAAC
TCATTTAAAGGTAAAAATGGCAGGTTATTGATAATATCTTAAGGCGTTAAT
GATGTCGAATTAGATTTTGAGCATTTTTAAGGAGTGTTTTATGGAGTAAAT
GAGTCAAGAAAAGTGTGTTGTTTGGATGAAAAATAAACNAAAAATTCAAA
AGAATTTGATCCTCTAGAGTCGACCTGCAGGCATGCAAGCTTGGCGTAAT
CATGGTCATAGCTGNTTCCTGTGTGAAATTGNTATCCGCTCACAATTCCAC
ACAACATACGAGCCGGAAGCATAAAGTGTAAAGCCTGGGGTGCCTAATG
AGTGAGCTAACTCACATTAATTGCGNNGCGCTCNCTNNCCCCTTTNCNCA
GGGGAAAACCCTGNCGCNCCAGCTGCNTTTAATGAATCNGCCCNCNCGCG
GGGAGGGGCNGNTTGCGTNTTGGGCGCCANANCCCGNCTCCATCG

Nt 80-143 of SEQ ID NO: 610 corresponds to compliment of nt 1-64 of the HI1163 gene.
Nt 80-316 of SEQ ID NO: 610 corresponds to compliment of nt 117-353 of the contig 513 (SEQ ID NO: 513).

Figure 3L

SEQ ID NO: 611

NACAAGNAATTGGGACAACTCCAGTGAAAAGTTCTTCTCCTTTACTCATAT
GTATATCTCCTTCTTAAATCTAGAGGATCGTCATCTTTACGATATTTTCAT
CAATTCGTTTTTGCAATCCAAAGTCATTTTTATCCGATTCGTTAGAAAATA
AATCTTCTGTTTGCGTTAATTGAGGATTTTGAATTCCTATCCAATTTGCAAT
CCCTTCTAAGAAATTTAAACCTGATTTAAACACCTTATATTCTTTGCGTTCC
ATATCATCTGATGAAATTTTGAATAGCGGAATATTATGGTGCTCTCGGCTG
AAACAGTTTTGATTGAACAAAGTATATTGTTTTTTCATCTTGTTGGTGG
CACAAACCGTGATCCTCTAGAGTCGACCTGCAGGCATGCAAGCTTGGCGT
AATCATGGTCATAGCTGTTTCCTGTGTGAAATTGTTATCCGCTCACAATTC
CACACAACATACGAGCCGGAAGCATAAAGTGTAAAGCCTGGGGTGCCTA
ATGAGTGAGCTAACTCACATTAATTGCGTTGCGCTCACTGCCCGNTTTCCA
GTCGGGAAANCCTGTCGTGCCAGCTGCATTAATGAATCG

Nt 76-260 of SEQ ID NO: 611 corresponds to compliment of nt 1-185 of the gene HI1063.
Nt 76-374 of SEQ ID NO: 611 corresponds to nt 229-527 of the contig 48 (SEQ ID NO: 48).

SEQ ID NO: 612

ATTNNACAAGNAATTGGGCACAACTCCAGTGAAAAGTTCTTCTCCTTTACT
CATATGTATATCTCCTTCTTAAATCTAGAGGATCATCTTTGATAATAAGCT
GTAATTTTGGTTGAAAACCTGAAATGCTCATCCCTTGCTGTTTTGGGGTT
TCACTGTAATAAATTCTTGGCGAGAAAAGGGCAATTCAGGATTAAAATGT
TTATTGCCTGTAAGATAGTGTAAACCTTTTGTGCTGTAACCAGAATGAACT
TCATTTTTTTTCAATGGCTTTAATAAAATACGACAAAAATTCATTGTTTTC
TTCCTGAATTTGCACTGCGCCTAACATATTTTCCCCGTTATTAAGTAAAAA
GCGAAACATATCGCTTTCATCAATTCGTTGATGAAGTGCATATTTGTGTTT
TAGCCAGCCTTCTGGGACGAGGGATGCAAAATAAGGGAATAAGGTGTNA
GAATGAAAAGGACTTTGCTCAATAGGAAAGCTGAGAGAGAGCGGTATTCC
TTGATAATCGGGATTGTAAGCAAAATGAAAACCTCGATGATCCTCTAGAG
TCGACCTGCAGGCATGCAAGCTTGGCGTAATCATGGTCATAGC

Nt 84-298 of SEQ ID NO: 612 corresponds to compliment of nt 1-215 of the HI0665 gene.
Nt 82-549 of SEQ ID NO: 612 corresponds to compliment of nt 4726-5193 of the contig 557 (SEQ ID NO: 557).

Figure 3M

SEQ ID NO: 613

NACAGNATTGGGACAACTCCAGTGAAAAGTTCTTCTCCTTTACTCATATGT
ATATCTCCTTCTTAAATCTAGAGGATCACTGCATTGAGTAAACGACTTTGT
GATTCAATATTATTTTCGAGTGCAGTCAGGCGAAAATAGGTTTCGATTAAA
TACATAAATTTTTTAATTGCTGTCTGATTTGGTTTAAGCCGTTTAAACGCAT
TTCACTTAAACGTTGTGAAATGCCGAGTTCGCTAAAAAAGGCAATAATAT
CAAATGTATTCAATTCATCCGCTGTTTGCCATTGATTTGATTGAATAAAA
TCCAAAGCAAGCCATTCATAATTCTGGCTTCGCTAAATCCGCTGAATTGAA
AAGTGCGGTCATGTTTAGGCATAATTTGAAACCACATTTGTGCTTCGCAGC
CAGNNAATAGGTTGCATTTGAGCGAGTTCATTATCGCTTGGGCGAGGNNA
ANNTTTTGNCTNCNCNGGAAAAATCAGGNNATNGCGATCCTTTAGAGTCG
ACCTGCAGGCATGCAAGCTTGGCNGTAATCATGGNCATAGCTGNTTCCTG
GGGGAAATNGTTNTCCGNTNCAATTCCCCACAACATACGAGC

Nt 75-158 of SEQ ID NO: 613 corresponds to compliment of nt 1-84 of the HI1292 gene.
Nt 142-455 of SEQ ID NO: 613 corresponds to nt 12-324 of the contig 313 (SEQ ID NO: 313).

SEQ ID NO: 614

CAAGACTTGGGACAACTCCAGTGAAAAGTTCTTCTCCTTTACTCATATGTA
TATCTCCTTCTTAAATCTAGAGGATCTACAGTTGGTTCTGTAAACATCCCA
GAACCGATTAAAATAAAATAACCCGCGAATGCGGCACAAATCACCGCAA
AAAGTGCGGGCAAAATTTGGCTTGTTTTTTCGTGTTCATCATTGTCTTCCC
TGAAAAGAAAATATCGCTATTATCCACCTTTCACTCAGAATTTCCATATTT
AACTTCTTCACTCTTGAGCGGTTATTTTATAGAATAAGCCAATTTTTTTAA
GCCAGAAGGAAAAAACAATGAGCCAACCAATTTATAAACGTATTTTATTG
AAATTAAGCGGTGAAGCATTACAAGGAGAAGATGGTCTTGGTATCGATCC
TCTAGAGTCGACCTGCAGGCATGCAAGCTTGGCGTAATCATGGTCATAGC
TGTTTCCTGTGTGAAATTGTTATCCGCTCACAATTCCACACAACATACGAG
CCGGAAGCATAAAGTGTAAAGCCTGGGGTGCCTAATGAGTGAGCTAACTC
ACATTAATTGCGTTGCGCTCACTGCCCGCTTTCCAGTCGGGAAA

Nt 83-265 of SEQ ID NO: 614 corresponds to compliment of nt 1-181 of the HI1064 gene.
Nt 74-406 of SEQ ID NO: 614 corresponds to nt 440-772 of the contig 178 (SEQ ID NO: 178).

GENES OF AN OTITIS MEDIA ISOLATE OF NONTYPEABLE *HAEMOPHILUS INFLUENZAE*

RELATED APPLICATIONS

The present application is a divisional of U.S. application Ser. No. 12/860,332, which is a divisional of U.S. application Ser. No. 12/646,424(U.S. Pat. No. 7,816,086), filed Dec. 23, 2009, which is a continuation of U.S. application Ser. No. 11/770,447, filed Jun. 28, 2007(U.S. Pat. No. 7,638,282), which is a continuation of U.S. application Ser. No. 10/795,159, filed Mar. 5, 2004(U.S. Pat. No. 7,241,867) which claims priority benefit from U.S. Provisional Application 60/453,134 filed Mar. 6, 2003 which is incorporated herein by reference in their entirety.

FIELD OF INVENTION

The invention relates to the polynucleotide sequence of a nontypeable strain of *Haemophilus influenzae* (NTHi) genome, NTHi genes contained within the genome and polypeptides encoded by the polynucleotides. The invention also relates to uses of these NTHi poly-nucleotides and NTHi polypeptides including vaccines and methods of treating and preventing NTHi related disorders. The invention also relates to NTHi genes which are upregulated during or in response to NTHi infection of the middle ear or nasopharynx.

BACKGROUND

Otitis media (OM) is a highly prevalent pediatric disease worldwide and is the primary cause for emergency room visits by children (Infante-Rivand and Fernandez, *Epidemiol. Rev.*, 15: 444-465, 1993). Recent statistic indicate that 24.5 million physician office visits were made for OM in 1990, representing a greater than 200% increase over those reported in the 1980's. While rarely associated with mortality any longer, the morbidity associated with OM is significant. Hearing loss is a common problem associated with this disease, often times affecting a child's behavior, education and development of language skills (Baldwin, *Am. J. Otol.*, 14: 601-604, 1993;Hunter et al., *Ann. Otol. Rhinol. Laryngol. Suppl.*, 163: 59-61, 1994; Teele et al., *J. Infect. Dis.*, 162: 685-694, 1990). The socioeconomic impact of OM is also great, with direct and indirect costs of diagnosing and managing OM exceeding $5 billion annually in the U.S. alone (Kaplan et al., *Pediatr. Infect. Dis. J.*, 16: S9-11, 1997).

Whereas antibiotic therapy is common and the surgical placement of tympanostomy tubes has been successful in terms of draining effusions, clearing infection and relieving pain associated with the accumulation of fluids in the middle ear. the emergence of multiple antibiotic-resistant bacteria and the invasive nature associated with tube placement, has illuminated the need for more effective and accepted approaches to the management and preferably, the prevention of OM. Surgical management of chronic OM involves the insertion of tympanostomy tubes through the tympanic membrane while a child is under general anesthesia. While this procedure is commonplace (prevalence rates are ~13%; Bright et al., *Am. J. Public Health*, 83(7): 1026-8, 1993) and is highly effective in terms of relieving painful symptoms by draining the middle ear of accumulated fluids, it too has met with criticism due to the invasive nature of the procedure and its incumbent risks (Berman et al., *Pediatrics*, 93(3):353-63, 1994;Bright et al., supra.; Cimons *ASM News*, 60: 527-528; Paap, *Ann. Pharmacother.*, 30(11): 1291-7, 1996).

Progress in vaccine development is most advanced for *Streptococcus pneumoniae*, the primary causative agent of acute OM (AOM), as evidenced by the recent approval and release of a seven-valent capsular-conjugate vaccine, PREVNAR® (Eskola and Kilpi, *Pedriatr. Infect. Dis. J.* 16: S72-78, 2000). While PREVNAR® has been highly efficacious for invasive pneumococcal disease, coverage for OM has been disappointing (6-8%) with reports of an increased number of OM cases due to serotypes not included in the vaccine (Black et al., *Pedriatr. Infect. Dis J.* 19: 187-195; Eskola et al., *Pedriatr. Infect. Dis J.*, 19: S72-78, 2000; Eskola et al., *N. Engl. J. Med.* 344: 403-409, 2001; Snow et al., *Otol. Neurotol.*, 23: 1-2, 2002). Less progress has been made for nontypeable *Haemophilus influenzae* (NTHi), the gram-negative pathogen that predominates in chronic OM with effusion (Klein, *Pedriatr. Infect. Dis J.*, 16: S5-8, 1997;Spinola et al., *J. Infect. Dis.*, 154: 100-109, 1986). Hampering development of effective vaccines against NTHi, is the currently incomplete understanding of the pathogenesis of NTHi-induced middle ear disease. Contributing to this delay is a lack of understanding of the dynamic interplay between microbe-expressed virulence factors and the host's immune response as the disease progresses from one of host immunological tolerance of a benign nasopharyngeal commensal, to that of an active defensive reaction to an opportunistic invader of the normally sterile middle ear space.

Currently there is a poor understanding of how NTHi causes OM in children. The identification of putative virulence factors necessary for induction of OM will contribute significantly to the understanding of the host-pathogen interaction and ultimately, the identification of potential vaccine candidates and targets of chemotherapy. There is a tremendous need to develop more effective and accepted approaches to the management and preferably, the prevention of otitis media. Vaccine development is a very promising and cost effective method to accomplish this goal (Giebank, *Pedriatr. Inject. Dis J.*, 13(11): 1064-8, 1994: Karma et al., *Int. J. Pedritr. Otorhinolaryngol.*, 32(Suppl.): S127-34, 1995).

SUMMARY OF INVENTION

The present invention provides for the identification and characterization of the genomic sequence of NTHi *H. influenzae* strain S6-028NP and the polypeptide sequences encoded thereby. The 3-fold analysis of the NTHi genomic sequence is set out in a series of contig sequences denoted am SEQ ID NO: 1-576, and the subsequent 8-fold analysis of the genomic sequence is set out in a series of 11 contig sequences denoted as SEQ ID NOS: 675-685. These contigs are raw data and one of skill in the art may assemble these contigs by comparing overlapping sequences to construct the complete genome of the NTHi stain 86-028NP using routine methods.

The present invention also provides for antibodies specific for the NTHi polypeptides of the invention. Methods of detecting NTHi bacteria in a human or in sample. such as serum, sputum, ear fluid, blood, urine, lymphatic fluid and cerebrospinal fluid are contemplated. These methods include detecting NTHi polynucleotides with specific polynucleotide probes or detecting NTHi polypeptides with specific antibodies. The invention also contemplates diagnostic kits which utilize these methods of detecting NTHi bacteria.

The present invention also contemplates methods of eliciting an immune response by administering a NTHi polypeptide of the invention or a NTHi peptide thereof. These methods include administering the NTHi polypeptide or NTHi peptide as a vaccine for treatment and/or prevention of diseases caused by NTHi infection, such as OM. The following NTHi genes are upregulated during or in response to middle ear and/or nasopharynx infections; and the polypeptides encoded by these genes and peptides thereof are contemplates as possible OM vaccine candidates and/or target of chemotherapy: hisB, lppB, sapA, lolA, rbsC, purE, ribB, arcB, uxuA, dsbB, ureH, licC, HI1647, ispZ, radC, mukF, glpR, ihfB, argR, cspD, HI0094, HI1163, HI1063, HI0665, HI1292, HI1064. NTHi hisB gene is set out as nucleotide sequence SEQ ID NO: 615 and encodes the amino acid sequence set out as SEQ ID NO: 616. NTHi sapA gene is set out as nucleotide sequence SEQ ID NO: 617 and encodes the amino acid sequence set out as SEQ ID NO: 618. NTHi rbsC gene is set out as nucleotide sequence SEQ ID NO: 619 and encodes the amino acid sequence set out as SEQ ID NO: 620. NTHi purE gene is set out as nucleotide sequence SEQ ID NO: 621 and encodes the amino acid sequence set out as SEQ ID NO: 622. NTHi ribB gene is set out as nucleotide sequence SEQ ID NO: 623 and encodes the amino acid sequence set out as SEQ ID NO: 624. NTHi arcB gene is set out as nucleotide sequence SEQ ID NO: 625 and encodes the amino acid sequence set out as SEQ ID NO: 626. NTHi uxuA gene is set out as nucleotide sequence SEQ ID NO: 627 and encodes the amino acid sequence set out as SEQ ID NO: 628. NTHi dshB gene is set out as nucleotide sequence SEQ ID NO: 629 and encodes the amino acid sequence set out as SEQ ID NO: 630. NTHi ureH gene is set out as nucleotide sequence SEQ ID NO: 631 and encodes the amino acid sequence set out as SEQ ID NO: 632. NTHi licC gene is set out as nucleotide sequence SEQ ID NO: 633 and encodes the amino acid sequence set out as SEQ ID NO: 634. NTHi HI1647 gene is set out as nucleotide sequence SEQ ID NO: 635 and encodes the amino acid sequence set out as SEQ ID NO: 636. NTHi ispZ gene is set out as nucleotide sequence SEQ ID NO: 637 and encodes the amino acid sequence set out as SEQ ID NO: 638. NTHi radC gene is set out as nucleotide sequence SEQ ID NO: 639 and encodes the amino acid sequence set out as SEQ ID NO: 640. NTHi mukF gene is set out as nucleotide sequence SEQ ID NO: 641 and encodes the amino acid sequence set out as SEQ ID NO: 642. NTHi glpR gene is set out as nucleotide sequence SEQ ID NO: 643 and encodes the amino acid sequence set out as SEQ ID NO: 644. NTHi ihfB gene is set out as nucleotide sequence SEQ ID NO: 645 and encodes the amino acid sequence set out as SEQ ID NO: 646. NTHi argR gene is set out as nucleotide sequence SEQ ID NO: 647 and encodes the amino acid sequence set out as SEQ ID NO: 648. NTHi cspD gene is set out as nucleotide sequence SEQ ID NO: 649 and encodes the amino acid sequence set out as SEQ ID NO: 650. NTHi HI1163 gene is set out as nucleotide sequence SEQ ID NO: 651 and encodes the amino acid sequence set out as SEQ ID NO: 652. NTHi HI1063 gene is set out as nucleotide sequence SEQ ID NO: 653 and encodes the amino acid sequence set out as SEQ ID NO: 654. NTHi HI0665 gene is set out as nucleotide sequence SEQ ID NO: 655 and encodes the amino acid sequence set out as SEQ ID NO: 656, NTHi HI1292 gene is set out as nucleotide sequence SEQ ID NO: 657 and encodes the am no acid sequence set out as SEQ ID NO 658.

The novel NTHi genes included in the polynucleotide sequences presented us SEQ ID NOS: 1-576, SEQ ID NOS: 675-685 and the nucleotide sequences set out in Tables 4 and 4B are also up-regulated during infection of the middle ear and/or the nasopharynx, and therefore are contemplated to encode OM vaccine candidates and/or targets of chemotherapy. In addition, the following NTHi genes are contemplated to be virulence-associated genes and therefore are contemplated to encode possible OM vaccine candidates and/or targets of chemotherapy: HI1386, HI1462, HI1369, lay, HI1598. NTHi HI1386 gene sequence is set out as SEQ ID NO: 659 and encodes the amino acid sequence set out as SEQ ID NO: 660. NTHi HI1462 gene sequence is set out as SEQ ID NO: 661 and encodes the amino acid sequence set out as SEQ ID NO: 662. NTHi HI1369 gene sequence is set out as SEQ ID NO: 665 and encodes the amino acid sequence set out as SEQ ID NO: 666. NTHi lav gene sequence is set out as SEQ ID NO: 663 and encodes the amino acid sequence set out as SEQ NO: 664. NTHi HI1598 gene sequence is set out as SEQ ID NO: 669 and SEQ ID NO: 671 and encodes the amino acid sequence set out as SEQ ID NO: 670 and SEQ ID NO: 672. Additional NTHi genes associated with virulence include the polynucleotide sequences presented as SEQ ID NO: 667 and SEQ ID NO: 673.

As a method of treating or preventing NTHi infection, the present invention contemplates administering a molecule that inhibits expression or the activity of the NTHi polypeptides, which are upregulated or active during infection. In particular, the invention contemplates methods of treating or preventing NTHi infection comprising modulating NTHi protein expression by administering an antisense oligonucleotide that specifically binds to NTHi genes that are upregulated during NTHi infections, such genes include hisB, lppB, sapA, lolA, rbsC, purE, ribB, arcB, arsbB, ureH, licC, HI1647, ispZ, racC, mukF, glpR, ihfB, argR, cspD, HI0094, HI1163, HI1063, HI0665, HI1292, HI1064. The invention also contemplates methods of treating or preventing NTHi infection comprising administering antibodies or small molecules that modulate the activity of the proteins encoded by theses genes. The novel NTHi genes included in the polynucleotide sequences presented as SEQ ID NOS: 1-576, SEQ ID NOS: 675-685 and the nucleotide sequences set out in Tables 4 and 4B are also up-regulated during infection of the middle ear and/or the nasopharynx and therefore antisense oligonucleotides that specifically bind these polynucleotide sequences are also contemplated.

Polynucleotides and Polypeptides of the Invention

The present invention provides for the sequences of the NTHi strain 86-028NP genome. This genomic sequence is presented as a series of contig sequences denoted herein as "contigs 1-576". Each contig is assigned a sequence identification number that correlates with its "contig number". Therefore, the contigs of the present invention as set out as SEQ ID NOS: 1-576. These contig polynucleotide sequences may be assembled into the complete genome sequence of the NTHi strain 86-028NP using routine methods. Upon completion of 8-fold sequence analysis of the NTHi strain 82-028NP genome, the genomic sequence was assembled into 11 contigs which are denoted herein as SEQ ID NOS: 675-685.

The present invention provides for the NTHi polynucleotide sequences and open reading frames contained within the contigs of SEQ ID NOS: 1-576, SEQ ID NOS: 675-685 and the nucleotide sequences set out in Table 3B, Table 4B and Table 5. The present invention also provides for the polypeptide sequences encoded by the NTHi polynucleotides of the present invention such as the amino acid sequences set out in Table 3B, Table 4B and Table 5. The invention provides for polynucleotides that hybridize under stringent conditions to (a) the complement of the nucleotides sequence of SEQ ID NOS: 1-576;SEQ ID NOS: 675-685 and the nucleotide sequences set out in Table 3B, Table 4B and Table 5 herein (b) a polynucleotide which is an allelic variant of any polynucleotides recited above; (c) a polynucleotide which encodes a species homolog of any of the proteins recited above; or (d) a polynucleotide that encodes a polypeptide comprising a specific domain or truncation of the NTHi polypeptides of the present invention.

The NTHi polynucleotides of the invention also include nucleotide sequences that are substantially equivalent to the polynucleotides recited above. Polynucleotides according to the invention can have, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the NTHi polynucleotides recited above.

Included within the scope of the nucleic acid sequences of the invention are nucleic acid sequence fragments that hybridize under stringent conditions to the nucleotide sequences of SEQ ID NOS: 1-576, SEQ ID NOS: 675-685 and the nucleotide sequences set out in Table 3B, Table 4B and Table 5 herein, or compliments thereof, which fragment is greater than about 5 nucleotides, preferably 7 nucleotides, more preferably greater than 9 nucleotides and most preferably greater than 17 nucleotides. Fragments of, e.g., 15, 17, or 20 nucleotides or more (hat are selective for (i.e., specifically hybridize to any one of the polynucleotides of the invention) are contemplated. Probes capable of specifically hybridizing to a polynucleotide can differentiate NTHi polynucleotide sequences of the invention from other polynucleotide sequences in the same family of genes or can differentiate NTHi genes from other bacterial genes, and are preferably based on unique nucleotide sequences.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., *Molecular Cloning: A Laboratory Manual*, $2^{nd}$ Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. ((or 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7,4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

The sequences falling within the scope of the present invention are not limited to these specific sequences, but also include allelic and species variations thereof. Allelic and species variations can be routinely determined by comparing the sequence provided in SEQ ID NOS: 1-576, SEQ ID NOS: 675-685, and nucleotide sequences out in Table 3B, Table 4B and Table 5 herein, preferably the open reading frames therein, a representative fragment thereof, or a nucleotide sequence at least 90% identical, preferably 95% identical, to the open reading frames within SEQ ID NOS: 1-576, SEQ ID NOS: 675-685 and the nucleotide sequences set out in Table 3B, Table 4B and Table 5 with a sequence from another isolate of the same species. Preferred computer program methods to determine identity and similarity between two sequences include, but are not limited to, the GCG program package, including GAP (Devereux et al., *Nucl. Acid. Res.,* 12: 387, 1984;Genetics Computer Group, University of Wisconsin, Madison, Wis.), BLASTP, BLASTN, and FASTA (Altschul et al., *J. Mol. Biol.,* 215: 403-410, 1990). The BLASTX program is publicly available from the National Center for Biotechnology Information (NCBI) and other sources (*BLAST Manual*, Altschul et al. NCB/NLM/NIH Bethesda, Md. 20894;Altschul et al., supra). The well known Smith Waterman algorithm may also be used to determine identity.

Furthermore, to accommodate codon variability, the invention includes nucleic acid molecules coding for the same amino acid sequences as do the specific open reading frames (ORF) disclosed herein. In other words, in the coding region of an ORF, substitution of one codon for another codon that encodes the same amino acid is expressly contemplated.

The isolated polypeptides of the invention include, but are not limited to, a polypeptide comprising: the amino acid sequences encoded by the nucleotide sequences included within the polynucleotide sequences set out as SEQ ID NOS: 1-576, SEQ ID NOS: 675-685 and the nucleotide sequences set out in Table 3B, Table 4B and Table 5, or the corresponding full length or mature protein. The polypeptides of the invention include the amino acid sequences of SEQ ID NO: 616, SEQ ID NO: 618, SEQ ID NO: 620, SEQ ID NO: 622. SEQ ID NO: 624, SEQ ID NO: 626, SEQ ID NO: 628, SEQ ID NO: 628, SEQ ID NO: 630, SEQ ID NO: 632, SEQ ID NO: 634, SEQ ID NO: 636, SEQ ID NO: 638, SEQ ID NO: 640, SEQ ID NO: 642, SEQ ID NO: 644, SEQ ID NO: 646, SEQ ID NO: 648, SEQ ID NO: 650, SEQ ID NO: 652, SEQ ID NO: 654, SEQ ID NO: 656, SEQ ID NO: 658, SEQ ID NO: 660, SEQ ID NO: 662. SEQ ID NO: 664, SEQ ID NO: 666, SEQ ID NO: 668, SEQ ID NO: 670, SEQ ID NO: 672, SEQ ID NO: 674, SEQ ID NO: 687, SEQ ID NO: 689, SEQ ID NO: 691, SEQ ID NO: 693, SEQ ID NO: 695, SEQ ID NO: 697, SEQ ID NO: 699, SEQ ID NO: 701, SEQ ID NO: 703, SEQ ID NO: 705, SEQ ID NO: 707, SEQ ID NO: 709, SEQ ID NO: 711, SEQ ID NO: 713, SEQ ID NO:715, SEQ ID NO: 717, SEQ ID NO: 719, SEQ ID NO: 721, SEQ ID NO:723, SEQ ID NO:725, SEQ ID NO:727, SEQ ID NO:729, SEQ ID NO: 731, SEQ ID NO: 733, SEQ ID NO: 735, SEQ ID NO: 737, SEQ ID NO: 739, SEQ ID NO: 741, SEQ ID NO: 743, SEQ ID NO: 745, SEQ ID NO: 747, SEQ ID NO: 749, SEQ ID NO: 751, SEQ ID NO: 753, SEQ ID NO: 755, SEQ ID NO: 757, SEQ ID NO: 759, SEQ ID NO: 761, 763, SEQ ID NO: 765, SEQ ID NO: 767, SEQ ID NO: 769 or SEQ ID NO: 771 which are set out in Table 3B, Table 4B and Table 5 herein.

Polypeptides of the invention also include polypeptides preferably with biological or immunogenic activity that are encoded by: (a) an open reading frame contained within the nucleotide sequences set forth as SEQ ID NOS: 1-576, SEQ ID NOS: 675-685 and the nucleotide sequences set out in Table 3B, Table 4B and Table 5, or (b) polynucleotides that hybridize to the complement of the polynucleotides of (a) under stringent hybridization conditions.

The invention also provides biologically active or immunologically active variants of the amino acid sequences of the present invention; and "substantial equivalents" thereof (e.g., with at least about 65%, at least about 70%, at least about 75%, at least about 80%, at least about 85%, 86%, 87%, 88%, 89%. at least about 90%, 91%, 92%, 93%, 94%, typically at least about 95%, 96%, 97%. more typically at least about 98%, or most typically at least about 99% amino acid identity) that retain biological and/or immunuogenic activity. Polypeptides encoded by allelic variants may have a similar, increased, or decreased activity compared to polypeptides encoded by the polynucleotides included within the nucleotide sequences presented in SEQ ID NOS: 1-576, SEQ ID NOS: 675-685 and the nucleotide sequences set out in Table 3B, Table 4B and Table 5 herein, and the polypeptides having an amino acid sequence set out in Table 3B, Table 4B and Table 5 herein NTHi peptides refer to fragments of the NTHi polypeptides encoded by the nucleotide sequences presented in SEQ ID NOS: 1-576, SEQ ID NOS: 675-685 or the nucleotide sequences set out in Table 3B. Table 4B and Table 5 herein, and the polypeptides having the amino acid sequences set out in Table 3B, Table 4B and Table 5 herein. The preferred NTHi peptides are biologically and/or immunologically active.

The present invention further provides isolated NTHi polypeptides or NTHi peptides encoded by the NTHi nucleic acid fragments of the present invention or by degenerate variants of the nucleic acid fragments of the present invention. The term "degenerate variant" refers to nucleotide fragments which differ from a nucleic acid fragment of the present invention (e.g., an ORF) by nucleotide sequence but, due to the degeneracy of the genetic code, encode an identical NTHi polypeptide sequence. Preferred nucleic acid fragments of the present invention are the ORFs that encode proteins.

The invention also provides for NTHi polypeptides with one or more conservative amino acid substitutions that do not affect the biological and/or immunogenic activity of the polypeptide. Alternatively, the NTHi polypeptides of the invention are contemplated to have conservative amino acids substitutions which may or may not alter biological activity. The term "conservative amino acid substitution" refers to a substitution of a native amino acid residue with a nonnative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "alanine scanning mutagenesis". Naturally occurring amino acids are characterized based on their side chains as follows: basic: arginine, lysine, histidine; acidic; glutamic acid, aspartic acid; uncharged polar; glutamine, asparagine, serine, threonine, tyrosine; and non-polar; phenylalanine, tryptophan, cysteine, glycine, alanine, valine, proline, methionine, leucine, norleucine, isoleucine. General rules for amino acid substitutions are set forth in Table 1 below.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |

TABLE 1-continued

Amino Acid Substitutions

| Original Residues | Exemplary Substitutions | Preferred Substitutions |
|---|---|---|
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

Antisense polynucleotides complementary to the polynucleotides encoding the NTHi polypeptides are also provided.

The invention contemplates that polynucleotides of the invention may be inserted in a vector for amplification or expression. For expression, the polynucleotides are operatively linked to appropriate expression control sequence such as a promoter and polyadenylation signal sequences. Further provided are cells comprising polynucleotides of the invention. Exemplary prokaryotic hosts include bacteria such as *E. coli, Streptomyces, Pseudomonas, Salmonella* and *Serratia*.

The term "isolated" refers to a substance removed from, and essentially free of, the other components of the environment in which it naturally exists. For example, a polypeptide is separated from other cellular proteins or a DNA is separated from other DNA flanking it in a genome in which it naturally occurs.

Antibodies and Methods for Eliciting an Immune Response

The invention provides antibodies which bind to antigenic epitopes unique to (i.e., are specific for) NTHi polypeptides. Also provided are antibodies which bind to antigenic epitopes common among multiple *H. influenzae* subtypes but unique with respect to any other antigenic epitopes. The antibodies may be polyclonal antibodies, monoclonal antibodies, antibody fragments which retain their ability to bind their unique epitope (e.g., Fv, Fab and F(ab)2 fragments), single chain antibodies and human or humanized antibodies. Antibodies may be generated by techniques standard in the art.

It is known in the art that antibodies to the capsular polysaccharide of *H. influenzae* exhibit the ability to kill bacteria in vitro assays. These antibodies are also known to protect against challenge with *H. influenzae* in animal model systems. These studies indicate antibody to the capsular polysaccharrides are likely to elicit a protective immune response in humans. The present invention provides for antibodies specific for the NTHi polypeptides of the present invention and fragments thereof, which exhibit the ability to kill both *H. influenzae* bacteria and to protect humans from NTHi infection. The present invention also provides for antibodies specific for the NTHi polypeptides of the invention which reduce the virulence, inhibit adherence, inhibit cell division, and/or inhibit penetration into the epithelium of *H. influenzae* bacteria or enhance phagocytosis of the *H. influenzae* bacteria.

In vitro complement mediated bactericidal assay systems (Musher et al., *Infect. Immun.* 39: 297-304, 1983; Anderson et al., *J. Clin. Invest.* 51: 31-38, 1972) may be used to measure the bactericidal activity of anti-NTHi antibodies. Further data on the ability of NTHi polypeptides and NTHi peptides to elicit a protective antibody response may be generated by using models of infection such as the chinchilla model system described herein.

It is also possible to confer short-term protection to a host by passive immunotherapy via the administration of preformed antibody against an epitope of NTHi, such as antibodies against NTHi OMP, LOS or noncapsular proteins. Thus, the contemplated vaccine formulations can be used to produce antibodies for use in passive immunotherapy. Human immunoglobulin is preferred in human medicine because a heterologous immunoglobulin may provoke an immune response to its foreign immunogenic components. Such passive immunization could be used on an emergency basis for immediate protection of unimmunized individuals exposed to special risks. Alternatively, these antibodies can be used in the production of anti-idiotypic antibody, which in turn can be used as an antigen to stimulate an immune response against NTHi epitopes.

The invention contemplates methods of eliciting an immune response to NTHi in an individual. These methods include immune responses which kill the NTHi bacteria and immune responses which block *H. influenzae* attachment to cells. In one embodiment, the methods comprise a step of administering an immunogenic dose of a composition comprising a NTHi protein or NTHi peptide of the invention. In another embodiment, the methods comprise administering an immunogenic dose of a composition comprising a cell expressing a NTHi protein or NTHi peptide of the invention. In yet another embodiment, the methods comprise administering an immunogenic dose of a composition comprising a polynucleotide encoding a NTHi protein or NTHi peptide of the invention. The polynucleotide may be a naked polynucleotide not associated with any other nucleic acid or may be in a vector such as a plasmid or viral vector (e.g., adeno-associated virus vector or adenovirus vector). Administration of the compositions may be by routes standard in the art, for example, parenteral, intravenous, oral, buccal, nasal, pulmonary, rectal, or vaginal. The methods may be used in combination in a single individual. The methods may be used prior or subsequent to NTHi infection of an individual.

An "immunological dose" is a dose which is adequate to produce antibody and/or T cell immune response to protect said individual from NTHi infection, particularly NTHi infection of the middle ear and/or the nasopharynx or lower airway. Also provided are methods whereby such immunological response slows bacterial replication. A further aspect of the invention relates to an immunological composition which, when introduced into an individual capable or having induced within it an immunological response. The immunological response may be used therapeutically or prophylactically and may take the form of antibody immunity or cellular immunity such as that arising from CTL or CD4+ T cells. A NTHi protein or an antigenic peptide thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the NTHi polypeptides encoded by the polynucleotide of the invention or antigenic peptides thereof.

The invention correspondingly provides compositions suitable for eliciting an immune response to NTHi infection, wherein the antibodies elicited block binding of NTHi bacterium to the host's cells. The compositions comprise NTHi proteins or NTHi peptides of the invention, cells expressing the NTHi polypeptide, or polynucleotides encoding the polypeptides. The compositions may also comprise other ingredients such as carriers and adjuvants.

Genes that are up-regulated in NTHi infection of the middle ear and/or the nasopharynx and genes that are associated with NTHi virulence are described herein. The polypeptides and peptides thereof which are encoded by these NTHi genes are contemplated to be useful for eliciting an immune response for treating or preventing disorders associated with NTHi infection, such as OM. Some of the polypeptides encoded by these genes include: histidine biosynthesis protein, lipoprotein B, peptide ABC transporter, periplasmic SapA precursor, outer membrane lipoproteins carrier protein precursor, ribose transport system permease protein, phosphoribosylaminoimidazole carboxylase catalytic subunit, PurE, Phosphoribosylaminoimidazole carboxylase catalytic subunit, ornithine carbamolytransferase, mannonate dehydratase, disulfide oxidoreductase, urease accessory protein, phospshocholine cytidylytransferase, putative pyridoxine biosynthesis protein, singlet oxygen resistance protein, intracellular septation protein, DNA repair protein, MukF protein, glycerol-3-phosphate regulon repressor, integration host factor beta subunit, arginine repressor, cold shock like protein, stress response protein, LicA, MukF, RadA and those hypothetical proteins encoded by HI10094, HI1163, HI0665, HI1292, HI1064 HI186, HI0352 genes. NTHi OMPs, LOS and noncapsular proteins are also contemplated to elicit an immune response for prevention and treatment of disorders associated with NTHi infection.

An "immunogenic dose" of a composition of the invention is one that generates, after administration, a detectable humoral and/or cellular immune response in comparison to the immune response detectable before administration or in comparison to a standard immune response before administration. The invention contemplates that the immune response resulting from the methods may be protective and/or therapeutic.

The invention includes methods of blocking binding of NTHi bacteria to host cells in an individual. The methods comprise administering antibodies or polypeptides of the invention that block binding of NTHi cellular attachment. Alternatively, administration of one or more small molecules that block binding of NTHi cell attachment is contemplated. In vitro assays may be used to demonstrate the ability of an antibody, polypeptide or small molecule of the invention to block NTHi cell attachment.

Pharmaceutical compositions comprising antibodies of the invention, polypeptides of the invention and/or small molecules of the invention that block NTHi cellular attachment are provided. The pharmaceutical compositions may consist of one of the foregoing active ingredients alone, may comprise combinations of the foregoing active ingredients or may comprise additional active ingredients used to treat bacterial infections. The pharmaceutical compositions may comprise one or more additional ingredients such as pharmaceutically effective carriers. Dosage and frequency of the administration of the pharmaceutical compositions are determined by standard techniques and depend, for example, on the weight and age of the individual, the route of administration, and the severity of symptoms. Administration of the pharmaceutical compositions may be by routes standard in the art, for example, parenteral, intravenous, oral, buccal, nasal, pulmonary, rectal, or vaginal.

Also provided by the invention are methods for detecting NTHi infection in an individual. In one embodiment, the methods comprise detecting NTHi polynucleotides of the invention in a sample using primers or probes that specifically bind to the polynucleotides. Detection of the polynucleotide may be accomplished by numerous techniques routine in the art involving, for example, hybridization and PCR.

The antibodies of the present invention may also be used to provide reagents for use in diagnostic assays for the detection of NTHi antigens (NTHi polypeptides and peptides thereof) in various body fluids of individuals suspected of influenzae infection. In another embodiment, the NTHi proteins and peptides of the present invention may be used as antigens in immunoassays for the detection of NTHi in various patient tissues and body fluids including, but not limited to: blood, serum, ear fluid, spinal fluid, sputum, urine, lymphatic fluid and cerebrospinal fluid. The antigens of the present invention may be used in any immunoassay system known in the art including, but not limited to: radioimmunoassays. ELISA assays, sandwich assays, precipitin reactions, gel diffusion precipitin reactions, immunodiffusion assays, agglutination assays, fluorescent immunoassays, protein A immunoassays and immunoelectrophoresis assays.

Vaccines and Chemotherapeutic Targets

An aspect of the invention relates to a method for inducing an immunological response in an individual, particularly a mammal which comprises inoculating the individual with a NTHi antigen protein or an antigenic peptide thereof.

The present invention also provides for vaccine formulations which comprise an immunogenic recombinant NTHi protein or NTHi peptide of the invention together with a suitable carrier. The NTHi polypeptides and peptides thereof contemplated as vaccine candidates and/or targets of chemotherapy include, but are not limited to, histidine biosynthesis protein, lipoprotein B, peptide ABC transporter, periplasmic SapA precursor, outer membrane lipoproteins carrier protein precursor, ribose transport system permease protein, phosphoribosylaminoimidazole carboxylase catalytic subunit. PurE, 3,4-dihydroxt-2-butone 4-phosphate synthase, ornithine carbamolytransferase, mannonate dehydratase, disulfide oxidoreductase, urease accessory protein, phospshocholine cytidylytransferase, putative pyridoxine biosynthesis protein, singlet oxygen resistance protein, intracellular septation protein, DNA repair protein, MUKF protein, glycerol-3-phosphate regulon repressor, integration host factor beta subunit, arginine repressor, cold shock like protein, stress response protein, LicA, RadA and those hypothetical proteins encoded by HI0094, HI1163, HI0665, HI1292, HI1064 HI1386, HI0352 genes, NTHi OMPs, NTHi LOS and NTHi noncapsular proteins and polypeptides encoded by the novel NTHi polynucleotide sequences present in the nucleotide sequences set out as SEQ ID NOS: 1-576, SEQ ID NOS: 675-685 and the nucleotide sequences set out in Table 3B, Table 4B and Table 5 herein, and the polypeptides having the amino acid sequences set out in Table 3B, Table 4B and Table 5 herein.

Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

A. Peptide Vaccines

Peptide therapeutic agents, such as peptide vaccines, are well known in the art and are of increasing use in the pharmaceutical arts. Consistent drawbacks to the parenteral administration of such peptide compounds have been the rapidity of breakdown or denaturation. Infusion pumps, as well as wax or oil implants, have been employed for chronic administration of therapeutic agents in an effort to both prolong the presence of peptide-like therapeutic agents and preserve the integrity of such agents. Furthermore, the peptide-like agent should (with particular reference to each epitope of the peptide-like agent) ideally maintain native state configuration for an extended period of time and additionally be presented in a fashion suitable for triggering an immunogenic response in the challenged animal or immunized human.

The NTHi antigenic peptides of the invention can be prepared in a number of conventional ways. The short peptides sequences can be prepared by chemical synthesis using standard means. Particularly convenient are solid phase techniques (see, e.g., Erikson et al., *The Proteins* (1976) v. 2, Academic Press, New York, p. 255). Automated solid phase synthesizers are commercially available. In addition, modifications in the sequence are easily made by substitution, addition or omission of appropriate residues. For example, a cysteine residue may be added at the carboxy terminus to provide a sulfhydryl group for convenient linkage to a carrier protein, or spacer elements, such as an additional glycine residue, may be incorporated into the sequence between the linking amino acid at the C-terminus and the remainder of the peptide. The short NTHi peptides can also be produced by recombinant techniques. The coding sequence for peptides of this length can easily be synthesized by chemical techniques, e.g., the phosphotriester method described in Matteucci et al., *J Am Chem Soc.*, 103: 3185 (1981).

Some of the NTHi peptide sequences contemplated herein may be considered too small to be immunogenic, they may be linked to carrier substances in order to confer this property upon them. Any method of creating such linkages known in the art may be used. Linkages can be formed with heterobifunctional agents that generate a disulfide link at one functional group end and a peptide link at the other, such as a disulfide amide forming agent, e.g., N-succidimidyl-3-(2-pyridyldithio) proprionate (SPDP) (See, e.g., Jansen et al., *Immun. Rev.* 62:185, 1982) and bifunctional coupling agents that form a thioether rather than a disulfide linkage such as reactive esters of 6-maleimidocaproic acid, 2-bromoacetic acid, 2-iodoacetic acid, 4-(N-maleimido-methyl) cyclohexane-1-carboxylic acid and the like, and coupling agent which activate carboxyl groups by combining them with succinimide or 1-hydroxy-2-nitro-4-sulfonic acid, for sodium salt such as succinimmidyl 4-(N-maleimido-methyl) cyclohexane-1-carboxylate (SMCC).

B. Vaccine Compositions and Administration

A priming dose or the immunogen that is followed by one or more booster exposures to the immunogen may be necessary to be an effective vaccine (Kramp et al., *Inject. Immun.*, 25: 771-773, 1979;Davis et el., *Immunology Letters*, 14: 341-8 1986 1987). Examples of proteins or polypeptides that could beneficially enhance the immune response if co-administered include cytokines (e.g., IL-2, IL-12, GM-CSF). cytokine-inducing molecules (e.g. Leaf) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-$\beta$) may be beneficial in certain diseases.

Ideally, an immunogen will exhibit two properties; the capacity to stimulate the formation of the corresponding antibodies and the propensity to react specifically with these antibodies. Immunogens bear one or more epitopes which are the smallest part of an immunogen recognizable by the combing site of an antibody. In particular instances, immunogen, fractions of immunogens or conditions under which the immunogen is presented are inadequate to precipitate the desired immunological response resulting in insufficient immunity. This is often the case with peptides or other small molecules used as immunogens. Other substances such as immunomodulators (e.g., cytokines such as the interleukins) may be combined in vaccines as well.

The vaccine art recognizes the use of certain substances called adjuvants to potentate an immune response when used in conjunction with an immunogen. Adjuvants are further used to elicit an immune response that is faster or greater than would be elicited without the use of the adjuvant. In addition, adjuvants may be used to create an immunological response using less immunogen than would be needed without the inclusion of adjuvant, to increase production of certain antibody subclasses that afford immunological protection or to enhance components of the immune response (e.g., humoral, cellular). Known adjuvants include emulsions such as Freund's Adjuvants and other oil emulsions. *Bordetella pertussis*, NIF59, purified saponin from *Quillaja saponaria* (QS21), aluminum salts such as hydroxide, phosphate and alum. calcium phosphate, (and other metal salts), gels such as aluminum hydroxide salts, mycobacterial products including muramyl dipeptides, solid materials, particles such as liposomes and virosomes. Examples of natural and bacterial products known to be used as adjuvants include monophosphoryl lipid A (MPL), RC-529 (synthetic MPL-like acylated monosaccharide), OM-174 which is a lipid A derivative from *E. coli*, holotoxins such as cholera toxin (CT) or one of its derivatives, pertussis toxin (PT) and heat-labile toxin (LT) of *E. coli* or one of its derivatives, and CpG oligonucleotides. Adjuvant activity can be affected by a number of factors, such as carrier effect, depot formation, altered lymphocyte recirculation, stimulation of T-lymphocytes, direct stimulation of B-lymphocytes and stimulation of macrophages.

Vaccines are typically prepared as injectables, either as liquid solutions or suspensions; solid forms suitable for solution in. or suspension in, liquid prior to injection may also be prepared. The preparation may also be emulsified. The active immunogenic ingredient is often mixed with excipients, which are pharmaceutically acceptable and compatible with the active ingredient. Suitable excipients are, e.g., water, saline, dextrose, glycerol, ethanol, or the like and combinations thereof. In addition, if desired, the vaccine may contain minor amounts of auxiliary substances such as wetting or emulsifying agents, pH buffering agents, or adjuvants, which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be folioed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%-95% of active ingredient, preferably 25-70%.

Vaccines may also be administered through transdermal routes utilizing jet injectors, microneedles, electroporation, sonoporation, microencapsulation, polymers or liposomes, transmucosal routes and intranasal routes using nebulizers, aerosols and nasal sprays. Microencapsulation using natural or synthetic polymers such as starch, alginate and chitosan, D-poly L-lactate (PLA), D-poly DL-lactic-coglycolic microspheres, polycaprolactones, polyorthoesters, polyanhydrides and polyphosphazenes polyphosphatazanes are useful for both transdermal and transmucosal administration. Polymeric complexes comprising synthetic poly-ornithate, poly-lysine and poly-arginine or amphipathic peptides are useful for transdermal delivery systems. In addition, due to their amphipathic nature, liposomes are contemplated for transdermal, transmucosal and intranasal vaccine delivery systems. Common lipids used for vaccine delivery include N-(1)2,3-(dioleyl-dihydroxypropyl)-N,N,N,-trimethylammonium-methyl sulfate (DOTAP), dioleyloxy-propyl-trimethylammonium chloride DOTMA, dimystyloxypropyl-3-dimethyl-hydroxyethyl ammonium (DMRIE), dimethyldioctadecyl ammonium bromide (DDAB) and 9N(N',N-dimethylamino-ethane)carbamoyl)cholesterol (DC-Chol). The combination of helper lipids and liposomes will enhance up-take of the liposomes through the skin. These helper lipids include, dioleoyl phosphatidylethanolamine (DOPE), dilauroylphosphatidylethanolamine (DLPE), dimyristoyl phosphatidylethanolamine (DMPE), dipalmitoylphosphatidylethanolamine (DPPE). In addition, triterpenoid glycosides or saponins derived from the Chilean soap tree bark (*Quillaja saponaria*) and chitosan (deacetylated chitan) have been contemplated as useful adjuvants for intranasal and transmucosal vaccine delivery.

The proteins may be formulated into the vaccine as neutral or salt forms. Pharmaceutically acceptable salts, include the acid addition salts (formed with the free amino groups of the peptide) and which are formed with inorganic acids such as, e.g., hydrochloric or phosphoric acids, or such organic acids as acetic, oxalic, tartaric, mandelic. Salts formed with the free carboxyl groups may also be derived From inorganic bases such as, e.g., sodium, potassium, ammonium, calcium, or ferric hydroxides, and such organic bases as isopropylamine, trimethylamine, 2-ethylamino ethanol, histidine, and procaine.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in one or three month intervals by a subsequent injection or other administration.

Upon immunization with a vaccine composition as described herein, the immune system of the host responds to the vaccine by producing large amounts of CTLs specific for the desired antigen, and the host becomes at least partially immune to later infection, or resistant to developing chronic infection. Vaccine compositions containing the NTHi polypeptide or NTHi peptides of the invention are administered to a patient susceptible to or otherwise at risk of bacterial infection to elicit an immune response against the antigen and thus enhance the patient's own immune response capabilities. Such an amount is defined to be an "immunogenically effective dose." In this use, the precise amounts again depend on the patient's state of health and weight, the mode of administration, the nature of the formulation, etc., but generally range from about 1.0 µg to about 5000 per 70 kilogram patient, more commonly from about 10 to about 500 mg per 70 kg of body weight. For therapeutic or immunization purposes, the NTHi polypeptide or NTHi peptides of the invention can also be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a noninfected host, the recombinant vaccinia virus expresses the immunogenic peptide, and thereby elicits a host CTL response.

Humoral immune response may be measured by many well known methods, such as Single Radial Immunodiffusion Assay (SRID), Enzyme Immunoassay (EIA) and Hemagglutination Inhibition Assay (HAI). In particular, SRID utilizes a layer of a gel, such as agarose, containing the immunogen being tested. A well is cut in the gel and the serum being tested is placed in the well. Diffusion of the antibody out into the gel leads to the formation of a precipitation ring whose area is proportional to the concentration of the antibody in the serum being tested. EIA, also known as ELISA (Enzyme Linked Immunoassay), is used to determine total antibodies in the sample. The immunogen is adsorbed to the surface of microtiter plate. The test serum is exposed to the plate followed by an enzyme linked immunoglobulin, such as IgG. The enzyme activity adherent to the plate is quantified by any convenient means such as spectrophotometry and is proportional to the concentration of antibody directed against the immunogen present in the test sample. HAI utilizes the capability of an immunogen such as viral proteins to agglutinate chicken red blood cells (or the like). The assay detects neutralizing antibodies, i.e., those antibodies able to inhibit hemagglutination. Dilution of the test serum are incubated with a standard concentration of immunogen, followed by the addition of the red blood cells. The presence of neutralizing antibodies will inhibit the agglutination of the red blood cells by the immunogen. Tests to measure cellular immune response include determination of delayed-type hypersensitivity or measuring the proliferative response of lymphocytes to target immunogen.

Nontypeable *Haemophilus influenzae* (NTHi)

*H. influenzae* is a small, nonmotile gram negative bacterium. Unlike other *H. influenzae* strains, the nontypeable *H. influenzae* (NTHi) strains lack a polysaccharide capsule and are sometimes denoted as "nonencapsulated." NTHi strains are genetically distinct from encapsulated strains and are more heterogenous than the type b *H. influenzae* isolates. NTHi presents a complex array of antigens to the human host. Possible antigens that may elicit protection include OMPs, lipopolysaccharides, lipoproteins, adhesion proteins and noncapsular proteins.

Humans are the only host for *H. influenze*. NTHi strains commonly reside in the upper respiratory tract including the nasopharynx and the posterior oropharynx, the lower respiratory tract and the female genital tract. NTHi causes a broad spectrum of diseases in humans, including but not limited to, otitis media, pneumonia, sinusitis, septicemia, endocarditis, epiglottitis, septic arthritis, meningitis, postpartum and neonatal infections, postpartum and neonatal sepsis, acute and chromic salpingitis, epiglottis, pericarditis, cellulitis, osteomyelitis, endocarditis, cholecystitis, intraabdominal infections, urinary tract infection, mastoiditis, aortic graft infection, conjunctitivitis, Brazilian purpuric fever, occult bacteremia and exacerbation of underlying lung diseases such as chronic bronchitis, bronchietasis and cystic fibrosis.

Epidemiologic studies of NTHi have indicated that the strains are heterogeneous with respect to outer membrane protein profiles (Barenkamp et al., *Infect. Immun.* 36: 535-40, 1982), enzyme allotypes (Musser et al., *Infect. Immun.,* 52: 183-191, 1986). and other commonly used epidemiologic tools. There have been several attempts to subtype NTHi, but none of the methodologies have been totally satisfactory. The outer-membrane protein composition of NTHi consists of approximately 20 proteins. All NTHi strains contains two common OMP's with molecular weights of 30,000 and 16,600 daltons. NTHi strains may be subtyped based on two OMP's within the 32,000-42,000 dalton range. The NTHi liposaccharide profile is fundamentally different than the enteric gram negative bacteria and separates into 1-4 distinct bands ranging from less than 20,000 daltons.

A prototype NTHi isolate is the low passage isolate 86-028NP which was recovered from a child with chronic otitis media. This strain has been well characterized in vitro (Bakaletz et al., *Infect. Immun.,* 53: 331-5, 1988;Holmes et al., *Microb. Pathog.,* 23: 157-66, 1997) as well as in the chinchilla OM model (described herein) (Bakaletz et al., *Vaccine,* 15: 955-61, 1997;Suzuki et al., *Infect. Immun.,* 62: 1710-8, 1994: DeMaria et al., *Infect. Immun.,* 64: 5187-92, 1996). The 86-028NP strain was used, as described herein, to identify genes that are up-regulated in expression in the chinchilla model of otitis media and genes that are necessary for NTHi survival in the chinchilla middle ear.

DFI Strategy

A differential fluorescence induction (DFI) strategy was used herein to identify NTHi genes induced during OM in a chinchilla animal model. Several methods have been developed to identify bacterial genes that contribute to the virulence of an organism during infection. Such methods include in vivo expression technology (IVET) in which bacterial promoters regulate the expression of gene(s) required for synthesis of essential nutrients required for survival in the host; signature-tagged mutagenesis (STM) enabling tag-specific identification of genes that alter the virulence properties of a microorganism when mutated; DNA microarray technology to globally screen for transcriptionally active genes, and DFI which uses Fluorescent Activated Cell Sorting (FACS) FACS analysis to select for transcriptionally active promoters (Chiang et al., *Annu. Rev. Microbiol.*, 53: 129-154, 1999). DFI is a high-throughput method that allows for the identification of differentially regulated genes regardless of the basal level of expression and does not exclude those that are essential for growth in vitro.

DFI has been successfully utilized in many microorganisms. For example, a Green Fluorescent Protein (GFP) GFP reporter system and flow cytometry was used to study mycobacterial gene expression upon interaction with macrophages (Dhandayuthapani et al., Mol. Microbiol., 17: 901-912, 1995). A promoter trap system was used to identify genes whose transcription was increased when Salmonellae were subjected to environments simulating in vivo growth and when internalized by cultured macrophage-like cells (Valdivia and Falkow, Mol. Microbiol., 22: 367-378, 1996; Valdivia and Falkow, Science, 277: 2007-2011, 1997; Valdivia and Falkow, Curr. Opin. Microbiol., 1: 359-363, 1998). In addition, DFI has been used to identify promoters expressed in S. pneumoniae and S. aureus when grown under varied in vitro conditions simulating infection (Marra et al., Infect. Immun., 148: 1483-1491, 2002 70(3): 1422-1433, 2002; Schneider et al., Proc. Natl. Acad. Sci. U.S.A., 97: 1671-1676, 2000). In addition, DFI has been utilized to study gene regulation in Bacillus cereus in response to environmental stimuli (Dunn and Handelsman, Gene, 226: 297-305, 1999), in S. pneumoniae in response to a competence stimulatory peptide (Bartilson et al., Mol. Microbiol., 39: 126-135, 2001), and upon interaction with and invasion of host cells in Bartonella henselae Lee and Falkow, Infect. Immun., 66: 3964-3967, 1998), Listeria monocytogenes Wilson et al., Infect. Immun., 69: 5016-5024, 2001), Brucella abortus(Eskra et al., Infect. Immun., 69: 7736-7742, 2001), and Escherichia coli(Badger et al., Mol. Microbiol., 36: 174-182, 2000).

Whereas DFI has been successfully used to identify promoters active in cell culture models of infection or in vitro conditions designed to simulate an in vivo environment, few have applied DFI to identify promoters regulated in a specific biological niche within the whole animal. This is likely due to the numerous challenges associated with sorting from an in vivo environment. The host inflammatory response, dissemination and/or clearance of bacterial cells from the site of infection, as well as adherence of bacteria to epithelial cells, possibly via biofilm formation, can make bacteria inaccessible for retrieval from the living animal. These factors, among others, contribute to the complexity of the microenvironment and the heterogeneity of gene expression as the bacteria sense and respond to these changes. Recently, DFI has been used to identify promoters expressed in S. pneumoniae when the bacteria were screened in a mouse model of respiratory tract infection and a gerbil infection model of OM (Marra et al., Infect. Immun. 70: 1422-33, 2002;Marra et al., Microbiol., 148: 1483-91, 2002).

Animal Model

The chinchilla model is a widely accepted experimental model for OM. In particular, a chinchilla model of NTHi-induced OM has been well characterized (Bakaletz et al., J. Infect. Dis., 168: 865-872, 1993;Bakaletz and Holmes, Clin. Diagn. Lab. Immunol., 4: 223-225, 1997;Suzuki and Bakaletz, Infect. Immun., 62: 1710-1718, 1994), and has been used to determine the protective efficacy of several NTHi outer membrane proteins, combinations of outer membrane proteins, chimeric synthetic peptide vaccine components, and adjuvant formulations as vaccinogens against OM (Bakaletz et al, Vaccine, 15: 955-961, 1997;Bakaletz et al., Infect. Immun., 67: 2746-2762, 1999;Kennedy et al., Infect. Immun., 68: 2756-2765, 2000).

In particular, there is an unique in vivo model wherein adenovirus predisposes chinchillas to H. influenzae-induced otitis media, which allowed for the establishment of relevant cell, tissue and organ culture systems for the biological assessment of NTHi (Bakaletz et al., J. Infect. Dis., 168: 865-72, 1993;Suzuki et al., Infect Immunity 62: 1710-8, 1994). Adenovirus infection alone has been used to assess for the transudation of induced serum antibodies into the tympanum (Bakaletz et al., Clin. Diagnostic Lab Immunol., 4(2): 223-5, 1997) and has been used as a co-pathogen with NTHi, to determine the protective efficacy of several active and passive immunization regimens targeting various NTHi outer membrane proteins, combinations of OMPs, chimeric synthetic peptide vaccine components, and adjuvant formulations as vaccinogens against otitis media (Bakaletz et al., Infect Immunity, 67(6): 2746-62, 1999;Kennedy et al., Infect Immun., 68(5): 2756-65, 2000;Novotny et al., Infect Immunity 68(4): 2119-28, 2000;Poolman et al., Vaccine 19 (Suppl. 1): S108-15, 2000).

Genes Upregulated In Vivo in Response to NTHi Infection of the Middle Ear

In order to identify differentially regulated promoters in response to NTHi infection of the middle ear, a promoter trap library was constructed and sorting parameters defined. A portion of the promoter trap library was inoculated directly into the chinchilla middle ear and OM development was monitored by video otoscopy and tympanometry at 24 and 48 hours. In addition, the middle ear fluids were recovered 24 and 48 hours after infection. Two-color FACS analysis was used to isolated bacteria that were expressing GFP from other cells and debris associated with the effusion. Following isolation, DNA sequence of the Haemophilus inserts 5' of the gfpmut3 gene were determined and analyzed. In this manner, we identified genes that are up-regulated as NTHi sense and respond to the environment of the chinchilla middle car during AOM. The following genes were identified and due to their up-regulation during NTHi infection, they may play a role in NTHi infection and virulence.

As described below in Example 7, following the DFI procedure described above and subsequent FACS analysis of gfp-expressing clones, 52 candidate clones containing potential in vivo-regulated promoters were isolated. The genes these clones control were categorized based upon general description and function within the cell and include general metabolic processes, environmental informational processing and membrane transport, membrane proteins and hypothetical proteins. Eight of these 52 clones contain sequences that are unique to NTHi strain 86-028NP. Importantly, 3 clones were isolated from independent screens in more than one animal thereby verifying the method of isolation.

In order to independently confirm the FACS data, we determined the relative expression of candidate genes by quantitative Reverse Transcriptase-Polymerase Chain Reaction (RT-PCR) RT-PCR. The parent strain 86-028NP, was used for these studies. Thus, wild-type gene expression without the influence of plasmid copy number on gene regulation was analyzed, allowing for the indication of false-positive clone identification by FACS. Of the 44 candidate clones containing sequence similar to that identified in H. influenzae strain Rd, quantitative comparison of gene expression in vitro and in vivo confirmed up-regulated gene expression for twenty-six genes (60%) when NTHi respond to environmental cues present in the chinchilla middle ear. This analysis identified in vivo-regulated promoters which drive expression of genes involved in membrane transport, environmental informational processing, cellular metabolism, gene regulation, as well as hypothetical proteins with unknown function. (See Table 4 in Example 6).

Quantitative RT-PCR demonstrated a two-fold increase in lolA expression, enabling lipoprotein transport from the inner membrane to the outer membrane. Bacteria grow rapidly in the middle ear environment reaching $5.0 \times 10^8$ CFU NTHi ml middle ear fluid within 48 hours. The bacteria sense and respond to the environment, acquiring or synthesizing the necessary nutrients for growth and survival. The gene encoding the membrane component in ribose sugar transport, rbsC (SEQ ID NO: 619), showed a 5-fold increase in expression in vivo compared to cells growing vitro. In addition, many genes involved in metabolic processes show a dramatic increase in gene expression in vivo compared to cells growing in vitro. These include a riboflavin synthesis gene, ribB (SEQ ID NO: 623), a purine nucleotide biosynthetic gene purE (SEQ ID NO: 621), omithine carbamoyltransferase, arcB (SEQ ID NO: 625). involved in arginine degradation via the urea cycle and uxuA (SEQ ID NO: 627), encoding mannonate hydrolase, required for the uptake of D-glucuronate and transformation into glyceraldehyde 3-phosphate. In addition, but to a lesser degree, genes for histidine biosynthesis (hisB; SEQ ID NO: 615), DNA repair (radC: SEQ ID NO: 639) and a putative intracellular septation transmembrane protein (ispZ; SEQ ID NO: 637) were up-regulated.

Disulfide bond formation is important for folding and assembly of many secreted proteins in bacteria. In prokaryotes, DsbA and DsbB make up the oxidative pathway responsible for the formation of disulfides. DsbB reoxidizes DsbA, which donates disulfide bonds directly to unfolded polypeptides, and DsbB has been demonstrated to generate disulfides de novo from oxidized quinones (Collet and Bardwell, *Mol. Microbiol.*, 44: 1-8, 2002). In *H. influenzae* strain Rd, DsbA is required for competence for transformation (Tomb, *Proc. Natl. Acad. Sci. U.S.A.*, 89: 10252-10256, 1992). Herein, an approximate 3-fold increase in dsbB gene (SEQ ID NO: 629) transcription was demonstrated, illuminating an important role for disulfide interchange for NTHi growing in the middle ear environment.

Bacteria colonization of the middle ear, a normally sterile environment, results in a host inflammatory response and subsequent neutrophil infiltration. Bacteria have evolved numerous strategies to combat this host response. NTHi increase gene expression (4-fold) of ureH (SEQ ID NO:631), a homologue of a gene required for expression of active urease in *Helicobacter*, shown to be involved in acid tolerance (Young et al., *J. Bacterol.*, 178: 6487-6495, 1996). Recently, it has been reported that urease activity may play a role in chronic *Actinobacillus pleuropneumoniae* infection by counteracting the decrease in pH occurring upon infection (Baltes et al., *Infect. Immun.*, 69: 472-478, 2000: Baltes et al., *Infect. Immun.*, 69: 472-478, 2001;Bosse and Machines, *Can. J. Vet. Res.*, 04: 145-150). A biotype analysis on NTHi isolates from middle ear effusions demonstrated that 87% are urease positive (DeMaria et al., *J. Clin. Microbiol.*, 20: 1102-1104, 1984). However, the role of urease in NTHi virulence is unknown. Similarly, an increase in expression of a gene whose product demonstrates 88% sequence identity to a pyridoxine biosynthesis protein in *S. pneumoniae* and 60% homology to a putative singlet oxygen resistance protein that may function as an antioxidant. Phosphorylcholine (ChoP) has been implicated in the pathogenesis of NTHi (Weiser et al., *Infect. Immun.*, 65: 943-950, 1997), NTHi modulates ChoP expression by phase variation, decorating the LOS on the cell surface. ChoP may contribute to NTHi persistence in the respiratory tract via decreased susceptibility to antimicrobial peptides (Lysecko et al., *Infect. Immun.*, 68: 1664-1671. 2000) and alter the sensitivity to serum killing mediated by C-reactive protein (CRP) (Weiser et al., *J. Exp. Med.*, 187: 631-640, 1998). The microenvironment of the nasopharynx and middle ear cavity may select for the ChoP phenotype, as ChoP[4] strains show greater colonization of the chinchilla nasopharynx (Tong et al., *Infect. Immun.*, 68: 4593-4597, 2000). Expression of the licC gene (SEQ ID NO: 633) was also increased. The licC gene encodes a phosphorylcholine cytidylyltransferase that plays a role in the biosynthesis of phosphorylcholine-derivatized LOS (Rock et al., *J. Bacterol.*, 183: 4927-4931, 2001).

Also included among the in vivo-induced genes is a set whose products subsequently regulate gene expression or DNA replication. These genes include transcriptional regulation of glycerol metabolism by the glp repressor, glpR (SEQ ID NO: 643), the arginine repressor gene, argR (SEQ ID NO: 647), and the integration host factor (IHF) beta subunit, ihfB (SEQ ID NO: 645). IHF is a histone-like protein that binds DNA at specific sequences, an accessory factor involved in replication, site-specific recombination and transcription, altering the activity of a large number of operons (Goosen and van de Putte, *Mol. Microbiol.* 16: 1-7, 1995). In addition, CspD inhibits DNA replication during stationary phase-induced stress response in *E. coli* (Yamanaka et al., *Mol. Microbiol.*, 39: 1572-1584, 2001) and the mukF (SEQ ID NO: 641) gene protein homologue contributes to a remodeling of the nucleiod structure into a more compact form prior to cell segregation (Sawitzke and Austin, *Proc. Natl. Acad. Sci. U.S.A.*, 62: 1710-1718, 2000). The DFI strategy described herein also identified promoters induced in vivo for genes of unknown function. The hypothetical protein, HI0094, demonstrated an 8-fold increase in gene expression during early OM but its role remains unknown. HI1163 (SEQ ID NO: 651) showed 58% amino acid identity with the hypothetical YdiJ proteins, a putative oxidase, of *E. coli.*

A high-density transposon mutagenesis strategy was used to identify *H. influenzae* genes essential for growth on rich medium (Akerley et al., *Proc. Natl. Acad. Sci. U.S.A.*, 99: 966-971, 2002). Six genes were identified in the screen described herein that are included in essential gene set described in Akerley et at, supra. (hisB, lppB, lolA, ispZ, mukF and unknown HI0665). Recently genes of non-typeable *H. influenzae* that are expressed upon interaction with two human respiratory tract-derived epithelial cell lines have been identified. These genes included those involved in metabolic processes, stress responses, gene expression, cell envelope biosynthesis. DNA-related processes, cell division and ORF's encoding proteins of unknown function. (Ulsen et al., *Mol. Microbiol.*, 45: 485-500, 2002). Similarly the stress response gene, cspD (SEQ ID NO: 649), genes involved in purine and riboflavin biosynthesis, and a protein of unknown function, vapA was identified in the screen described herein. Expression of vapA was detected in vitro, yet vapA gene expression increased two-fold in vivo. These unique approaches identified known genes that are upregulated in NTHi-induced OM and therefore are likely to play a role in NTHi infection and virulence; and may be potential candidates for vaccines and antisense therapies and other therapeutic methods of treatment of NTHi related disorders.

The DFI strategy resulted in the identification of promoters induced in vivo for genes of unknown function as well. The hypothetical protein, HI0094, demonstrated a 8-fold increase in gene expression during early OM but its role remains unknown. HI1163 (SEQ ID NO: 651) showed 58% amino acid identity with the hypothetical YdiJ proteins, a putative oxidase, of *E. coli*. Therefore, these hypothetical genes are likely to play a role in OM induced by NTHi infection.

BRIEF DESCRIPTION OF FIGURES

FIGS. 3A-3M set out the nucleotide sequences (SEQ ID NOS: 589-614) described in Table 4, which were identified to be upregulated during OM infection (see Example 6). The nucleotides (nt.) which correspond to known genes and those nt. which correspond to the contig sequences set out as SEQ ID NO: 1-576 are also presented.

DETAILED DESCRIPTION

Figure 1:
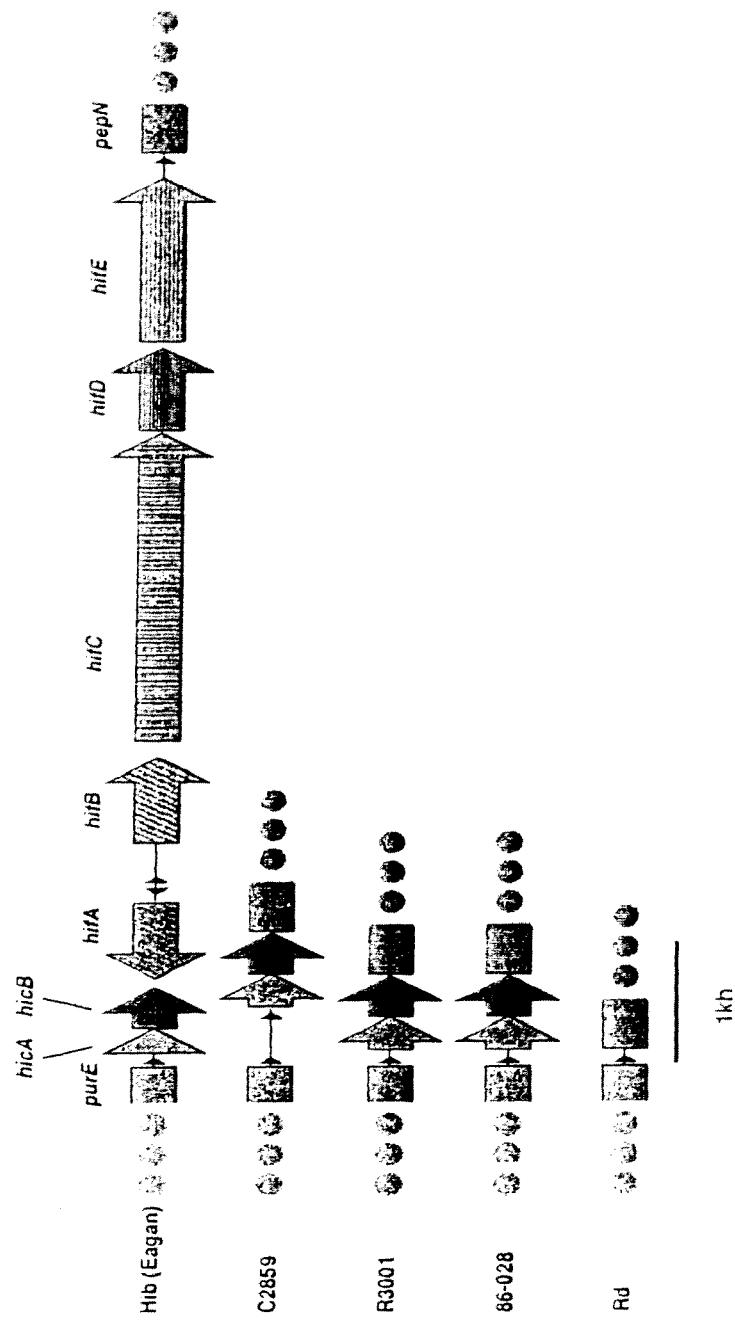
FIG. 1 depicts the LKP gene region in a panel of *Haemophilus* isolates. The strain 86-028NP sequence is identical in this region to the sequence in NTHi strain R3001. Both of these NTH lack the gene cluster encoding the hemagglutinating pilus.

The following examples illustrate the invention wherein Example 1 describes the sequence of the NTHi genome, Example 2 describes the identified contigs and initial gene discovery, Example 3 describes construction of the NTHi promoter trap library, Example 4 describes the analyses of 86-028NP derivatives expressing GFP, Example 5 demonstrates direct labelling of bacteria from middle ear fluids, Example 6 describes identification of promoters induced in vivo in acute otitis media, Example 7 describes identification of virulence-associated genes, and Example 8 describes identification of unique NTHi gene sequences.

EXAMPLE 1

Sequence of a Non-Typeable *Haemophilus influenzae* Genome

NTHi strain 86-028NP is a minimally passaged clinical isolate obtained from a pediatric patient who underwent tympanostomy and tube insertion for chronic OM at Columbus Children's Hospital. (Bakaletz et al. *Infection and Immunity*, 56(2): 331-335, 1988) The 86-028NP strain was deposited with the American Type Tissue Collection (Manassas, Va. 20108 USA) on Oct. 16, 2002 and assigned accession no. PTA-4764.

In an effort to more broadly approach the identification of the virulence determinants in NTHi, the genome of the NTHi 86-028NP strain was sequenced to 3-fold coverage. Chromosomal DNA was prepared from strain S6-028NP using the Puregene protocol and sheared to 2-4 kb in size with a Hvdroshear instrument (Gene Machines). The sheared DNA was ethanol-precipitated, end-repaired using a mixture of Klenow enzyme and T4 DNA polymerase, and size-selected by agarose gel electrophoresis to obtain 2-4 kb fragments as described in Chissoe et al. (*Methods: as Companion to Methods of Enzymology* 3: 55-65, 1991) and Sambrook et al. (*Molecular Cloning: a Laboratory Manual*, $2^{nd}$ Ed. Cold Springs Harbor, N.Y., 1989). These fragments were cloned into vector pUC18 using the SmaI restriction site (phosphatase-treated) and transformed into *E. coli* XL-1 Blue, selecting for ampicillin resistance. Colonies that contain inserts were identified by blue/white screening on LB-Amp plates containing X-gal, and transferred into 96-deep well plates containing 1.5 ml of TB-Amp (TB=Terrific Broth) broth. The deep-well plate cultures were grown overnight (18-22 hours) at 37° C. Template preparation, sequencing and contig assembly were performed.

Automated template preparation was performed on the Beckman Biomek 2000 automated robotics workstation as described in Chissoe et al., (supra.) Briefly, each 96-deep well plate, containing the clones prepared above, was centrifuged to pellet the cells, the supernatant decanted, and the cells frozen (if necessary) at −20° C. Four 96-deep well blocks were placed on the Biomek table, and the liquid handling robot was used to prepare the template using an automated version of a typical SDS-NaOH lysis protocol as described in Chissoe et al., (supra.). The final ethanol-precipitated templates were each dissolved in 50 µl ddH$_2$O, and used for DNA sequencing.

Sequencing reactions were run by re-arraying the templates (from 96-well plates) into 384-well plates, using the Robbins Hydra 96 robot. Cycle-sequencing reactions were run using PE Big-Dye™ terminators and universal primers (M13 forward and reverse), cleaned up over Sephadex G50 columns, and analyzed on a PE Biosystems 3700 capillary electrophoresis DNA sequencer according to the manufacturer's instructions. Sequencing reads (8219) were assembled into 576 contigs (SEQ ID NOS: 1-576 herein). The statistics for the 3-fold sequencing are shown in Table 2A. The total unique sequence in assembly 17 is 1.74 Mb.

TABLE 2A

| Contig Size | Total Number | Total Length | % of Cumulative |
|---|---|---|---|
| 0-1 kb | 65 | 55961 | 3.2% |
| 1-2 kb | 228 | 333665 | 19.2% |
| 2-3 kb | 101 | 243059 | 14.0% |
| 3-4 kb | 49 | 172385 | 9.9% |
| 4-5 kb | 45 | 196699 | 11.3% |
| 5-10 kb | 74 | 515152 | 29.6% |
| 10-20 kb | 11 | 144591 | 8.3% |
| 20-30 kb | 3 | 77352 | 4.4% |

Subsequently, 8-fold sequencing analysis of the NTHi genome was carried out. The 8-fold sequencing assembled the NTHi genome into 11 contigs. Contigs 5, 8, 9, 10, 12-18 are denoted as SEQ ID NOS: 675-685 herein. The statistics for the 8-fold sequencing are shown in Table 2B.

TABLE 2B

| Contig Size | Total Number | Total Length | % of Cumulative |
|---|---|---|---|
| 0-1 kb | 5 | 3950 | 0.2% |
| 1-2 kb | 3 | 4316 | 0.2% |
| 2-3 kb | 0 | 0 | 0.0% |
| 3-4 kb | 1 | 3964 | 0.2% |
| 4-5 kb | 0 | 0 | 0.0% |
| 5-10 kb | 0 | 0 | 0.0% |
| 10-20 kb | 1 | 15147 | 0.8% |
| 20-30 kb | 2 | 51888 | 2.7% |
| 30-40 kb | 0 | 0 | 0.0% |
| 40-50 kb | 0 | 0 | 0.0% |
| 50-100 kb | 1 | 85814 | 4.5% |
| >100 kb | 5 | 1760339 | 91.4% |

EXAMPLE 2

Contig Description and Initial Gene Discovery

Seventy-five of the 88 contigs with length ≧5000 bp, identified with the 3-fold sequence analysis, show significant similarity via BLASTN to genes in *H. influenzae* strain Rd. To visualize the potential relationship between the gene order in *H. influenzae* strain 86-028NP and *H. influenzae* strain Rd, the 86-028NP three-fold contig set and the Rd gene set were bidirectionally compared using BLASTN. The results were plotted in gene-order verses contig space by sorting the contigs based on gene coordinates of the Rd genes hit, anchoring each contig at the smallest coordinate found as described in Ray et al., (*Bioinformatics* 17: 1105-12, 2001). Compared in this fashion, an incomplete assembly of a genome with identical gene order to a completely known genome would display a monotonically increasing stair-stepped form.

BLASTX was used to identify hits to sequences with homology to genes in the strain Rd genome as well as genes not found in *H. influenzae* strain Rd. Hits to strain Rd sequences were removed from the data set and the other hits summarized in Table 3A. The data are presented as follows: contig # (=SEQ ID NO: #1, column 1;E score for each hit, column 2;the name of the protein that had homology to a portion of the amino acid translation of the cited contig, column 3;the organism producing the homologue, column 4;and the Genbank protein identifier for each of the proteins cited in column 3, column 5;the corresponding nucleotides within the contig (referenced by SEQ ID NO:). In most instances, several homologues were identified but for clarity, the protein of greatest homology is cited in Table 3A.

The sequences for some of the genes listed in Table 3A were identified within the 8-fold sequencing of the NTHi genome. Table 3B lists the location of these genes within the 11 contigs, the full length open reading frame sequence (identified by SEQ ID NO:), the derived amino acid sequence encoded by the open reading frame and the gene with high homology identified by BLASTX (as listed in Table 3A).

Figure 2:
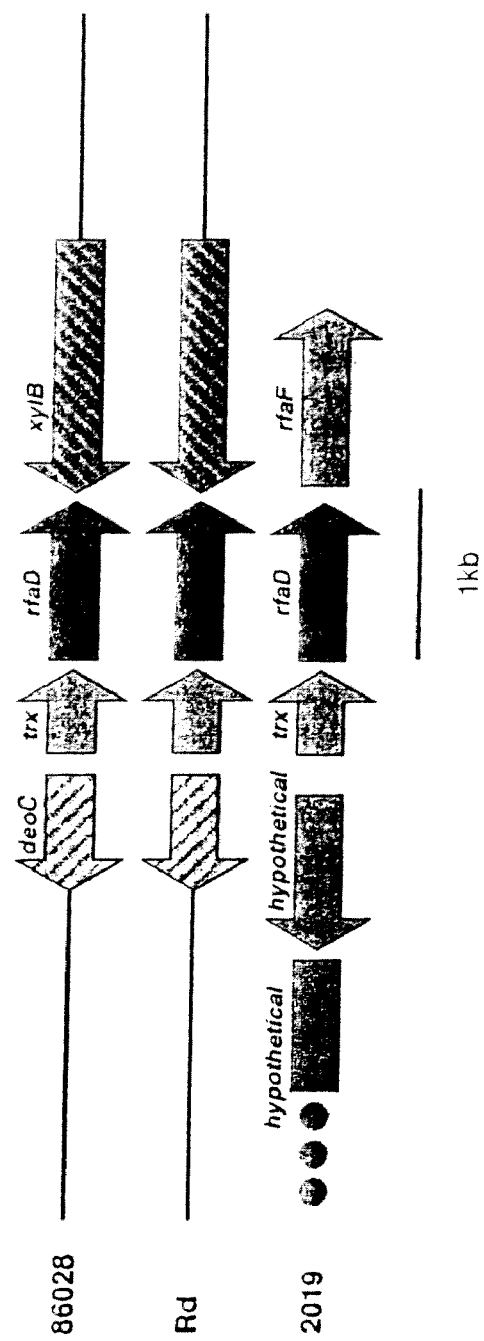
FIG. 2 depicts the rfaD region in a panel of *Haemophilus* isolates. The gene arrangement in the rfaD region of the strain 86-028NP genome is similar to that of the strain Rd genome but different than the arrangement of these genes seen in the genome of most NTHi examined.

To examine the relative short range gene arrangements in NTHi and the Rd strain, the gene order in two gene clusters that have been well-described were compared. First, the genes present in the hemagglutinating pilus (LKP) gene region were examined. (Mhlanea-Mutangadura et al., *J Bacteriol.* 180(17): 4693-703, 1998). The pilus gene cluster is located between the purE and pepN genes, only fragments of which are depicted in FIG. 1. The serotype b strain, Eagan, contains the hifABCDE gene cluster and produces hemagglutinating pili. Strain Rd lacks the hicAB genes as well as the hifABCDE gene cluster. In general, the nontypeable strains previously examined contained the hicAB genes but not the hif genes that encode the hemagglutinating pilus. The strain 86-028NP sequence (described herein) is identical in this region to the sequence in NTHi strain R3001 (FIG. 1). The rfaD gene encodes an enzyme involved in the biosynthesis of endotoxin. In addition, the rfaD gene from NTHi strain 2019 has been characterized by Nichols et al. (*Infect Immunity* 65(4): 1377-86, 1997). In strain 2019, the rfaD gene is immediately upstream of the rfaF gene that encodes another enzyme involved in endotoxin biosynthesis. The gene arrangement in strain Rd is different; the rfaD and rfaF genes are separated by approximately 11 kb of sequence. Most nontypeable strains examined contained the gene arrangement seen in strain 2019. In contrast, strain 86-028NP has a gene arrangement identical to that seen in strain Rd (FIG. 2).

A global analysis of the current assembly indicates that the gene content and order are similar to that in strain Rd. A more detailed analysis revealed that there are a substantial number of NTHi genes not previously seen in the *Pasteurellaceae* and some regions where the NTHi gene content and order is different than that seen in strain Rd. Thus, the current data suggest that the strain 86-028NP genome will contain a complex mosaic of Rd and non-Rd like features.

The DFI strategy also identified novel NTHi sequences that had increased gene expression. A list of these novel contig sequences that contain genes or gene fragments that have homology to ORFs in other organisms (primarily gram-negative bacteria) is set out in Table 3A. For example, the nucleotide sequence of contig 442 (SEQ ID NO: 442), nucleotides 1498-1845 are highly homologous to the sequences encoding amino acids 1-116 of *H. influenzae* strain Rd lipoprotein B (LppB). The gene is positioned between the stationary phase survival gene, surE, and a gene encoding a 43 kD antigenic outer membrane lipoprotein that is highly homologous to the recently identified bacterial lipoprotein, LppB/NlpD, which has been associated with virulence (Padmalayam et al., *Infect. Immun.*, 68: 4972-4979, 2000). Recently, Zhang and coworkers demonstrated that nlpD and surE gene expression was induced during stationary phase of bacterial growth in *Thermotoga maritima* (Zhang et al., *Structure* (*Camb*), 9: 1095-1106, 2001). Therefore, under stress-induced conditions in the middle ear, this NTHi lipoprotein may be expressed.

TABLE 3A

| Contig | E score | Hit Identity | Organism | Genbank Protein | SEQ ID NO: |
|---|---|---|---|---|---|
| 104 | 4.00E−59 | CpdB | *Pasteurella multocida* | NP_246953.1 | nt. 204-659 of SEQ ID NO: 104 |
| 106 | 9.00E−10 | hypothetical protein PH0217 - | *Pyrococcus horikoshii* | G71244 | nt. 40-309 of SEQ ID NO: 106 |
| 106 | 1.00E−08 | unknown | *Pasteurella multocida* | NP_246871.1 | nt. 605-694 of SEQ ID NO: 106 |
| 106 | 2.00E−20 | Orf122 | *Chlorobium tepidum* | AAG12204.1 | nt. 7-210 of SEQ ID NO: 106 |
| 110 | 3.00E−05 | ArdC antirestriction protein | IncW plasmid pSa | AAD52160.1 | compliment of nt. 959-1162 of SEQ ID NO: 110 |
| 110 | 1.00E−33 | hypothetical protein | *Salmonella enterica* subsp. *enterica* serovar Typhi | NP_458676.1 | compliment of nt. nt. 181-825 of SEQ ID NO: 110 |
| 111 | 5.00E−12 | putative membrane protein | *Salmonella enterica* subsp. *enterica* serovar Typhi | NP_458664.1 | compliment of nt. 45-287 of SEQ ID NO: 111 |
| 111 | 6.00E−41 | hypothetical protein | *Salmonella enterica* subsp. *enterica* serovar Typhi | NP_458658.1 | compliment of nt. 1091-1480 of SEQ ID NO: 111 |
| 114 | 7.00E−80 | unknown | *Pasteurella multocida* | NP_245828.1 | compliment of nt. 118-696 of SEQ ID NO: 114 |

TABLE 3A-continued

| Contig | E score | Hit Identity | Organism | Genbank Protein | SEQ ID NO: |
|---|---|---|---|---|---|
| 115 | 2.00E−09 | A111R | *Paramecium bursaria Chlorella virus 1* | NP_048459.1 | nt. 555-869 of SEQ ID NO: 115 |
| 118 | 5.00E−45 | DNA methylase HsdM, putative | *Vibrio cholerae* | NP_231404.1 | nt. 44-439 of SEQ ID NO: 118 |
| 122 | 2.00E−18 | unknown | *Pasteurella multocida* | NP_245314.1 | nt. 865-1302 of SEQ ID NO: 122 |
| 123 | 4.00E−99 | RNA POLYMERASE SIGMA-32 FACTOR | *Proteus mirabilis* | P50509 | nt. 351-782 of SEQ ID NO: 123 |
| 124 | 9.00E−58 | ACETOLACTATE SYNTHASE (ACETOHYDROXY-ACID SYNTHASE) (ALS) | *Spirulina platensis* | P27868 | nt. 603-1025 of SEQ ID NO: 124 |
| 130 | 0 | restriction modification system-R protein | *Neisseria meningitidis* | CAA09003.1 | nt. 495-1559 of SEQ ID NO: 130 |
| 131 | 6.00E−91 | uronate isomerase (glucuronate isomerase) | *Salmonella enterica* subsp. *enterica* serovar *Typhi* | NP_457532.1 | compliment of nt. 661-1380 of SEQ ID NO: 131 |
| 133 | 3.00E−30 | GyrA | *Pasteurella multocida* | NP_245778.1 | compliment of nt. 1447-1626 of SEQ ID NO: 133 |
| 133 | 1.00E−27 | DNA GYRASE SUBUNIT A | *Pectobacterium carotovorum* | P41513 | compliment of nt. 1302-1442 of SEQ ID NO: 133 |
| 138 | 7.00E−06 | KicA | *Pasteurella multocida* | NP_245545.1 | compliment of nt. 92-157 of SEQ ID NO: 138 |
| 138 | 1.00E−148 | TYPE II RESTRICTION ENZYME HAEII (ENDONUCLEASE HAEII) (R. HAEII) | *Haemophilus aegyptius* | O30869 | compliment of nt. 164-1045 of SEQ ID NO: 138 |
| 143 | 4.00E−06 | Gifsy-1 prophage protein | *Salmonella typhimurium* LT2 | NP_461555.1 | compliment of nt. 228-632 of SEQ ID NO: 143 |
| 143 | 1.00E−14 | hypothetical protein | Bacteriophage VT2-Sa | NP_050531.1 | compliment of nt. 778-1248 of SEQ ID NO: 143 |
| 143 | 5.00E−09 | hypothetical protein | *Salmonella enterica* subsp. *enterica* serovar *Typhi* | CAD09979.1 | compliment of nt. 715-1026 of SEQ ID NO: 143 |
| 143 | 6.00E−10 | hypothetical 14.9 kd protein | *Escherichia coli* | NP_065324.1 | nt. 3-173 of SEQ ID NO: 143 |
| 147 | 1.00E−38 | GTP-binding elongation factor, may be inner membrane protein | *Escherichia coli* O157:H7 EDL933 | NP_289127.1 | compliment of nt. 172-342 of SEQ ID NO: 147 |
| 147 | 2.00E−14 | GTP-binding membrane protein (lepA) | *Borrelia burgdorferi* | NP_212222.1 | compliment of nt. 17-181 of SEQ ID NO: 147 |
| 148 | 6.00E−17 | galactokinase | *Homo sapiens* | AAC35849.1 | compliment of nt. 746-1246 of SEQ ID NO: 148 |
| 148 | 7.00E−96 | GALACTOKINASE (GALACTOSE KINASE) | *Actinobacillus pleuropneumoniae* | P94169 | compliment of nt. 232-741 of SEQ ID NO: 148 |
| 149 | 1.00E−92 | GTP-binding protein TypA/BipA | *Buchnera* sp. APS | NP_240245.1 | compliment of nt. 265-1077 of SEQ ID NO: 149 |
| 15 | 2.00E−21 | ORF1 | *Escherichia coli* | CAA39631.1 | nt. 665-850 of SEQ ID NO: 15 |
| 150 | 6.00E−17 | unknown | *Pasteurella multocida* | NP_245919.1 | nt. 171-665 of SEQ ID NO: 150 |
| 153 | 7.00E−07 | cuter membrane protein A | *Rickettsia conorii* | T30852 | nt. 51-623 of SEQ ID NO: 153 |
| 155 | 7.00E−40 | cytochrome d ubiquinol oxidase, subunit II | *Vibrio cholerae* | NP_233259.1 | nt. 583-1002 of SEQ ID NO: 155 |
| 157 | 7.00E−13 | unknown | *Pasteurella multocida* | NP_245490.1 | compliment of nt. 1170-1367 of SEQ ID NO: 157 |

TABLE 3A-continued

| Contig | E score | Hit Identity | Organism | Genbank Protein | SEQ ID NO: |
|---|---|---|---|---|---|
| 157 | 2.00E−05 | glycosyl transferase | Neisseria gonorrhoeae | AAA68012.1 | nt. 85-189 of SEQ ID NO: 157 |
| 158 | 1.00E−152 | MltC | Pasteurella multocida | NP_246259.1 | compliment of nt. 36-530 of SEQ ID NO: 158 |
| 161 | 3.00E−25 | lipoprotein, putative | Vibrio cholerae | NP_230232.1 | nt. 870-1439 of SEQ ID NO: 161 |
| 163 | 9.00E−53 | chorismate synthase | Caulobacter crescentus | NP_421948.1 | nt. 1283-2029 of SEQ ID NO: 163 |
| 168 | 3.00E−13 | COPPER-TRANSPORTING ATPASE 1 (COPPER PUMP 1) | Mus musculus | Q64430 | nt. 66-995 of SEQ ID NO: 168 |
| 168 | 2.00E−22 | Cu transporting ATPase P | Homo sapiens | 2001422A | nt. 135-989 of SEQ ID NO: 168 |
| 174 | 8.00E−48 | magnesium/cobalt transport protein | Mesorhizobium loti | NP_103977.1 | nt. 918-1205 of SEQ ID NO: 174 |
| 175 | 5.00E−26 | vacB protein | Buchnera sp. APS | NP_240369.1 | compliment of nt. 1-1587 of SEQ ID NO: 175 |
| 176 | 3.00E−21 | putative ABC transport system permease protein [ | Campylobacter jejuni | NP_282774.1 | compliment of nt. 259-1089 of SEQ ID NO: 176 |
| 183 | 5.00E−29 | PROBABLE ATP SYNTHASE A CHAIN TRANSMEMBRANE PROTEIN | Ralstonia solanacearum | NP_521442.1 | compliment of nt. 42-677 of SEQ ID NO: 183 |
| 185 | 6.00E−85 | putative exported protein | Salmonella enterica subsp. enterica serovar Typhi | NP_458655.1 | compliment of nt. 162-1529 of SEQ ID NO: 185 |
| 187 | 2.00E−05 | transketolase | Homo sapiens | AAA61222.1 | nt. 709-819 of SEQ ID NO: 187 |
| 188 | 1.00E−116 | ribonuclease E | Xylella fastidiosa 9a5c | NP_299884.1 | compliment of nt. 280-1704 of SEQ ID NO: 188 |
| 192 | 1.00E−38 | ImpA | Pasteurella multocida | NP_245829.1 | nt. 35-448 of SEQ ID NO: 192 |
| 193 | 3.00E−08 | Orf80 | Enterobacteria phage 186 | NP_052285.1 | nt. 1612-1818 of SEQ ID NO: 193 |
| 193 | 1.00E−06 | holin | Haemophilus somnus | AAC45168.1 | nt. 370-576 of SEQ ID NO: 193 |
| 193 | 0.007 | unknown | Enterobacteria phage 186 | NP_052260.1 | nt. 1376-1609 of SEQ ID NO: 193 |
| 193 | 2.00E−48 | lysozyme | Haemophilus somnus | AAC45169.1 | nt. 608-1093 of SEQ ID NO: 193 |
| 199 | 4.00E−21 | unknown protein | Escherichia coli O157:H7 EDL933, prophage CP-933V | NP_288675.1 | nt. 398-778 of SEQ ID NO: 199 |
| 199 | 2.00E−49 | hypothetical protein | Bacteriophage 933W | NP_049495.1 | compliment of nt. 1907-2392 of SEQ ID NO: 199 |
| 20 | 1.00E−62 | RpL14 | Pasteurella multocida | NP_246344.1 | compliment of nt. 233-601 of SEQ ID NO: 20 |
| 200 | 2.00E−62 | hypothetical protein | Salmonella enterica subsp. enterica serovar Typhi | NP_458658.1 | compliment of nt. 431-997 of SEQ ID NO: 200 |
| 200 | 3.00E−16 | hypothetical protein | Salmonella enterica subsp. enterica serovar Typhi | NP_458657.1 | compliment of nt. 1028-1264 of SEQ ID NO: 200 |
| 201 | 2.00E−26 | TsaA | Pasteurella multocida | NP_245732.1 | compliment of nt. 1618-1809 of SEQ ID NO: 201 |
| 209 | 6.00E−16 | TsaA | Pasteurella multocida | NP_245732.1 | compliment of nt. 2-136 of SEQ ID NO: 209 |
| 211 | 2.00E−15 | unknown | Pasteurella multocida | NP_245535.1 | compliment of nt. 23-211 of SEQ ID NO: 211 |

TABLE 3A-continued

| Contig | E score | Hit Identity | Organism | Genbank Protein | SEQ ID NO: |
|---|---|---|---|---|---|
| 211 | 1.00E−70 | PUTATIVE ATPASE PROTEIN | *Ralstonia solanacearum* | NP_520082.1 | compliment of nt. 475-915 of SEQ ID NO: 211 |
| 212 | 3.00E−18 | hypothetical protein | *Escherichia coli* O157:H7 | NP_309775.1 | compliment of nt. 895-1035 of SEQ ID NO: 212 |
| 216 | 1.00E−173 | unknown | *Pasteurella multocida* | NP_245069.1 | nt. 35-1543 of SEQ ID NO: 216 |
| 217 | 9.00E−18 | diacylglycerol kinase | *Vibrio cholerae* | NP_233101.1 | nt. 2083-2208 of SEQ ID NO: 217 |
| 221 | 4.00E−34 | Tail-Specific Protease | *Chlamydia trachomatis* | NP_219953.1 | nt. 849-1421 of SEQ ID NO: 221 |
| 222 | 4.00E−23 | AGR_C_3689p | *Agrobacterium tumefaciens* str. C58 (Cereon) | NP_355005.1 | compliment of nt. 940-1305 of SEQ ID NO: 222 |
| 224 | 9.00E−19 | unknown | *Pasteurella multocida* | NP_245536.1 | nt. 15-308 of SEQ ID NO: 224 |
| 225 | 1.00E−89 | portal vector-like protein, in phage P2 [*Salmonella typhimurium* LT2] | *Salmonella typhimurium* LT2Fels-2 prophage | NP_461651.1 | nt. 31-750 of of SEQ ID NO: 225 |
| 229 | 2.00E−25 | anaerobic ribonucleotide reductase | *Salmonella typhimurium* | CAB62266.1 | nt. 1806-2108 of SEQ ID NO: 229 |
| 234 | 3.00E−08 | conserved hypothetical protein | *Xylella fastidiosa* 9a5c | NP_299850.1 | nt. 1680-2048 of SEQ ID NO: 234 |
| 234 | 1.00E−42 | Methionine sulfoxide reductase C-terminal domain related protein, YPPQ ortholog | *Clostridium acetobutylicum* | NP_348177.1 | compliment of nt. 415-654 of SEQ ID NO: 234 |
| 235 | 4.00E−16 | phage-related tail protein | *Wolbachia* endosymbiont of *Drosophila melanogaster* | AAK85310.1 | compliment of nt. 931-1999 of SEQ ID NO: 235 |
| 235 | 6.00E−56 | similar to orfG protein in phage 186, *Salmonella typhimurium* LT2 | *Salmonella typhimurium* LT2, Fels-2 prophage | NP_461625.1 | compliment of nt. 313-1863 of SEQ ID NO: 235 |
| 236 | 6.00E−20 | conserved hypothetical protein | *Pseudomonas aeruginosa* | NP_252693.1 | nt. 1572-1916 of SEQ ID NO: 236 |
| 240 | 5.00E−27 | MODIFICATION METHYLASE BEPI | *Brevibacterium epidermidis* | P10283 | compliment of nt. 922-1305 of SEQ ID NO: 240 |
| 241 | 2.00E−15 | phage-related protein | *Xylella fastidiosa* 9a5c | NP_299573.1 | compliment of nt. 865-1305 of SEQ ID NO: 241 |
| 241 | 4.00E−08 | hypothetical protein | phage SPP1 | T42296 | nt. 73-636 of SEQ ID NO: 241 |
| 241 | 4.00E−07 | hypothetical protein | *Salmonella enterica* subsp. *enterica* serovar Typhi | NP_458686.1 | nt. 10-468 of SEQ ID NO: 241 |
| 242 | 2.00E−29 | translation elongation factor EF-G | chloroplast-soybean | S35701 | compliment of nt. 18-1085 of SEQ ID NO: 242 |
| 247 | 3.00E−23 | GTP CYCLOHYDROLASE I (GTP-CH-I) | *Synechococcus* sp. PCC 7942 | Q54769 | compliment of nt. 1009-1257c of SEQ ID NO: 247 |
| 248 | 6.00E−05 | phospho-N-acetylmuramoyl-pentapeptide-transferase | *Aquifex aeolicus* | NP_213025.1 | nt. 830-1747 of SEQ ID NO: 248 |
| 25 | 2.00E−86 | PROBABLE TRANSPORT TRANSMEMBRANE PROTEIN | *Ralstonia solanacearum* | NP_522358.1 | compliment of nt. 309-854 of SEQ ID NO: 25 |
| 25 | 7.00E−06 | major facilitator family transporter | *Caulobacter crescentus* | NP_419155.1 | compliment of nt. 134-283 of SEQ ID NO: 25 |
| 250 | 1.00E−150 | CpdB | *Pasteurella multocida* | NP_246953.1 | compliment of nt. 36-1016 of SEQ ID NO: 250 |

TABLE 3A-continued

| Contig | E score | Hit Identity | Organism | Genbank Protein | SEQ ID NO: |
|---|---|---|---|---|---|
| 252 | 3.00E−57 | alanyl-tRNA synthetase | Vibrio cholerae | AAA99922.1 | compliment of nt. 1418-1951 of SEQ ID NO: 252 |
| 253 | 1.00E−108 | similar to glutathione Reductase | Listeria monocytogenes EGD-e | NP_464432.1 | compliment of nt. 411-1358 of of SEQ ID NO: 253 |
| 259 | 3.00E−39 | hypothetical protein | Salmonella enterica subsp. enterica serovar Typhi | NP_458654.1 | compliment of nt. 342-1037 of SEQ ID NO: 259 |
| 259 | 3.00E−17 | possible exported protein | Salmonella enterica subsp. enterica serovar Typhi | NP_458653.1 | compliment of nt. 1251-1607 of SEQ ID NO: 259 |
| 261 | 5.00E−74 | hypothetical protein 6 - Haemophilus influenzae | Haemophilus influenzae | S27582 | compliment of nt. 3-422 of SEQ ID NO: 261 |
| 263 | 1.00E−94 | putative transposase | Haemophilus paragallinarum | AAD01406.1 | nt. 2142-2672 of SEQ ID NO: 263 |
| 264 | 1.00E−126 | unknown | Actinobacillus actinomycetemcomitans | NP_067554.1 | nt. 40-714 of SEQ ID NO: 264 |
| 264 | 1.00E−103 | unknown | Actinobacillus actinomycetemcomitans | NP_067555.1 | nt. 695-1309 of SEQ ID NO: 264 |
| 264 | 2.00E−21 | unknown | Actinobacillus actinomycetemcomitans | NP_067556.1 | nt. 1302-1448 of SEQ ID NO: 264 |
| 265 | 6.00E−27 | Aminopeptidase 2 | chloroplast | Q42876 | nt. 556-1539 of SEQ ID NO: 265 |
| 268 | 1.00E−116 | MutY | Pasteurella multocida | NP_246257.1 | nt. 1003-1581 of SEQ ID NO: 268 |
| 272 | 1.00E−07 | hypothetical protein | Bacteriophage 933W | NP_049495.1 | compliment of nt. 77-232 of SEQ ID NO: 272 |
| 274 | 3.00E−13 | unknown | Pasteurella multocida | NP_246952.1 | compliment of nt. 1658-1975 of SEQ ID NO: 274 |
| 275 | 3.00E−20 | CafA | Neisseria gonorrhoeae | AAG24267.1 | nt. 1299-1571 of SEQ ID NO: 275 |
| 276 | 1.00E−45 | mukE protein | Vibrio cholerae | NP_231351.1 | compliment of nt. 650-1390 of SEQ ID NO: 276 |
| 276 | 1.00E−69 | KicA | Pasteurella multocida | NP_245545.1 | compliment of nt. 647-1321 of SEQ ID NO: 276 |
| 278 | 2.00E−56 | 3-oxoacyl-[acyl-carrier-protein] synthase III | Salmonella enterica subsp. enterica serovar Typhi | NP_455686.1 | nt. 1366-1944 of SEQ ID NO: 278 |
| 281 | 5.00E−56 | unknown | Pasteurella multocida | NP_246261.1 | compliment of nt. 31-678 of SEQ ID NO: 281 |
| 282 | 3.00E−09 | orf25; similar to T gene of P2 | bacteriophage phi CTX | NP_490625.1 | compliment of nt. 511-1032 of SEQ ID NO: 282 |
| 282 | 1.00E−08 | orf11; similar to phage P2 gene S-like product, which is involved in tail synthesis, | Haemophilus somnus | AAC45165.1 | compliment of nt. 1450-1584 of SEQ ID NO: 282 |
| 282 | 9.00E−27 | putative bacteriophage tail protein | Salmonella enterica subsp. enterica serovar Typhi | NP_457167.1 | compliment of nt. 3-509 of SEQ ID NO: 282 |
| 286 | 5.00E−18 | plasmid-related protein | Listeria innocua plasmid | NP_471066.1 | compliment of nt. 887-1501 of SEQ ID NO: 286 |
| 287 | 8.00E−20 | GTP cyclohydrolase II | Escherichia coli O157:H7 EDL933 | NP_287920.1 | nt. 2-145 of SEQ ID NO: 287 |
| 289 | 1.00E−168 | MODIFICATION METHYLASE HAEII | Haemophilus aegyptius | O30868 | compliment of nt. 138-1091 of SEQ ID NO: 289 |
| 289 | 5.00E−11 | TYPE II RESTRICTION ENZYME HAEII | Haemophilus aegyptius | O30869 | compliment of nt. 22-132 of SEQ ID NO: 289 |

TABLE 3A-continued

| Contig | E score | Hit Identity | Organism | Genbank Protein | SEQ ID NO: |
|---|---|---|---|---|---|
| 289 | 6.00E−47 | mukF homolog | Haemophilus influenzae biotype aegyptius | AAB70828.1 | compliment of nt. 1107-1385 of SEQ ID NO: 289 |
| 294 | 1.00E−171 | LICA PROTEIN | Haemophilus influenzae RM7004 | P14181 | compliment of nt. 677-1564 of SEQ ID NO: 294 |
| 297 | 1.00E−158 | DNA methylase HsdM, putative | Vibrio cholerae | NP_231404.1 | compliment of nt. 12-1136 of SEQ ID NO: 297 |
| 302 | 0 | HEME-BINDING PROTEIN A | Haemophilus influenzae DL42 | P33950 | nt.3-1316 of SEQ ID NO: 302 |
| 304 | 6.00E−19 | hypothetical protein 6 | Haemophilus influenzae | S27582 | nt. 121-267 of SEQ ID NO: 304 |
| 305 | 6.00E−40 | putative recombinase - phage associated | Streptococcus pyogenes M1 GAS | NP_269557.1 | nt. 65-805 of SEQ ID NO: 305 |
| 305 | 7.00E−22 | single stranded DNA-binding protein | Shewanella sp. F1A | AAB57886.1 | nt. 1607-2014 of SEQ ID NO: 305 |
| 305 | 1.00E−43 | phage-related protein | Bacillus halodurans | NP_244410.1 | nt. 92-751 of SEQ ID NO: 305 |
| 312 | 1.00E−28 | PUTATIVE BACTERIOPHAGE-RELATED TRANSMEMBRANE PROTEIN | Ralstonia solanacearum | NP_518994.1 | nt. 1819-2673 of SEQ ID NO: 312 |
| 312 | 9.00E−25 | similar to BASEMENT MEMBRANE-SPECIFIC HEPARAN SULFATE PROTEOGLYCAN CORE PROTEIN PRECURSOR (HSPG) | Homo sapiens | XP_068727.1 | nt. 27-1001 of SEQ ID NO: 312 |
| 315 | 2.00E−45 | uracil permease | Deinococcus radiodurans | NP_296001.1 | compliment of nt. 525-1592 of SEQ ID NO: 315 |
| 318 | 7.00E−15 | CzcD | Pasteurella multocida | NP_246276.1 | compliment of nt. 3-227 of SEQ ID NO: 318 |
| 320 | 2.00E−60 | orf3; similar to endonuclease subunit of the phage P2 terminase (gene M) | Haemophilus somnus | AAC45159.1 | compliment of nt. 606-1241 of SEQ ID NO: 320 |
| 320 | 2.00E−09 | orf4; similar to head completion/stabilization protein (gene L) of phage P2 | Haemophilus somnus | AAC45160.1 | compliment of nt. 52-285 of SEQ ID NO: 320 |
| 320 | 3.00E−35 | orf2; similar to major capsid protein precursor of phage P2 (gene N) | Haemophilus somnus | AAC45158.1 | compliment of nt. 1271-1624 of SEQ ID NO: 320 |
| 323 | 4.00E−37 | dedC protein | Escherichia coli | AAA23966.1 | compliment of nt. 74-463 of SEQ ID NO: 323 |
| 324 | 1.00E−153 | conserved hypothetical protein | Neisseria meningitidis MC58 | NP_274972.1 | compliment of nt. 930-1943 of SEQ ID NO: 324 |
| 326 | 5.00E−52 | selenophosphate synthetase | Eubacterium acidaminophilum | CAB53511.1 | compliment of nt. 1186-2292 of SEQ ID NO: 326 |
| 328 | 1.00E−129 | secretion protein SecD | Pseudomonas aeruginosa | NP_252510.1 | compliment of nt. 8-625 of SEQ ID NO: 328 |
| 333 | 3.00E−08 | unknown | Pasteurella multocida | NP_245489.1 | compliment of nt. 5-418 of SEQ ID NO: 333 |
| 336 | 6.00E−38 | probable methyl transferase | Pseudomonas aeruginosa | NP_253353.1 | compliment of nt. 2547-2819 of SEQ ID NO: 336 |
| 338 | 2.00E−98 | Pmi | Pasteurella multocida | NP_245766.1 | nt. 144-842 of SEQ ID NO: 338 |

TABLE 3A-continued

| Contig | E score | Hit Identity | Organism | Genbank Protein | SEQ ID NO: |
|---|---|---|---|---|---|
| 339 | 2.00E−07 | tRNA nucleotidyltransferase | *Escherichia coli* | QQECPE | nt. 2331-2540 of SEQ ID NO: 339 |
| 340 | 0 | DNA gyrase, subunit A, type II topoisomerase | *Salmonella typhimurium* LT2 | NP_461214.1 | compliment of nt. 93-1799 of SEQ ID NO: 340 |
| 342 | 4.00E−12 | tolA protein | *Haemophilus influenzae* | JC5212 | nt. 980-1318 of SEQ ID NO: 342 |
| 344 | 1.00E−07 | MODIFICATION METHYLASE HPHIA | *Haemophilus parahaemolyticus* | P50192 | compliment of nt. 849-1034 of SEQ ID NO: 344 |
| 344 | 8.00E−05 | ABC transporter protein 1 | *Leishmania major* | AAF31030.1 | compliment of nt. 17-205 of SEQ ID NO: 344 |
| 349 | 3.00E−44 | conserved hypothetical protein | *Neisseria meningitidis* MC58 | NP_273467.1 | compliment of nt. 1397-1903 of SEQ ID NO: 349 |
| 349 | 8.00E−09 | hypothetical protein | *Pseudomonas aeruginosa* | NP_252667.1 | compliment of nt. 795-1121 of SEQ ID NO: 349 |
| 349 | 9.00E−10 | conserved hypothetical secreted protein | *Helicobacter pylori* 26695 | NP_207009.1 | compliment of nt. 1319-1816 of SEQ ID NO: 349 |
| 349 | 2.00E−06 | putative TPR repeat protein | *Salmonella typhimurium* LT2 | NP_463149.1 | compliment of nt. 2244-2558 of SEQ ID NO: 349 |
| 35 | 1.00E−23 | type I restriction-modification system specificity determinant | *Xylella fastidiosa* 9a5c | NP_300003.1 | compliment of nt. 29-388 of SEQ ID NO: 35 |
| 352 | 1.00E−116 | putative peptidase | *Escherichia coli* K12 | NP_416827.1 | compliment of nt. 951-1640 of SEQ ID NO: 352 |
| 352 | 0 | unknown | *Pasteurella multocida* | NP_245275.1 | compliment of nt. 86-946 of SEQ ID NO: 352 |
| 354 | 5.00E−86 | putative uronate isomerase | *Salmonella typhimurium* LT2 | NP_462052.1 | compliment of nt. 168-914 of SEQ ID NO: 354 |
| 356 | 1.00E−07 | isomerase-like protein (DsbD) - | *Escherichia coli* | S57220 | nt. 5-73 of SEQ ID NO: 356 |
| 358 | 1.00E−07 | USG protein | *Pediococcus pentosaceus* | CAC16793.1 | nt.534-1307 of SEQ ID NO: 358 |
| 358 | 0.005 | HsdS protein | *Escherichia coli* | CAA10700.1 | nt. 26-205 of SEQ ID NO: 358 |
| 361 | 1.00E−152 | maltodextrin phosphorylase | *Escherichia coli* O157:H7 EDL933 | NP_289957.1 | compliment of nt. 77-922 of SEQ ID NO: 361 |
| 363 | 6.00E−06 | BH2505~unknown conserved protein | *Bacillus halodurans* | NP_243371.1 | nt. 554-844 of SEQ ID NO: 363 |
| 368 | 1.00E−12 | H02F09.3.p | *Caenorhabditis elegans* | NP_508295.1 | compliment of nt. 1069-1977 of SEQ ID NO: 368 |
| 368 | 6.00E−27 | hypothetical glycine-rich protein | *Mesorhizobium loti* | NP_102360.1 | compliment of nt. 1201-1986 of SEQ ID NO: 368 |
| 37 | 6.00E−09 | putative ATP-binding component of a transport system | *Escherichia coli* K12 | NP_415469.1 | compliment of nt. 455-691 of SEQ ID NO: 37 |
| 372 | 7.00E−18 | conserved hypothetical protein | *Clostridium perfringens* | BAB80319.1 | compliment of nt. 1763-1924 of SEQ ID NO: 372 |
| 376 | 7.00E−24 | putative bacteriophage protein | *Salmonella enterica* subsp. *enterica* serovar Typhi | NP_456379.1 | compliment of nt. 158-808 of SEQ ID NO: 376 |
| 376 | 8.00E−10 | hypothetical protein | *Xylella fastidiosa* 9a5c | NP_298882.1 | compliment of nt. 1129-1671 of SEQ ID NO: 376 |
| 376 | 9.00E−06 | lin1713 | *Listeria innocua* | NP_471049.1 | compliment of nt 913-1557 of SEQ ID NO: 376 |
| 377 | 6.00E−05 | Vng1732c | *Halobacterium* sp. NRC-1 | NP_280487.1 | nt. 2378-2587 of SEQ ID NO: 377 |

TABLE 3A-continued

| Contig | E score | Hit Identity | Organism | Genbank Protein | SEQ ID NO: |
|---|---|---|---|---|---|
| 377 | 1.00E−11 | INVASIN PRECURSOR (OUTER MEMBRANE ADHESIN) | *Yersinia enterocolitica* | P31489 | compliment of nt. 127-345 of SEQ ID NO: 377 |
| 382 | 4.00E−16 | unknown | *Pasteurella multocida* | NP_246871.1 | compliment of nt. 967-1068 of SEQ ID NO: 382 |
| 383 | 4.00E−36 | putative transposase | *Streptomyces avermitilis* | BAB69302.1 | nt. 488-1162 of SEQ ID NO: 383 |
| 383 | 3.00E−58 | recombinase | IncN plasmid R46 | NP_511241.1 | compliment of nt. 1-393 of SEQ ID NO: 383 |
| 383 | 4.00E−24 | transposase | *Escherichia coli* | I69674 | nt. 1294-1740 of SEQ ID NO: 383 |
| 383 | 0 | tnpA | *Yersinia enterocolitica* | CAA73750.1 | nt. 1782-2834 of SEQ ID NO: 383 |
| 385 | 2.00E−31 | unknown | *Pasteurella multocida* | NP_246065.1 | nt. 1515-1772 of SEQ ID NO: 385 |
| 386 | 5.00E−65 | cydC [ | *Escherichia coli* | AAA66172.1 | compliment of nt. 3438-4115 of SEQ ID NO: 386 |
| 386 | 4.00E−33 | ABC transporter, ATP-binding protein | *Mesorhizobium loti* | NP_105463.1 | compliment of nt. 2569-3390 of SEQ ID NO: 386 |
| 388 | 3.00E−45 | 60 KDA INNER-MEMBRANE PROTEIN HOMOLOG | *Coxiella burnetii* | P45650 | compliment of nt. 3211-3759 of SEQ ID NO: 388 |
| 390 | 4.00E−25 | putative DNA-binding protein | *Salmonella enterica* subsp. *enterica* serovar *Typhi* | NP_458175.1 | nt. 1051-1416 of SEQ ID NO: 390 |
| 390 | 3.00E−13 | transcriptional regulator | *Bacillus halodurans* | NP_241773.1 | compliment of nt. 84-578 of SEQ ID NO: 390 |
| 390 | 3.00E−06 | DNA translocase stage III sporulation prot homolog | *Staphylococcus aureus* subsp. *aureus* Mu50 | NP_372265.1 | compliment of nt. 620-871 of SEQ ID NO: 390 |
| 395 | 7.00E−31 | ATPase, Cu++ transporting, beta polypeptide | *Homo sapiens* | NP_000044.1 | compliment of nt. 615-1406 of SEQ ID NO: 395 |
| 397 | 3.00E−23 | terminase large subunit | Bacteriophage HK620 | NP_112076.1 | compliment of nt. 2363-2725 of SEQ ID NO: 397 |
| 397 | 3.00E−16 | hypothetical protein | *Xylella fastidiosa* 9a5c | NP_297824.1 | compliment of nt. 1517-1744 of SEQ ID NO: 397 |
| 398 | 4.00E−67 | orf32 | *Haemophilus* phage HP2 | NP_536839.1 | compliment of nt. 1288-1866 of SEQ ID NO: 398 |
| 398 | 8.00E−24 | putative cytoplasmic protein | *Salmonella typhimurium* LT2 | NP_463063.1 | compliment of nt. 798-1220 of SEQ ID NO: 398 |
| 398 | 2.00E−83 | orf31 | *Haemophilus* phage HP1 | NP_043502.1 | compliment of nt. 1881-2510 of SEQ ID NO: 398 |
| 399 | 1.00E−94 | HEME/HEMOPEXIN-BINDING PROTEIN | *Haemophilus influenzae* N182 | P45355 | nt. 88-774 of SEQ ID NO: 399 |
| 401 | 3.00E−63 | Sty SBLI | *Salmonella enterica* | CAA68058.1 | nt. 1690-2742 of SEQ ID NO: 401 |
| 401 | 3.00E−06 | RESTRICTION-MODIFICATION ENZYME SUBUNIT M3 | *Mycoplasma pulmonis* | NP_325912.1 | nt. 79-489 of SEQ ID NO: 401 |
| 402 | 2.00E−13 | OPACITY PROTEIN OPA66 PRECURSOR | *Neisseria gonorrhoeae* | Q05033 | compliment of nt. 2634-2915 of SEQ ID NO: 402 |
| 406 | 8.00E−13 | type I restriction enzyme EcoR124IIR | *Neisseria meningitidis* MC58 | NP_273876.1 | nt. 281-520 of SEQ ID NO: 406 |
| 407 | 6.00E−65 | unknown | *Pasteurella multocida* | NP_246237.1 | nt. 938-2450 of SEQ ID NO: 407 |
| 407 | 5.00E−99 | PepE | *Pasteurella multocida* | NP_245391.1 | nt. 1216-1917 of SEQ ID NO: 407 |

TABLE 3A-continued

| Contig | E score | Hit Identity | Organism | Genbank Protein | SEQ ID NO: |
|---|---|---|---|---|---|
| 407 | 1.00E−16 | Hemoglobin-haptoglobin binding protein A | *Haemophilus influenzae* Tn106 | Q48153 | nt. 1-141 of SEQ ID NO: 407 |
| 409 | 1.00E−106 | hypothetical protein 1 | *Haemophilus influenzae* | S27577 | compliment of nt. 2524-3159 of SEQ ID NO: 409 |
| 411 | 4.00E−29 | heme-repressible hemoglobin-binding protein | *Haemophilus influenzae*, type b, strain HI689 | AAB46794.1 | nt. 391-615 of SEQ ID NO: 411 |
| 411 | 0 | Hemoglobin-haptoglobin binding protein A | *Haemophilus influenzae* Tn106 | Q48153 | nt. 651-3263 of SEQ ID NO: 411 |
| 412 | 2.00E−07 | REGULATORY PROTEIN CRO (ANTIREPRESSOR) | bacteriophage 434 | P03036 | compliment of nt. 59-259 of SEQ ID NO: 412 |
| 412 | 4.00E−06 | hypothetical protein | Bacteriophage P27 | CAC83535.1 | nt. 1436-1654 of SEQ ID NO: 412 |
| 413 | 8.00E−07 | hypothetical protein | *Deinococcus radiodurans* | NP_294301.1 | compliment of nt. 791-1012 of SEQ ID NO: 413 |
| 414 | 9.00E−65 | conserved hypothetical protein | *Vibrio cholerae* | NP_230092.1 | nt. 1696-2103 of SEQ ID NO: 414 |
| 414 | 3.00E−93 | unknown | *Pasteurella multocida* | NP_246834.1 | nt. 1777-2109 of SEQ ID NO: 414 |
| 416 | 2.00E−17 | unknown | *Pasteurella multocida* | NP_246629.1 | compliment of nt. 2565-2831 of SEQ ID NO: 416 |
| 416 | 4.00E−26 | hypothetical protein o154 | *Escherichia coli* | S30728 | compliment of nt. 1928-2254 of SEQ ID NO: 416 |
| 416 | 3.00E−37 | transport protein TatC | *Pseudomonas aeruginosa* | NP_253757.1 | compliment of nt. 1494-2018 of of SEQ ID NO: 416 |
| 417 | 1.00E−66 | weakly similar to methyltransferases | *Listeria innocua* | NP_471073.1 | compliment of nt. 999-1928 of SEQ ID NO: 417 |
| 417 | 5.00E−05 | DNA-BINDING PROTEIN RDGA | *Pectobacterium carotovorum* | Q47587 | compliment of nt. 3526-4212 of SEQ ID NO: 417 |
| 417 | 2.00E−29 | putative phage-related protein | *Yersinia pestis* | NP_407132.1 | compliment of nt. 2546-2938 of SEQ ID NO: 417 |
| 417 | 3.00E−06 | Adenine-specific DNA methylase | *Thermoplasma acidophilum* | NP_393798.1 | compliment of nt. 826-1020 of SEQ ID NO: 417 |
| 43 | 9.00E−16 | PcnB | *Pasteurella multocida* | NP_245801.1 | nt. 511-870 of SEQ ID NO: 43 |
| 434 | 2.00E−97 | beta' subunit of RNA polymerase | *Nephroselmis olivacea* | NP_050840.1 | compliment of nt. 32-1534 of SEQ ID NO: 434 |
| 435 | 4.00E−52 | MODIFICATION METHYLASE BEPI | *Brevibacterium epidermidis* | P10283 | compliment of nt. 11-565 of SEQ ID NO: 435 |
| 435 | 4.00E−57 | pentafunctional arom polypeptide (contains: 3-dehydroquinate synthase, 3-dehydroquinate dehydratase (3-dehydroquinase), shikimate 5-dehydrogenase, shikimate kinase, and epsp synthase) | *Saccharomyces cerevisiae* | NP_010412.1 | compliment of nt. 757-2064 of SEQ ID NO: 435 |
| 437 | 5.00E−70 | dihydrofolate reductase | *Haemophilus influenzae* (clinical isolate R1042) | S52336 | nt. 2393-2767 of SEQ ID NO: 437 |
| 438 | 1.00E−106 | polyA polymerase | *Vibrio cholerae* | NP_230244.1 | nt. 3-1124 of SEQ ID NO: 438 |
| 439 | 6.00E−60 | Porphyrin biosynthetic protein | *Salmonella enterica* subsp. *enterica* serovar Typhi | NP_457816.1 | nt. 2343-2783 of SEQ ID NO: 439 |

TABLE 3A-continued

| Contig | E score | Hit Identity | Organism | Genbank Protein | SEQ ID NO: |
|---|---|---|---|---|---|
| 441 | 5.00E−73 | RimM | *Pasteurella multocida* | NP_246234.1 | compliment of nt. 151-441 of SEQ ID NO: 441 |
| 442 | 9.00E−31 | LIPOPROTEIN NLPD | *Salmonella typhimurium* | P40827 | compliment of nt. 3362-3520 of SEQ ID NO: 442 |
| 444 | 6.00E−24 | glycine betaine transporter | *Staphylococcus aureus* subsp. *aureus* Mu50 | NP_371872.1 | compliment of nt. 2242-2514 of SEQ ID NO: 444 |
| 452 | 6.00E−28 | unknown | *Pasteurella multocida* | NP_245616.1 | compliment of nt. 533-883 of SEQ ID NO: 452 |
| 452 | 0 | Type I restriction enzyme Ecoprrl M protein | *Escherichia coli* | Q47163 | nt. 3291-4154 of SEQ ID NO: 452 |
| 452 | 2.00E−75 | type I restriction enzyme M protein | *Ureaplasma urealyticum* | NP_077929.1 | nt. 4156-4662 of SEQ ID NO: 452 |
| 455 | 9.00E−56 | PROBABLE BACTERIOPHAGE PROTEIN | *Ralstonia solanacearum* | NP_520059.1 | nt. 2028-2774 of SEQ ID NO: 455 |
| 455 | 2.00E−55 | orf2; similar to major capsid protein precursor of phage P2 (gene N), | *Haemophilus somnus* | AAC45158.1 | nt. 2864-3490 of SEQ ID NO: 455 |
| 455 | 1.00E−175 | gpP | *Enterobacteria phage P2* | NP_046758.1 | compliment of nt. 127-1812 of SEQ ID NO: 455 |
| 456 | 1.00E−38 | hypothetical protein | *Pseudomonas putida* | NP_542872.1 | compliment of nt. 1010-1282 of SEQ ID NO: 456 |
| 456 | 1.00E−172 | hypothetical protein | *Pseudomonas putida* | NP_542873.1 | compliment of nt. 1443-2006 of SEQ ID NO: 546 |
| 457 | 1.00E−116 | hypothetical protein (galE 5' region) - *Haemophilus influenzae* | *Haemophilus influenzae* | S15287 | compliment of nt. 62-961 of SEQ ID NO: 457 |
| 457 | 1.00E−134 | dTDPglucose 4,6-dehydratase | *Actinobacillus actinomycetemcomitans* | T00102 | nt. 2637-3656 of SEQ ID NO: 457 |
| 459 | 2.00E−10 | RNA polymerase gamma-subunit | *Synechocystis* sp. PCC 6803 | NP_441586.1 | nt. 25-117 of SEQ ID NO: 459 |
| 461 | 9.00E−51 | conserved hypothetical protein | *Staphylococcus aureus* subsp. *aureus* Mu50 | NP_370593.1 | nt. 4124-4624 of SEQ ID NO: 461 |
| 462 | 9.00E−06 | NADH dehydrogenase | *Burkholderia pseudomallei* | AAG01016.1 | nt. 703-828 of SEQ ID NO: 462 |
| 465 | 3.00E−41 | GTP-binding protein Era | *Synechocystis* sp. PCC 6803 | NP_441951.1 | compliment of nt. 2470-2787 of SEQ ID NO: 465 |
| 466 | 1.00E−15 | putative bacteriophage protein | *Salmonella enterica* subsp. *enterica* serovar Typhi | NP_455548.1 | nt. 837-1478 of SEQ ID NO: 466 |
| 466 | 1.00E−90 | orf31 | *Haemophilus phage HP1* | NP_043502.1 | nt. 2396-3199 of SEQ ID NO: 466 |
| 469 | 0 | Hemoglobin and hemoglobin-haptoglobin binding protein C precursor | *Haemophilus influenzae* HI689 | Q9X442 | compliment of nt. 427-3459 of SEQ ID NO: 469 |
| 471 | 8.00E−05 | transposase, putative | *Neisseria meningitidis* MC58 | NP_274608.1 | nt. 2957-3217 of SEQ ID NO: 471 |
| 472 | 6.00E−08 | hypothetical protein | *Salmonella enterica* subsp. *enterica* serovar Typhi | NP_458660.1 | compliment of nt. 2881-3270 of SEQ ID NO: 472 |
| 472 | 5.00E−23 | antirestriction protein | *Mesorhizobium loti* | NP_106707.1 | nt. 4908-5324 of SEQ ID NO: 472 |
| 472 | 1.00E−75 | hypothetical protein | *Salmonella enterica* subsp. *enterica* serovar Typhi | NP_458661.1 | compliment of nt. 1931-2776 of SEQ ID NO: 472 |
| 472 | 9.00E−72 | hypothetical protein | *Salmonella enterica* subsp. *enterica* serovar Typhi | NP_458662.1 | compliment of nt. 544-1689 of SEQ ID NO: 472 |

TABLE 3A-continued

| Contig | E score | Hit Identity | Organism | Genbank Protein | SEQ ID NO: |
|---|---|---|---|---|---|
| 475 | 3.00E−25 | unknown | Pasteurella multocida | NP_244952.1 | nt. 3207-3626 of SEQ ID NO: 475 |
| 476 | 8.00E−73 | putative DNA-binding protein | Salmonella enterica subsp. enterica serovar Typhi | NP_458175.1 | compliment of nt. 3339-4310 of SEQ ID NO: 476 |
| 476 | 6.00E−47 | anticodon nuclease | Neisseria meningitidis MC58 | NP_273873.1 | compliment of nt. 4397-4885 of SEQ ID NO: 476 |
| 478 | 3.00E−06 | methionin synthase-like enzyme | Arabidopsis thaliana | CAB38313.1 | compliment of nt. 3554-3679 of SEQ ID NO: 478 |
| 478 | 3.00E−05 | unknown | Pasteurella multocida | NP_245444.1 | compliment of nt. 164-250 of SEQ ID NO: 478 |
| 479 | 1.00E−18 | conserved hypothetical protein | Xylella fastidiosa 9a5c | NP_298841.1 | nt. 2302-2658 of SEQ ID NO: 479 |
| 48 | 3.00E−19 | Dca | Neisseria gonorrhoeae | AAF12796.1 | compliment of nt. 225-746 of SEQ ID NO: 48 |
| 482 | 1.00E−06 | hypothetical protein | Neisseria meningitidis MC58 | NP_275122.1 | nt. 2055-2189 of SEQ ID NO: 482 |
| 482 | 9.00E−28 | conserved hypothetical protein | Neisseria meningitidis MC58 | NP_274383.1 | nt. 1689-1898 of SEQ ID NO: 482 |
| 487 | 5.00E−75 | conserved hypothetical protein | Neisseria meningitidis Z2491 | NP_284304.1 | nt. 2541-2978 of SEQ ID NO: 487 |
| 488 | 2.00E−64 | unknown | Pasteurella multocida | NP_246617.1 | nt. 2983-3540 of SEQ ID NO: 488 |
| 488 | 8.00E−93 | 1-deoxy-D-xylulose 5-phosphate reductoisomerase | Zymomonas mobilis | AAD29659.1 | nt. 1344-1880 of SEQ ID NO: 488 |
| 491 | 5.00E−51 | rubredoxin oxidoreductase homolog | Clostridium acetobutylicum | AAB50346.1 | compliment of nt. 1690-2439 of SEQ ID NO: 491 |
| 492 | 1.00E−27 | phosphotransferase system enzyme IIA-like protein | Staphylococcus aureus | AAK83253.1 | compliment of nt. 755-970 of SEQ ID NO: 492 |
| 493 | 2.00E−84 | unknown | Actinobacillus actinomycetemcomitans | AAC70895.1 | nt. 3333-3935 of SEQ ID NO: 493 |
| 493 | 4.00E−49 | unknown | Helicobacter pylori J99 | NP_223898.1 | nt. 3345-4010 of SEQ ID NO: 493 |
| 493 | 9.00E−31 | transcriptional factor MdcH | Acinetobacter calcoaceticus | AAF20290.1 | nt. 1885-2793 of SEQ ID NO: 493 |
| 493 | 6.00E−30 | HimA | Pasteurella multocida | NP_245565.1 | nt. 1129-1260 of SEQ ID NO: 493 |
| 494 | 4.00E−85 | putative prophage integrase | Yersinia pestis | NP_404712.1 | nt. 900-2099 of SEQ ID NO: 494 |
| 494 | 4.00E−63 | DNA methyltransferase | Xylella fastidiosa 9a5c | NP_299063.1 | compliment of nt. 5544-6170 of SEQ ID NO: 494 |
| 494 | 6.00E−19 | MODIFICATION METHYLASE SCRFIA | Lactococcus lactis subsp. cremoris | P34877 | compliment of nt. 5019-6113 of SEQ ID NO: 494 |
| 497 | 0 | transferrin-binding protein 1 | Haemophilus influenzae (strain PAK 12085) | S70906 | nt. 3251-4999 of SEQ ID NO: 497 |
| 50 | 5.00E−07 | AcpP | Pasteurella multocida | NP_246856.1 | nt. 2-136 of SEQ ID NO: 50 |
| 501 | 7.00E−50 | conserved hypothetical protein | Vibrio cholerae | NP_231403.1 | compliment of nt. 3649-4872 of SEQ ID NO: 501 |
| 501 | 0 | type I restriction enzyme HsdR, putative | Vibrio cholerae | NP_231400.1 | compliment of nt. 1551-3440 of SEQ ID NO: 501 |
| 501 | 4.00E−13 | ATP-dependent DNA helicase RecG-related protein | Deinococcus radiodurans | NP_295921.1 | compliment of nt. 5317-5844 of SEQ ID NO: 501 |
| 501 | 5.00E−11 | conserved hypothetical | Ureaplasma urealyticum | NP_077868.1 | compliment of nt. 5098-5769 of SEQ ID NO: 501 |

TABLE 3A-continued

| Contig | E score | Hit Identity | Organism | Genbank Protein | SEQ ID NO: |
|---|---|---|---|---|---|
| 504 | 2.00E−44 | OUTER MEMBRANE PROTEIN P2 PRECURSOR (OMP P2) | *Haemophilus influenzae* AG30010 | Q48218 | compliment of nt. 4681-5019 of SEQ ID NO: 504 |
| 507 | 0 | SpoT | *Pasteurella multocida* | NP_245857.1 | compliment of nt. 3685-5316 of SEQ ID NO: 507 |
| 51 | 6.00E−87 | glucosamine--fructose-6-phosphate aminotransferase (isomerizing) | *Vibrio cholerae* | NP_230141.1 | nt. 30-470 of SEQ ID NO: 51 |
| 512 | 2.00E−28 | dipeptide transport system permease protein | *Yersinia pestis* | NP_407439.1 | compliment of nt. 1095-1580 of SEQ ID NO: 512 |
| 512 | 3.00E−82 | SapC | *Pasteurella multocida* | NP_245850.1 | compliment of nt. 730-1095 of SEQ ID NO: 512 |
| 514 | 9.00E−06 | putative integral membrane protein | *Campylobacter jejuni* | NP_281236.1 | compliment of nt. 577-684 of SEQ ID NO: 514 |
| 514 | 3.00E−11 | orf, hypothetical protein | *Escherichia coli* O157:H7 EDL933 | NP_286004.1 | compliment of nt. 449-568 of SEQ ID NO: 514 |
| 518 | 0 | putative inner membrane transacylase protein | *Neisseria meningitidis* Z2491 | NP_284893.1 | nt. 92-1927 of SEQ ID NO: 518 |
| 519 | 4.00E−30 | hypothetical protein | *Mesorhizobium loti* | NP_108196.1 | compliment of nt. 2221-3159 of SEQ ID NO: 519 |
| 519 | 2.00E−12 | conserved hypothetical protein | *Listeria innocua* | NP_471067.1 | compliment of nt. 3994-5241 of SEQ ID NO: 519 |
| 519 | 6.00E−20 | hypothetical protein | *Mesorhizobium loti* | NP_108198.1 | compliment of nt. 707-1552 of SEQ ID NO: 519 |
| 519 | 4.00E−26 | putative bacteriophage protein | *Salmonella enterica* subsp. *enterica* serovar Typhi | NP_455526.1 | compliment of nt. 3982-5163 of SEQ ID NO: 519 |
| 52 | 3.00E−94 | OUTER MEMBRANE PROTEIN P2 PRECURSOR (OMP P2) | *Haemophilus influenzae* | Q48218 | nt. 45-788 of SEQ ID NO: 52 |
| 520 | 0 | excision nuclease subunit A | *Escherichia coli* K12 | NP_418482.1 | compliment of nt. 6309-7745 of SEQ ID NO: 520 |
| 521 | 5.00E−08 | zinc/manganese ABC transporter substrate binding protein | *Rickettsia conorii* | NP_359651.1 | nt. 2236-2652 of SEQ ID NO: 521 |
| 521 | 1.00E−140 | unknown | *Pasteurella multocida* | NP_245865.1 | nt. 338-1390 of SEQ ID NO: 521 |
| 521 | 1.00E−86 | ORF_f432 | *Escherichia coli* | AAB40463.1 | nt. 203-1390 of SEQ ID NO: 521 |
| 522 | 3.00E−22 | unknown | *Pasteurella multocida* | NP_246093.1 | nt. 670-885 of SEQ ID NO: 522 |
| 526 | 5.00E−33 | exodeoxyribonuclease V alpha chain | *Yersinia pestis* | NP_404635.1 | nt. 5582-6202 of SEQ ID NO: 526 |
| 526 | 1.00E−62 | exodeoxyribonuclease V, 67 kDa subunit | *Vibrio cholerae* | NP_231950.1 | nt. 5675-6193 of SEQ ID NO: 526 |
| 527 | 1.00E−147 | unknown | *Pasteurella multocida* | NP_245980.1 | nt. 4283-5203 of SEQ ID NO: 527 |
| 527 | 0 | Mfd | *Pasteurella multocida* | NP_245978.1 | nt. 7545-8759 of SEQ ID NO: 527 |
| 527 | 0 | transcription-repair coupling factor (TrcF) | *Salmonella enterica* subsp. *enterica* serovar Typhi | NP_455708.1 | nt. 7611-8762 of SEQ ID NO: 527 |

TABLE 3A-continued

| Contig | E score | Hit Identity | Organism | Genbank Protein | SEQ ID NO: |
|---|---|---|---|---|---|
| 527 | 0 | PROBABLE TRANSCRIPTION-REPAIR COUPLING FACTOR PROTEIN | Ralstonia solanacearum | NP_519763.1 | nt. 7611-8870 of SEQ ID NO: 527 |
| 528 | 1.00E−48 | undecaprenyl pyrophosphate synthetase | Chlamydia muridarum | NP_297109.1 | nt. 2918-3712 of SEQ ID NO: 528 |
| 528 | 0 | leucyl-tRNA synthetase | Vibrio cholerae | NP_230603.1 | compliment of nt. 180-2822 of SEQ ID NO: 528 |
| 529 | 1.00E−104 | DNA PRIMASE | Legionella pneumophila | P71481 | compliment of nt. 3316-3960 of SEQ ID NO: 529 |
| 534 | 9.00E−29 | putative integrase | Salmonella typhimurium LT2 | NP_461690.1 | nt. 4668-5009 of SEQ ID NO: 534 |
| 534 | 6.00E−18 | hypothetical protein NMA0153 | Neisseria meningitidis Z2491 | NP_283002.1 | compliment of nt. 5933-6337 of SEQ ID NO: 534 |
| 534 | 2.00E−23 | hypothetical protein | Deinococcus radiodurans | NP_294868.1 | nt. 6908-7654 of SEQ ID NO: 534 |
| 534 | 1.00E−88 | prophage CP4-57 integrase | Escherichia coli K12 | NP_417111.1 | nt. 5057-5875 of SEQ ID NO: 534 |
| 535 | 1.00E−115 | phosphate acetyltransferase | Buchnera sp. APS | NP_240007.1 | nt. 3385-4596 of SEQ ID NO: 535 |
| 536 | 3.00E−35 | cobalt membrane transport protein CbiQ | Actinobacillus pleuropneumoniae | AAD49727.1 | compliment of nt. 3531-4136 of SEQ ID NO: 536 |
| 536 | 6.00E−37 | unknown | Pasteurella multocida | NP_245305.1 | compliment of nt. 6478-6921 of SEQ ID NO: 536 |
| 539 | 2.00E−26 | Orf122 | Chlorobium tepidum | AAG12204.1 | compliment of nt. 1778-2008 of SEQ ID NO: 539 |
| 540 | 1.00E−77 | heat shock protein HtpX | Neisseria meningitidis MC58 | NP_273864.1 | compliment of nt. 2567-3481 of SEQ ID NO: 540 |
| 541 | 0 | IleS | Pasteurella multocida | NP_246601.1 | nt. 3167-4549 of SEQ ID NO: 541 |
| 545 | 2.00E−09 | DNA-BINDING PROTEIN RDGB | Pectobacterium carotovorum | Q47588 | nt. 3816-3977 of SEQ ID NO: 545 |
| 545 | 2.00E−11 | putative transposase | Sinorhizobium meliloti | NP_437741.1 | compliment of nt. 2786-3019 of SEQ ID NO: 544 |
| 545 | 2.00E−07 | Hypothetical 42.5 kd protein in thrW-argF intergenic region | Escherichia coli | BAA77933.1 | compliment of nt. 2614-2811 of SEQ ID NO: 545 |
| 545 | 4.00E−18 | putative IS element transposase | Salmonella enterica subsp. enterica serovar Typhi | NP_454711.1 | nt. 1955-2230 of SEQ ID NO: 545 |
| 546 | 0 | HEME/HEMOPEXIN BINDING PROTEIN | Haemophilus influenzae | P45354 | nt. 5551-7809 of SEQ ID NO: 546 |
| 546 | 0 | HEME/HEMOPEXIN UTILIZATION PROTEIN B | Haemophilus influenzae | P45356 | nt. 3842-5536 of SEQ ID NO: 546 |
| 546 | 0 | HEME/HEMOPEXIN UTILIZATION PROTEIN C | Haemophilus influenzae | P45357 | nt. 1638-3176 of SEQ ID NO: 546 |
| 546 | 2.00E−12 | HasR | Pasteurella multocida | NP_246561.1 | nt. 3149-3763 of SEQ ID NO: 546 |
| 549 | 0 | unknown | Pasteurella multocida | NP_246821.1 | nt. 2526-3512 of SEQ ID NO: 549 |
| 549 | 1.00E−121 | putative membrane protein | Yersinia pestis | NP_404859.1 | nt. 605-1108 of SEQ ID NO: 549 |
| 549 | 0 | unknown | Pasteurella multocida | NP_246822.1 | nt. 1122-1664 of SEQ ID NO: 549 |
| 551 | 1.00E−157 | type I restriction-modification system endonuclease | Xylella fastidiosa 9a5c | NP_300016.1 | compliment of nt. 7396-8322 of SEQ ID NO: 551 |
| 552 | 1.00E−100 | valyl-tRNA synthetase | Deinococcus radiodurans | NP_293872.1 | compliment of nt. 6691-8688 of SEQ ID NO: 552 |

TABLE 3A-continued

| Contig | E score | Hit Identity | Organism | Genbank Protein | SEQ ID NO: |
|---|---|---|---|---|---|
| 552 | 0 | VALYL-TRNA SYNTHETASE | Haemophilus parainfluenzae | P36432 | compliment of nt. 5850-6647 of SEQ ID NO: 552 |
| 553 | 0 | DNA-directed RNA polymerase, beta subunit | Vibrio cholerae | NP_229982.1 | nt. 2668-6699 of SEQ ID NO: 553 |
| 554 | 0 | iron utilization protein B | Haemophilus influenzae | T10887 | nt. 991-2508 of SEQ ID NO: 554 |
| 559 | 1.00E−100 | PREPROTEIN TRANSLOCASE SECA SUBUNIT | Bacillus firmus | P96313 | nt. 3420-4472 of SEQ ID NO: 559 |
| 56 | 2.00E−23 | RpL30 | Pasteurella multocida | NP_246336.1 | compliment of nt. 656-832 of SEQ ID NO: 56 |
| 56 | 9.00E−13 | RpS5 | Pasteurella multocida | NP_246337.1 | compliment of nt. 843-1064 of SEQ ID NO: 56 |
| 560 | 1.00E−157 | Na+/H+ antiporter | Vibrio cholerae | NP_231535.1 | 2 compliment of nt. 279-2989 of SEQ ID NO: 560 |
| 562 | 1.00E−72 | putative biotin sulfoxide reductase 2 | Yersinia pestis | NP_404419.1 | nt. 7862-8878 of SEQ ID NO: 562 |
| 562 | 1.00E−125 | restriction modification system-R protein | Neisseria meningitidis | CAA09003.1 | nt. 2-985 of SEQ ID NO: 562 |
| 563 | 0 | IMMUNOGLOBULIN A1 PROTEASE | Haemophilus influenzae HK715 | P45384 | compliment of nt. 4127-9508 of SEQ ID NO: 563 |
| 563 | 0 | 3-ISOPROPYLMALATE DEHYDRATASE (IPMI) | Schizosaccharomyces pombe | O14289 | nt. 1980-3983 of SEQ ID NO: 563 |
| 564 | 2.00E−79 | orf32 | Haemophilus phage HP2 | NP_536839.1 | nt. 6241-6831 of SEQ ID NO: 564 |
| 564 | 7.00E−33 | probable variable tail fibre protein | Salmonella enterica subsp. enterica serovar Typhi | NP_457882.1 | nt. 3707-4177 of SEQ ID NO: 564 |
| 564 | 2.00E−14 | M protein | Enterobacteria phage 186 | NP_052264.1 | nt. 1905-2213 of SEQ ID NO: 564 |
| 564 | 4.00E−44 | similar to tail fiber protein (gpH) in phage P2 | Salmonella typhimurium LT2, Fels-2 prophage | NP_461635.1 | nt. 3171-3692 of SEQ ID NO: 564 |
| 564 | 2.00E−85 | gpJ | Enterobacteria phage P2 | NP_046773.1 | nt. 2267-3166 of SEQ ID NO: 564 |
| 564 | 1.00E−24 | hypothetical protein | Neisseria meningitidis Z2491 | NP_284534.1 | nt. 6852-7334 of SEQ ID NO: 564 |
| 564 | 4.00E−26 | gpV | Enterobacteria phage P2 | NP_046771.1 | nt. 1337-1912 of SEQ ID NO: 564 |
| 564 | 2.00E−47 | similar to [SwissProt P44255] | Escherichia coli | BAA16182.1 | nt. 11383-11961 of SEQ ID NO: 564 |
| 564 | 2.00E−51 | hypothetical protein NMA1315 | Neisseria meningitidis Z2491 | NP_284066.1 | nt. 10452-11180 of SEQ ID NO: 564 |
| 564 | 0 | orf31 | Haemophilus phage HP1 | NP_043502.1 | nt. 4160-6226 of SEQ ID NO: 564 |
| 564 | 2.00E−09 | rep | Haemophilus phage HP2 | NP_536816.1 | compliment of nt. 9986-10234 of SEQ ID NO: 564 |
| 565 | 2.00E−57 | resolvase/integrase-like protein | Haemophilus influenzae biotype aegyptius | AAL47097.1 | nt. 11885-12445 of SEQ ID NO: 565 |
| 565 | 1.00E−93 | integrase | Actinobacillus actinomycetemcomitans | AAC70901.1 | compliment of nt. 4118-4900 of SEQ ID NO: 565 |
| 565 | 6.00E−35 | probable phage integrase | Salmonella enterica subsp. enterica serovar Typhi | NP_458745.1 | compliment of nt. 4148-4990 of SEQ ID NO: 565 |
| 565 | 1.00E−107 | hypothetical protein | Xylella fastidiosa 9a5c | NP_299042.1 | compliment of nt. 5066-6817 of SEQ ID NO: 565 |

TABLE 3A-continued

| Contig | E score | Hit Identity | Organism | Genbank Protein | SEQ ID NO: |
|---|---|---|---|---|---|
| 566 | 1.00E−126 | hypothetical protein (galE 5′ region)- | Haemophilus influenzae | S15287 | compliment of nt. 10726-11607 of SEQ ID NO: 566 |
| 567 | 0 | unknown | Pasteurella multocida | NP_246387.1 | nt.5343-7688 of SEQ ID NO: 567 |
| 568 | 1.00E−151 | multidrug resistance membrane translocase | Escherichia coli O157:H7 | NP_311575.1 | nt. 6-1403 of SEQ ID NO: 568 |
| 568 | 1.00E−141 | YhbX/YhjW/YijP/YjdB family protein | Neisseria meningitidis MC58 | |NP_275002.1 | compliment of nt. 11213-12634 of SEQ ID NO: 568 |
| 570 | 1.00E−180 | hypothetical protein 3 (ksgA-lic2B intergenic region) | Haemophilus influenzae (strain RM7004) | S71024 | compliment of nt. 12845-13720 of SEQ ID NO: 570 |
| 571 | 0 | glycerophosphodiester phosphodiesterase | Haemophilus influenzae (isolate 772) | A43576 | nt. 1656-2693 of SEQ ID NO: 571 |
| 571 | 1.00E−137 | outer membrane protein P4 precursor - Haemophilus influenzae | Haemophilus influenzae | A43604 | nt. 6145-6909 of SEQ ID NO: 571 |
| 571 | 2.00E−72 | CG8298 gene product [alt 1] | Drosophila melanogaster | AAF58597.1 | nt. 3813-5339 of SEQ ID NO: 571 |
| 572 | 1.00E−40 | hypothetical protein TC0130 | Chlamydia muridarum (strain Nigg) | G81737 | nt. 3734-4099 of SEQ ID NO: 572 |
| 572 | 5.00E−10 | hypothetical protein | Pyrococcus horikoshii | NP_142215.1 | nt. 4472-4888 of SEQ ID NO: 572 |
| 572 | 3.00E−11 | 109aa long hypothetical protein | Sulfolobus tokodaii | NP_377117.1 | nt. 7303-7470 of SEQ ID NO: 572 |
| 572 | 8.00E−43 | hypothetical protein | Chlamydophila pneumoniae AR39 | NP_445524.1 | nt. 4289-4618 of SEQ ID NO: 572 |
| 572 | 9.00E−08 | CDH1-D | Gallus gallus | AAL31950.1 | nt. 7183-7521 of SEQ ID NO: 572 |
| 575 | 1.00E−173 | topoisomerase B | Salmonella enterica subsp. enterica serovar Typhi | NP_458624.1 | nt. 18980-20923 of SEQ ID NO: 575 |
| 575 | 1.00E−100 | DNA helicase | Salmonella enterica subsp. enterica serovar Typhi | NP_458617.1 | nt. 10399-11706 of SEQ ID NO: 575 |
| 65 | 2.00E−53 | SufI | Pasteurella multocida | NP_245041.1 | nt. 3-821 of SEQ ID NO: 65 |
| 67 | 4.00E−39 | putative MFS family tranport protein (1st mdule) | Salmonella typhimurium LT2 | NP_462786.1 | compliment of nt. 125-1033 of SEQ ID NO: 67 |
| 7 | 4.00E−29 | putative membrane protein | Salmonella enterica subsp. enterica serovar Typhi | NP_458664.1 | compliment of nt. 2-559 of SEQ ID NO: 7 |
| 72 | 2.00E−51 | serine transporter | Vibrio cholerae | NP_230946.1 | nt. 18-803 of SEQ ID NO: 72 |
| 74 | 3.00E−90 | hypothetical 21.8K protein (in locus involved in transformation)- | Haemophilus influenzae | JH0436 | compliment of nt. 248-766 of SEQ ID NO: 74 |
| 77 | 2.00E−18 | RecX protein | Legionella pneumophila | CAC33485.1 | nt. 480-920 of SEQ ID NO: 77 |
| 82 | 4.00E−95 | unknown | Pasteurella multocida | NP_246414.1 | nt. 128-955 of SEQ ID NO: 82 |
| 83 | 2.00E−66 | unknown | Pasteurella multocida | NP_246777.1 | nt. 5-556 of SEQ ID NO: 83 |
| 83 | 6.00E−33 | CTP SYNTHASE | Helicobacter pylori J99 | NP_223042.1 | compliment of nt. 1027-1338 of SEQ ID NO: 83. |
| 83 | 4.00E−34 | CTP synthase | Campylobacter jejuni | NP_281249.1 | compliment of nt. 1024-1275 of SEQ ID NO: 83 |
| 84 | 1.00E−16 | REPRESSOR PROTEIN CI | Bacteriophage phi-80 | P14819 | nt. 823-1233 of SEQ ID NO: 84 |

TABLE 3A-continued

| Contig | E score | Hit Identity | Organism | Genbank Protein | SEQ ID NO: |
|---|---|---|---|---|---|
| 84 | 2.00E−05 | orf, hypothetical protein | *Escherichia coli* K12 | NP_415875.1 | compliment of nt. 533-700 of SEQ ID NO: 84 |
| 84 | 4.00E−11 | orf33 | bacteriophage phi CTX | NP_490633.1 | compliment of nt. 32-466 of SEQ ID NO: 84 |
| 85 | 3.00E−42 | SpoT | *Pasteurella multocida* | NP_245857.1 | nt. 899-1261 of SEQ ID NO: 85 |
| 90 | 1.00E−103 | putative methylase | Bacteriophage Tuc2009 | NP_108695.1 | compliment of nt. 478-1206 of SEQ ID NO: 90 |
| 90 | 4.00E−11 | probable adenine specific DNA methyltransferase | *Thermoplasma acidophilum* | NP_394624.1 | compliment of nt. 397-1140 of SEQ ID NO: 90 |

TABLE 3B

| Hit Identity | Full Length Nucleotide Sequence | Amino Acid Sequence | Location in Contig | Homology to Genbank Protein |
|---|---|---|---|---|
| CpdB | SEQ ID NO: 686 | SEQ ID NO: 687 | nt. 38041-36068 of SEQ ID NO: 681 (contig 14) | NP_246953.1 |
| putative membrane protein | SEQ ID NO: 688 | SEQ ID NO: 689 | nt. 906601-908094 of SEQ ID NO: 685 (contig 18) | NP_458664.1 |
| GTP-binding protein TypA/BipA | SEQ ID NO: 690 | SEQ ID NO: 691 | nt. 42557-40995 of SEQ ID NO: 683 (contig 16) | NP_240245.1 |
| outer membrane protein A | SEQ ID NO: 692 | SEQ ID NO: 693 | nt. 7000420-704187 of SEQ ID NO: 685 (contig 18) | T30852 |
| vacB protein | SEQ ID NO: 694 | SEQ ID NO: 695 | nt. 39184-36836 of SEQ ID NO: 683 (contig 16) | NP_240369.1 |
| putative ABC transport system permease protein [ | SEQ ID NO: 696 | SEQ ID NO: 697 | nt. 59155-58370 of SEQ ID NO: 685 (contig 18) | NP_282774.1 |
| putative exported protein | SEQ ID NO: 698 | SEQ ID NO: 699 | nt. 901142-902542 of SEQ ID NO: 685 (contig 18) | NP_458655.1 |
| ImpA | SEQ ID NO: 700 | SEQ ID NO: 701 | nt. 348187-347747 of SEQ ID NO: 685 (contig 18) | NP_245829.1 |
| TsaA | SEQ ID NO: 702 | SEQ ID NO: 703 | nt. 74941-75548 of SEQ ID NO: 684 (contig 17) | NP_245732.1 |
| PROBABLE TRANSPORT TRANSMEMBRANE PROTEIN | SEQ ID NO: 704 | SEQ ID NO: 705 | nt. 74436-75176 of SEQ ID NO: 685 (contig 18) | NP_522358.1 |
| | SEQ ID NO: 706 | SEQ ID NO: 707 | nt. 75160-75660 of SEQ ID NO: 685 (contig 18) | |
| possible exported protein | SEQ ID NO: 708 | SEQ ID NO: 709 | nt. 899618-900262 of SEQ ID NO: 685 (contig 18) | NP_458653.1 |
| LICA PROTEIN | SEQ ID NO: 710 | SEQ ID NO: 711 | nt. 356917-355958 of SEQ ID NO: 685 (contig 18) | P14181 |
| HEME-BINDING PROTEIN A | SEQ ID NO: 712 | SEQ ID NO: 713 | NT. 26114-27739 of SEQ ID NO: 683 (contig 16) | P33950 |
| similar to BASEMENT MEMBRANE-SPECIFIC HEPARAN SULFATE PROTEOGLYCAN CORE PROTEIN PRECURSOR (HSPG) | SEQ ID NO: 714 | SEQ ID NO: 715 | nt. 311610-312683 of SEQ ID NO: 685 (contig 18) | XP_068727.1 |

TABLE 3B-continued

| Hit Identity | Full Length Nucleotide Sequence | Amino Acid Sequence | Location in Contig | Homology to Genbank Protein |
|---|---|---|---|---|
| CzcD | SEQ ID NO: 716 | SEQ ID NO: 717 | nt. 34865-35542 of SEQ ID NO: 681 (contig 14) | NP_246276.1 |
| conserved hypothetical protein | SEQ ID NO: 718 | SEQ ID NO: 719 | nt. 194993-193977 of SEQ ID NO: 685 (contig 18) | NP_274972.1 |
| secretion protein SecD | SEQ ID NO: 720 | SEQ ID NO: 721 | nt. 203707-201857 of SEQ ID NO: 683 (contig 17) | NP_252510.1 |
| ABC transporter protein 1 | SEQ ID NO: 722 | SEQ ID NO: 723 | nt. 3943-5859 of SEQ ID NO: 681 (contig 14) | AAF31030.1 |
| conserved hypothetical protein | SEQ ID NO: 724 | SEQ ID NO: 725 | nt. 331090-331749 of SEQ ID NO: 685 (contig 18) | NP_273467.1 |
|  | SEQ ID NO: 726 | SEQ ID NO: 727 | nt. 331938-332492 of SEQ ID NO: 685 (contig 18) |  |
|  | SEQ ID NO: 728 | SEQ ID NO: 729 | nt. 332681-33232 of SEQ ID NO: 685 (contig 18) |  |
| INVASIN PRECURSOR (OUTER MEMBRANE ADHESIN) | SEQ ID NO: 730 | SEQ ID NO: 731 | nt. 416757-417020 of SEQ ID NO: 685 (contig 18) | P31489 |
| HEME/HEMOPEXIN-BINDING PROTEIN | SEQ ID NO: 732 | SEQ ID NO: 733 | nt. 229430-232195 of SEQ ID NO: 384 (contig 17) | P45355 |
| OPACITY PROTEIN OPA66 PRECURSOR | SEQ ID NO: 734 | SEQ ID NO: 735 | nt. 375592-375879 of SEQ ID NO: 384 (contig 17) | Q05033 |
| Hemoglobin-haptoglobin binding protein A | SEQ ID NO: 736 | SEQ ID NO: 737 | nt. 45709-42566 of SEQ ID NO: 681 (contig 14) | Q48153 |
| transport protein TatC | SEQ ID NO: 738 | SEQ ID NO: 739 | nt. 134452-135222 of SEQ ID NO: 384 (contig 17) | NP_253757.1 |
| LIPOPROTEIN NLPD | SEQ ID NO: 740 | SEQ ID NO: 741 | nt. 18895-20112 of SEQ ID NO: 682 (contig 15) | P40827 |
| Hemoglobin and hemoglobin-haptoglobin binding protein C precursor | SEQ ID NO: 742 | SEQ ID NO: 743 | nt. 34181-31041 of SEQ ID NO: 682 (contig 15) | Q9X442 |
| HimA | SEQ ID NO: 744 | SEQ ID NO: 745 | nt. 382795-383085 of SEQ ID NO: 685 (contig 18) | NP_245565.1 |
| transferrin-binding protein 1 | SEQ ID NO: 746 | SEQ ID NO: 747 | nt. 178537-175799 of SEQ ID NO: 683 (contig 16) | S70906 |
| SapC | SEQ ID NO: 748 | SEQ ID NO: 749 | nt. 197754-196867 of SEQ ID NO: 685 (contig 18) | NP_245850.1 |
| heat shock protein HtpX | SEQ ID NO: 750 | SEQ ID NO: 751 | nt. 40414-41265 of SEQ ID NO: 682 (contig 15) | NP_273864.1 |
| HEME/HEMOPEXIN-BINDING PROTEIN | SEQ ID NO: 752 | SEQ ID NO: 753 | nt. 229430-232195 of SEQ ID NO: 684 (contig 17) | P45354 |
| HEME/HEMOPEXIN UTILIZATION PROTEIN B | SEQ ID NO: 754 | SEQ ID NO: 755 | nt. 227721-229418 of SEQ ID NO: 684 (contig 17) | P45356 |
| HEME/HEMOPEXIN UTILIZATION PROTEIN C | SEQ ID NO: 756 | SEQ ID NO: 757 | nt. 225516-227645 of SEQ ID NO: 684 (contig 17) | P45357 NP_246561.1 |
| iron utilization protein B | SEQ ID NO: 758 | SEQ ID NO: 759 | nt. 32076-33611 of SEQ ID NO: 684 (contig 17) | T10887 |
| PREPROTEIN TRANSLOCASE SECA SUBUNIT | SEQ ID NO: 760 | SEQ ID NO: 761 | nt. 82314-84785 of SEQ ID NO: 683 (contig 16) | P96313 |
| IMMUNOGLOBULIN A1 PROTEASE | SEQ ID NO: 762 | SEQ ID NO: 763 | nt. 171647-166263 of SEQ ID NO: 683 (contig 16) | P45384 |

TABLE 3B-continued

| Hit Identity | Full Length Nucleotide Sequence | Amino Acid Sequence | Location in Contig | Homology to Genbank Protein |
|---|---|---|---|---|
| multidrug resistance membrane translocase | SEQ ID NO: 764 | SEQ ID NO: 765 | nt. 74524-72992 of SEQ ID NO: 683 (contig 16) | NP_311575.1 |
| YhbX/YhjW/YijP/YjdB family protein | SEQ ID NO: 766 | SEQ ID NO: 767 | nt. 61734-63200 of SEQ ID NO: 683 (contig 16) | NP_275002.1 |
| putative membrane protein | SEQ ID NO: 768 | SEQ ID NO: 769 | nt. 906601-908094 of SEQ ID NO: 685 (contig 18) | NP_458664.1 |
| putative membrane protein | SEQ ID NO: 770 | SEQ ID NO: 771 | nt. 16185-17942 of SEQ ID NO: 683 (contig) | NP_404859.1 |

EXAMPLE 3

Construction of the NTHi Promoter Trap Library

To identify potential virulence determinants of NTHi, bacterial gene expression was monitored by differential fluorescence induction (DFI) during early disease progression in one specific anatomical niche of a chinchilla model of NTHi-induced otitis media (OM). Genomic DNA fragments from NTHi strain 86-028NP were cloned upstream of the promoterless gfpmut3 gene using a promoter trap library. Plasmid pGZRS39A, a derivative of pGZRS-1 isolated from *Actinobacillus pleuropneumoniae*, is an *A. pleuropneumoniae*-*Escherichia coli* shuttle vector. This plasmid contains the origin of replication from *A. pleuropneumoniae*, the lacZa gene from pUC19 and the kanamycin resistance gene from Tn903. (West et al., *Genes*, 160: 81-86, 1995).

The promoter trap vector was constructed by cloning the GTP mutant gfpmut3 gene, as a BamHI to EcoRI fragment into pGZRS-39A to form pRSM2167. This mutant GTP gene contains two amino acid changes. S65G and S72A, that enhance fluorescence emission when excited at 488 nm. This mutant also has high solubility and fast kinetics of chromophore formation (Cormack et al., *Gene*, 173: 33-38, 1996). This plasmid was transformed by electroporation into NTHi strain 86-028NP, generating the parent-plasmid strain 86-028NP/pRSM2169.

Random genomic DNA fragments (described in Example 1) were prepared for ligation into the promoter probe vector. Genomic DNA was isolated from strain 86-028NP using the Puregene DNA isolation kit (Gentra Systems, Minneapolis, Minn.) according to the manufacturer's protocol. Due to restriction barriers, it was necessary to isolate the plasmid DNA and use this for the library generation. The isolated DNA was partially digested with Sau3AI (NEB, Beverly, Mass.; 0.25 units/μg DNA) for 1 hour at 37° C., separated by gel electrophoresis and DNA fragments 0.5-1.5 kb in size were recovered using the Qiagen gel extraction kit. For vector preparation, pRSM2167 was isolated from an overnight culture using the Wizard Plus Maxiprep DNA purification system (Promega, Madison Wis.) according to the manufacturer's protocol.

Plasmid DNA was linearized by BamHI digestion and 5' phosphate groups removed by treatment with calf intestinal alkaline phosphatase (CIAP; GibcoBRL Life Technologies). Genomic DNA fragments were heated with the linearized, phosphatase-treated vector and electroporated into competent NTHi strain 86-028NT prepared for electroporation according to a modified protocol (Mitchell et al., *Nucleic Acids Res.*, 19: 3625-3628, 1991). When plasmid DNA was electroporated back into NTHi strain 86-028NP, transformation efficiency was improved by one-thousand fold. Briefly, cells were grown to an $OD_{600}$=0.3 in sBHI (brain heart infusion) broth at 37° C., 220 rpm. Cells were chilled on ice for 30 minutes and subsequently washed with an equal volume of 0.5×SG (1×SG: 15% glycerol, 272 mM sucrose) at 4° C. Washes were repeated a total of three times. Subsequently, the cells were diluted in 1×SG to a 100× concentrated volume. The cells were electroporated using the BioRad Gene Pulser II set at 200 ohms, 2.5 kV and 25 μF and then diluted in 1 ml prewarmed sBHI, incubated for 2 hours at 37° C., 5% $CO_2$ and plated on chocolate agar for overnight growth of transformants.

Transformants were selected and frozen in pools of 1000 clones in skim milk containing 20% glycerol (vol/vol). A 68,000 member gfp promoter probe library was generated. Using the probability calculation of Clarke and Carbon (*Cell*, 9: 91-90, 1976), to achieve 99% probability of having a given DNA sequence represented in a library of 300 bp fragments of strain 86-028NP DNA ($1.8×10^6$ bp/genome), a library of 27.629 clones was needed. Therefore the present library represents 2.5 fold coverage of the 86-028NP genome.

In order to assess the quality of the library, fifty clones were selected at random, grown overnight on chocolate agar and the plasmids were isolated and insert DNA sequenced. A majority (64%) of the selected clones had insert sizes ranging between 200 and 500 bp while 32% exceeded 500 bp. The majority of inserts showed homology to unique *H. influenzae* strain Rd open reading frames (ORFs), and 15 clones had sequence unique to strain 86-028NP DNA. Of those clones with homology to strain Rd, 60% were in the correct orientation, 36% of which contained sequence upstream an ORF. Although a majority of clones had an insert size less than 500 bp, no correlation was found between small insert size and increased GFP expression. In fact four clones exhibited slight to moderate fluorescence in vitro, 3 of which had insert sizes between 200-500 base pairs and one had an insert that was greater than 700 base pairs.

A fraction of the library (approximately 1000 clones) was grown on chocolate agar, harvested in PBS and analyzed by flow cytometry for GFP fluorescence. Compared to strain 86-028NP/pRSM2169 that contains the promoter trap vector without insert DNA, the pool of library clones displays an increased fluorescence intensity. Thus, the library contains clones with promoters at varying levels of activity.

EXAMPLE 4

Analysis of 86-028NP Derivatives Expressing GFP

In order to establish the FACS parameters necessary to identify and sort gfp-expressing bacteria, a panel of isolates demonstrating varying levels of gfp expression was utilized. Background fluorescence was assessed using strain 86-028NP/pRSM2169 (negative control), therefore any observed fluorescence would be due to the lacZ promoter driving gfp expression. However, this strain does not produce detectable levels of GFP and in fact, does not demonstrate increased fluorescence when compared to the parent strain 86-028NP. A high-level gfp-expressing isolate was generated by cloning a 500 bp fragment containing the strong promoter for outer membrane protein P2 expression into SalI-BamHI digested pRSM2167. This plasmid was transformed into 86-028SNP by electroporation. generating the high-level gfp expressing strain 86-028NP/pRSM2211 (highly fluorescent control). This strain demonstrated an approximate 100 fold increase in GFP fluorescence compared to strain 86-028NP/pRSM2169. An intermediate fluorescent derivative clone. 86-028NP/pKMM4B5 (intermediate fluorescent control), was isolated by FACS analysis and used both in preliminary experiments and as a control for cell sorting. The DNA fragment containing a promoter driving gfp expression in vitro is unique to strain 86-028NP, having no known homology to DNA of other organisms. This clone exhibits an approximate 10 fold increase in fluorescence compared to strain 86-028NP/pRSM2169.

The control strains were resuspended from growth on chocolate agar and labeled with cross-reactive Phycoprobe R-PE anti-human IgG (H+L) antibody (10 g/ml in 100 1 PBS; Biomeda Corp) for 30 minutes at 4° C. Following three successive washes to remove unbound antibody, bacteria were resuspended in 300 1 Dulbecco's Phosphate Buffered Saline (DPBS) DPBS for FACS analysis. These control preparations were used to set the appropriate size and fluorescence gates using a Coulter Epics Elite flow cytometer (Coulter Corp.) equipped with an argon laser emitting at 488 nm. Bacteria were gated for size based on log forward angle and side scatter detection and for sorting by FITC/PE labeling of bacteria. Sorted cells were collected into cold sBHI and plated on chocolate agar. After overnight growth, cells were collected for a secondary round of infection or were individually selected and grown overnight, screened by individual clone for fluorescence when grown in vitro, and frozen in skim milk containing 20% (vol/vol) glycerol prior to plasmid isolation and sequencing of insert DNA. Sorting efficiency of control strains was confirmed using a Coulter EPICS flow cytometer (Coulter Corp.).

Many plasmids were segregated rapidly in vitro in the absence of antibiotic selection. Thus, in order to assess whether the promoter trap vector used here was prone to this event, a single colony of strain 86-028NP/pRSM2211 (highly fluorescent control) was isolated on chocolate agar and passaged 20 times in the absence of antibiotic selection. No significant decrease in fluorescence intensity was observed when compared to bacteria grown in the presence of antibiotic. In addition, the plasmid is maintained in the absence of antibiotic selection in vivo. Similar bacterial counts were observed when bacteria-containing middle ear fluids collected from a chinchilla were plated on chocolate agar with or without kanamycin. These data demonstrate that the promoter trap vector was stably maintained in the absence of antibiotic selection.

In addition to problems with plasmid stability, early studies on the use of GFP as a reporter to study host-pathogen interactions demonstrated that GFP could be continuously synthesized as a cytoplasmic protein with low toxicity, having minimal effects on the bacterial cell-surface dynamics (Chalfie et al., Science, 263: 802-805, 1994). The construction of a high level gfp-expressing derivative allowed the assessment of the GFP toxicity on NTHi. Growth curves of both the wild-type strain (86-028NP) and the high GFP producing strain 86-028NP/pRSIM2211 were compared when grown under similar conditions. The growth rates were similar, indicating that GFP expression was not toxic to the cells.

The 86-028NP gfp-expressing derivatives were used to define the parameters for efficient cell sorting. Strain 86-028NP/pRSM2169 was mixed with the intermediate gfp-expressing derivative, strain 86-028NP/pKMM4B5, at a 100:1 ratio, simulating the in vivo environment that is expected to contain a small percentage of gfp-expressing clones relative to the total bacterial population. This mixture was subjected to FACS analysis, collecting the 1.8% most fluorescent population and the 52% least fluorescent population. Flow cytometric analysis of the sorted populations revealed an enrichment of strain 86-028NP/pKIMM4B5 to 65% of the bacterial population, a phenomenon that was not observed when sorting on the negative population. Subsequent rounds of sorting would be expected to further enrich for this intermediate fluorescent population. The inability to decrease the amount of fluorescent bacteria in the negative sort was attributed to the size of the gate set for negative sorting. GFP-negative cells were enriched by gating on the 10% least fluorescent population.

EXAMPLE 5

Direct Labeling of Bacteria From Middle Ear Fluids

A similar strategy (as described in Example 5) was applied to sort fluorescent clones from effusions obtained from the chinchilla middle ear during AOM. Our ability to use differential fluorescence induction (DFI) in vivo was dependent upon our ability to sort gfp-expressing bacteria from non-fluorescent bacteria, fluorescent and non-fluorescent cellular debris, and eukaryotic cells.

Healthy adult chinchillas (*Chinchilla lanigera*) with no evidence of middle car infection by either otoscopy or tympanometry were used to screen the library for promoter activity in viva. Two pools of the NTHi/pRSM2169 library (1000 clones each) were grown overnight on chocolate agar containing kanamycin. The library was combined and diluted in cold 10 mM sterile PBS to $3.3 \times 10^6$ and 300 µl ($1.0 \times 10^6$ CFU; 500 CFU/clone) was used to inoculate the left and the right chinchilla transbullar cavity (2000 clones/ear). OM development was monitored by video otoscopy and tympanometry at 24 and 48 hours. The bacteria multiplied in the middle ear cavity, reaching a concentration 500 times the inoculum dose by 48 hours as expected (Bakaletz et al., *Infect. Immunity* 67: 2746-62, 1999). This bacterial adaptation to the host environment results in an inflammatory response, indicated by erythema, vessel dilation and bulging of the tympanic membrane, infiltration of polymorphonuclear cells (PMN's), and accumulation of fluid in the middle ear cavity as observed by otoscopy and microscopic examination of recovered effusions. Twenty-four and 48 hours later, middle ear fluids were retrieved by epitympanic tap, and prepared for FACS.

It is important to note that this analysis vas limited to those bacteria recoverable in the middle ear fluid. In some cases it was necessary to lavage the middle ear cavity to collect the bacteria for FACS analysis. Thus, this analysis includes genes up-regulated when NTHi are loosely adherent to mucosae. NTHi has been observed to form a biofilm in the middle ear cavity in a chinchilla model of OM (Erhlich et al., *JAMA*, 287: 1710-5, 2002). Since the protocols described herein select for clones recovered from the planktonic population, it is not expected to recover those clones in which genes are upregulated when the bacteria are associated with mucosal biofilms. Homogenization of middle ear mucosae and subsequent bacterial cell isolation however, would enable us to recover these clones. It is also possible that some GFP-expressing clones were recovered in the effusion, yet were adherent to eukaryotic cells present in the effusion as exfoliated cells, or in agoregates. These bacteria are difficult to recover from the effusion without compromising the sorting efficiency. Therefore the middle ear fluids were treated with a mucolytic agent, then centrifuged to remove large aggregates and eukaryotic cells and prior to labeling.

Chinchilla middle ear fluids were diluted, if necessary, to 250 µl with sterile saline. An equal volume of N-acetyl-L-cysteine (0.5%; w/v) in DPBS (pH 7.4) was added for 5 minutes at room temperature as a mucolytic agent (Miyamoto and Bakaletz, *Microb. Pathog.*, 21: 343-356 1906). Fluids were centrifuged (300×g, 5 min) to remove cellular debris, red blood cells and inflammatory cells, and supernatants containing bacteria were transferred to a fresh tube. Bacteria were incubated with chinchilla antiserum (1:50 dilution) directed against a whole OMP preparation, derived from NTHi strain 86-028NP, for 45 minutes at 4° C., pelleted by centrifugation (2000×g, 5 mm) washed twice with cold DPBS containing 0.05% bovine serum albumin. Bacteria were subsequently labeled with cross-reactive phycoprobe R-PE anti-human IgG (H+L) antibody (10 µg/ml in 100 µl PBS; Biomeda Corp) for 30 minutes at 4° C. Following three successive washes to remove unbound antibody, cells were resuspended in 300 al DPBS for FACS analysis.

EXAMPLE 6

Identification of Promoters Induced In Vivo in Acute Otitis Media

*H. influenzae* 86-028NP transformed with the promoter trap library was grown overnight on chocolate agar. To select against those clones containing promoters that expressed gfp in vitro, the library was subjected to one round of FACS analysis (as described in Example 6), collecting only those clones expressing low-level amounts of GFP. These clones were pooled and used to inoculate the chinchilla middle ear transbullarly. Following 24 and 48 hours of infection, bacteria-containing effusions were removed by epitympanic tap. Bacteria were indirectly labeled with R-PE-labeled antibody and subjected to FACS analysis by gating on fluorescently tagged bacteria but sorting for those that were also expressing. These clones were used to reinfect animals for further enrichment. Following the final round of sorting, single colony isolates were screened in vitro for lack of fluorescence.

Those clones isolated by FACS analysis (positive for GFP fluorescence in vivo), which did not emit fluorescence in vitro were prepared for plasmid isolation and identification of insert DNA sequence. These clones were grown overnight on chocolate agar plates containing kanamycin and prepared for plasmid isolation using the Qiaprep Miniprep Kit (Qiagen) according to the manufacturer's protocol. Plasmid insert DNA was sequenced using the primer 5'-TGCCCATTAA-CATCACCATCTA-3' (SEQ ID NO: 588) that is complementary to the gfpmut 3 gene and downstream of the insert DNA. Sequencing reactions were performed using the ABI prism BigDye® terminator cycle sequencing ready reaction kit (Applied Biosystems) according to manufacturer's protocol using a GeneAmp PCR System 9700 (Applied Biosystems). The sequences were then purified by passage through sephadex G-50 in a 96-well multiscreen HV plate (Millipore) and subsequently analyzed on an ABI Prism 3100 DNA analyzer (Applied Biosystems).

Insert sequences were compared to the complete annotated sequence of *H. influenzae* strain Rd. Those inserts with no nucleotide homology to strain Rd were subsequently analyzed using the BLASTN and BLASTX algorithms. Further sequence analysis was performed with DNASTAR (Madison, Wis.). Inserts in the correct orientation and containing sequence 5' to a predicted ORF contained a putative promoter that was preferentially active when the NTHi bacteria were in the chinchilla middle ear.

Fifty-two clones with putative promoters that were regulated in vivo were isolated. Of the 44 candidate clones containing sequence similar to that identified in *H. influenzae* strain Rd, quantitative comparison of gene expression in vitro and in two confirmed up-regulated gene expression for twenty-six genes (60%) when NTHi respond to environmental cues present in the chinchilla middle ear and these genes are summarized in Table 4A below. The in vivo-regulated promoters driving expression of genes are predicted to be involved in membrane transport, environmental informational processing, cellular metabolism, gene regulation, as well as hypothetical proteins with unknown function.

In order to confirm the induction of putative promoter candidates in vivo, the relative amount of messenger RNA expression was compared when NTHi strain 86-028NP was grown in vitro to mid-log phase or in vivo for 48 hours. The RNA was isolated using TRIzol LS reagent (Gibco Life Technologies) according to the manufacturer's protocol. DNA was removed from the RNA preparation using DNA-free kit (Ambion) according to the manufacturer's protocol. DNase I treated RNA samples were purified by passage through a Qiagen RNeasy column. RNA purity and integrity was assessed by 260/280 nm spectrophotometer readings and on the Agilent 2100 Bioanalyzer (Agilent Technologies), respectively.

In order to independently confirm the FACS data, we determined the relative expression of candidate genes by quantitative RT-PCR. The parent strain 86-028NP, was used for these studies. Real-time quantitative RT-PCR using the one-step QuantiTect SYBR Green RT-PCR kit (Qiagen) assessed transcription levels according to the manufacture's instructions. Briefly, using primers generated to an open reading frame downstream of the putative in vivo-induced promoters identified by FACS analysis, gene-specific mRNA was reverse transcribed and amplified by RT-PCR on the ABI Prism 7700 sequence detection system (Applied Biosystems). The amount of product was calculated using a standard curve generated to known amounts of bacterial genomic DNA ($10^2$-$10^7$ genomic copies DNA) by amplifying a fragment of the gyrase (gyr) gene. Controls were analyzed in parallel to verify the absence of DNA in the RNA preparation (-RT control) as well as the absence of primer dimers in control samples lacking template RNA. In addition, RT-PCR products were analyzed by gel electrophoresis and, in all cases, a single product was observed at the appropriate base pair size. Amounts of bacterial RNA between samples were normalized relative to gyr expression, shown to be constitutively expressed under various growth conditions that we tested in vitro. Known amounts of bacterial genomic DNA ($10^2$-$10^7$ genomic copies DNA) were used to generate a standard curve for RT-PCR quantitation by amplifying a fragment of the gyrase (gyr) gene. Gyrase is constitutively expressed in vitro under various growth conditions and was therefore used to normalize total bacterial RNA levels between samples. Relative gene expression in vivo was compared to that of gene expression in vitro and data expressed as fold-increase are summarized in Table 4A.

The 8-fold sequencing of the NTHi genome identified the full length open reading frames for the majority of genes listed in Table 4A. Table 4B provides the full length nucleotide sequence within the NTHi genome and the corresponding amino acid sequence. The fold induction of the gene due to environmental cues present in the chinchilla middle ear and the product or function of the gene are repeated in Table 4B for convenience.

TABLE 4A

| Category | Gene or ORF | SEQ ID NO: | GenBank Protein ID | Fold Induction | Product or Function |
|---|---|---|---|---|---|
| Amino acid metabolism | hisB | 589 | NP_438632 | 2.9 | Histidine biosynthesis bifunctional protein |
| Lipoprotein | lppB | 590 | NP_438862.1 | 2.6 | Lipoprotein B homologue |
| Membrane transport | sapA | 591 | NP_439780.1 | 2.8 | Peptide ABC transporter; periplasmic SapA precursor |
|  | lolA | 592 | NP_439736.1 | 2.4 | Outer membrane lipoproteins carrier protein precursor |
|  | rbsC | 593 | NP_438661.1 | 5.1 | Ribose transport system permease protein |
| Purine synthesis | purE | 594 | NP_439757.1 | 51.7 | Phosphoribosylaminoimidazole carboxylase catalytic subunit; PurE |
| Biosynthetic and metabolic functions | ribB | 595 | NP_438923.1 | 8.3 | 3,4-dihydroxy-2-butanone 4-phosphate synthase; riboflavin biosynthesis |
|  | arcB | 596 | NP_438753.1 | 10 | Ornithine carbamolytransferase; arginine degradation |
|  | uxuA | 597 | NP_438228.1 | 3.1 | Mannonate dehydratase; production of glyceraldehyde 3-phosphate |
|  | dsbB | 598 | NP_438589.1 | 2.6 | Disulfide oxidoreductase; disulfide bond formation protein B |
|  | ureH | 599 | NP_438693.1 | 3.9 | Urease accessory protein |
|  | licC | 600 | NP_439688.1 | 2.3 | Phosphocholine (ChoP) cytidylyltransferase |
|  | HI1647 | 601 | NP_439789.1 | 2.0 | Putative pyridoxin biosynthesis protein; singlet oxygen resistance protein |
| DNA replication, repair | ispZ | 602 | P43810 | 2.5 | Probable intracellular septation protein |
|  | radC | 603 | NP_439113.1 | 2.1 | DNA repair protein |
|  | mukF | 604 | P45185 | 2.0 | MukF protein homologue; remodeling of nucleiod structure |
| Gene regulation | glpR | 605 | NP_438777.1, NP_439170.1 | 2.8 | Glycerol-3-phosphate regulon repressor |
|  | ihfB | 606 | P43724 | 2.5 | Integration host factor beta subunit |
|  | argR | 607 | NP_439365.1 | 2.7 | Arginine repressor |
|  | cspD | 608 | NP_439584.1 | 2.1 | Cold shock like protein; stress response protein |
| Hypothetical or unknown proteins | HI0094 | 609 | NP_438267.1 | 8.3 | Hypothetical protein |
|  | HI1163 | 610 | NP_439321.1 | 2.3 | Conserved hypothetical protein; putative oxidase |
|  | HI1063 | 611 | NP_439221.1 | 2.7 | Hypothetical protein |
|  | HI0665 | 612 | NP_438824.1 | 2.8 | Hypothetical protein |
|  | HI1292 | 613 | NP_439444.1 | 2.6 | Hypothetical protein |
|  | HI1064 | 614 | NP_439222.1 | 2.6 | Hypothetical protein |

TABLE 4B

| Category | Gene or ORF | Full Length Nucleotide Sequence | Amino Acid Sequence | Location in Contig | Fold Induction | Product or Function |
|---|---|---|---|---|---|---|
| Amino acid metabolism | hisB | SEQ ID NO: 615 | SEQ ID NO: 616 | nt. 68378-67290 of SEQ ID NO: 680 (contig 13) | 2.9 | Histidine biosynthesis bifunctional protein |

TABLE 4B-continued

| Category | Gene or ORF | Full Length Nucleotide Sequence | Amino Acid Sequence | Location in Contig | Fold Induction | Product or Function |
|---|---|---|---|---|---|---|
| Membrane transport | sapA | SEQ ID NO: 617 | SEQ ID NO: 618 | nt. 200403-198709 of SEQ ID NO: 685 (contig 18) | 2.8 | Peptide ABC transporter; periplasmic SapA presursor |
|  | rbsC | SEQ ID NO: 619 | SEQ ID NO: 620 | nt. 42773-41802 of SEQ ID NO: 680 (contig 13) | 5.1 | Ribose transport system permease protein |
| Purine synthesis | purE | SEQ ID NO: 621 | SEQ ID NO: 622 | nt. 219625-219131 of SEQ ID NO: 685 (contig 18) | 51.7 | Phosphoribosyl-aminoimidazole carboxylase catalytic subunit; PurE |
| Biosynthetic and metabolic functions | ribB | SEQ ID NO: 623 | SEQ ID NO: 624 | no. 131537-132184 of SEQ ID NO: 682 (contig 15) | 8.3 | 3,4-dihydroxy-2-butanone 4-phosphate synthase; raboflavin biosynthesis |
|  | arcB | SEQ ID NO: 625 | SEQ ID NO: 626 | nt. 49710-48706 of SEQ ID NO: 681 (contig 14) | 10 | Ornithine carbamolytrans-ferase; arginine degradation |
|  | uxuA | SEQ ID NO: 627 | SEQ ID NO: 628 | nt. 840671-841855 of SEQ ID NO: 685 (contig 18) | 3.1 | Mannonate dehydratase; production of glyceraldehyde 3-phosphate |
|  | dsbB | SEQ ID NO: 629 | SEQ ID NO: 630 | nt. 388050-388583 of SEQ ID NO: 384 (contig 17) | 2.6 | Disulfide oxidoreductase; disulfide bond formation protein B |
|  | ureH | SEQ ID NO: 631 | SEQ ID NO: 632 | nt. 4452-5267 of SEQ ID NO: 680 (contig 13) | 3.9 | Urease accessory protein |
|  | licC | SEQ ID NO: 633 | SEQ ID NO: 634 | nt. 355083-354382 of SEQ ID NO: 385 (contig 18) | 2.3 | Phosphochlorine (ChoP) cytidylyltransferase |
|  | HI1647 | SEQ ID NO: 635 | SEQ ID NO: 636 | nt. 664017-664892 of SEQ ID NO: 685 | 2.0 | Putative pyridoxin biosynthesis protein; singlet oxygen resistance protein |
| DNA replication, repair | ispZ | SEQ ID NO: 637 | SEQ ID NO: 638 | nt. 4512-5069 of SEQ ID NO: 683 (contig 16) | 2.5 | Probable intracellular septation protein |
|  | radC | SEQ ID NO: 639 | SEQ ID NO: 640 | nt. 132695-132030 of SEQ ID NO: 683 (contig 16) | 2.1 | DNA repair protein |
|  | mukF | SEQ ID NO: 641 | SEQ ID NO: 642 | nt. 504549-503215 of SEQ ID NO: 685 (contig 18) | 2.0 | MukF protein homologue; remodeling of nucleiod structure |
| Gene regulation | glpR | SEQ ID NO: 643 | SEQ ID NO: 644 | nt. 72716-73483 of SEQ ID NO: 682 (contig 15) | 2.8 | Glycerol-3-phosphate regulon repressor |
|  | thfB | SEQ ID NO: 645 | SEQ ID NO: 646 | nt. 661004-660720 of SEQ ID NO: 685 (contig 18) | 2.5 | Integration host factor beta subunit |
|  | argR | SEQ ID NO: 647 | SEQ ID NO: 648 | nt. 178540-178085 of SEQ ID NO: 685 (contig 18) | 2.7 | Arginine repressor |
|  | cspD | SEQ ID NO: 649 | SEQ ID NO: 650 | nt. 435310-435528 of SEQ ID NO: 685 (contig 18) | 2.1 | Cold shock like protein; stressa response protein |
| Hypothetical or unknown proteins | HI1163 | SEQ ID NO: 651 | SEQ ID NO: 652 | nt. 137202-134119 of SEQ ID NO: 685 (contig 18) | 2.3 | Conserved hypothetical protein; putative oxidase |
|  | HI1063 | SEQ ID NO: 653 | SEQ ID NO: 654 | nt. 35158-34937 of SEQ ID NO: 685 (contig 18) | 2.7 | Hypothetical protein |

TABLE 4B-continued

| Category | Gene or ORF | Full Length Nucleotide Sequence | Amino Acid Sequence | Location in Contig | Fold Induction | Product or Function |
|---|---|---|---|---|---|---|
| | HI0665 | SEQ ID NO: 655 | SEQ ID NO: 656 | nt. 17949-18980 of SEQ ID NO: 679 (contig 12) | 2.8 | Hypothetical protein |
| | HI1292 | SEQ ID NO: 657 | SEQ ID NO: 658 | nt. 555002-555799 of SEQ ID NO: 685 (contig 18) | 2.6 | Hypothetical protein |

EXAMPLE 7

Identification of Virulence-Associated Genes

In many bacterial species, a subset of virulence-associated genes is regulated by errors in replication of short repeats. These repeats may be 5' to a gene or in the coding sequence, and their presence is an indication of controlled expression of the gene, which indicates association with virulence. Addition or deletion of a repeat results in the expression or of lack of expression of the particular virulence determinant.

The NTHi *H. influenzae* strain 86-028NP contig set was queried for short oligonucleotide repeats. The region surrounding the repeats was analyzed to identify the gene(s) associated with the repeat. Table 5 lists the identified repeats and the ORF (identified by BLAST) associated with each repeat.

Further sequence analysis has identified the full length nucleon sequence of the virulence-associated genes and the corresponding amino acid sequences encoded by the ORF. The derived an acid sequences are highly homologous to the listed Genbank sequence.

TABLE 5

| Repeat | Location in 3-fold Contigs | Location in 8-fold Contigs | Full Length Nucleotide Sequence | Amino Acid Sequence | Genebank Accession No. |
|---|---|---|---|---|---|
| SEQ ID NO: 581 | 115 nt. 473-540 of SEQ ID NO: 115 | nt. 484533-483643 of SEQ ID NO: 685 (contig 18) | SEQ ID NO: 659 | SEQ ID NO: 660 | NP_439538.1 |
| SEQ ID NO: 582 | 377 nt. 546-597 of SEQ ID NO: 337 | nt. 416274-414910 of SEQ ID NO: 685 (contig 18) | SEQ ID NO: 661 | SEQ ID NO: 662 | P45217 |
| SEQ ID NO: 583 | 505 nt. 310-393 of SEQ ID NO: 505 | nt. 414500-416614 of SEQ ID NO: 684 (contig 17) | SEQ ID NO: 663 | SEQ ID NO: 664 | AAK76425 |
| SEQ ID NO: 584 | 508 nt. 2079-2120 of SEQ ID NO: 508 | nt. 506516-507913 of SEQ ID NO: 685 (contig 18) | SEQ ID NO: 665 | SEQ ID NO: 666 | NP_439520 |
| SEQ ID NO: 585 | 518 nt. 758-789 of SEQ ID NO: 518 | nt. 354274-352406 of SEQ ID NO: 684 (contig 17) | SEQ ID NO: 667 | SEQ ID NO: 668 | NP_284893 |
| SEQ ID NO: 586 | 543 nt. 1814-196 of SEQ ID NO: 543 | nt. 347864-243236 of SEQ ID NO: 685 (contig 18) | SEQ ID NO: 669 | SEQ ID NO: 670 | AAA20524 |
| SEQ ID NO: 586 | 543 nt. 1814-196 of SEQ ID NO: 543 | nt. 699709-704187 of SEQ ID NO: 685 (contig 18) | SEQ ID NO: 671 | SEQ ID NO: 672 | AAD56660 |
| SEQ ID NO: 587 | 567 nt. 13309-13320 of SEQ ID NO: 567 | nt. 85546-84689 of SEQ ID NO: 681 (contig 14) | SEQ ID NO: 673 | SEQ ID NO: 674 | ZP_00053190 |

EXAMPLE 8

Identification of Unique NTHi Gene Sequences

Genes associated with NTHi virulence were also identified by comparing the level of expression of the gene when the NTHi bacterium was infecting a tissue verses the level of expression of the same gene when the NTHi was grown on artificial laboratory media. These novel genes were identified using the promoter trap techniques described above in Examples 4-6, and subsequently comparisons with the known Rd genome demonstrated these genes are unique to NTHi strain 86-028NP.

The DNA sequence identified using this screening procedure are set forth as SEQ ID NOS: 577-580. These sequences did not contain genes or gene fragments that have homologues in the *H. influenzae* Rd, genome sequence. Even though these are completely novel sequences, due to their expression level during NTHi infection in the chinchilla middle ear, it is likely that expression of these genes are involved in NTHi virulence.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08236494B2). An electronic copy of the "Sequence Listing" will also be available from the USPTO upon request and payment of the fee set forth in 37 CFR 1.19(b)(3).

---

What is claimed:

1. An isolated polynucleotide comprising the nucleotide sequence of SEQ ID NO: 590.

2. A method for detecting NTHi bacteria in a biological sample comprising
    (a) contacting a polynucleotide of claim 1 with polynucleotides from a biological sample under stringent hybridization conditions, wherein the hybridization conditions comprise washing with 0.015 M sodium chloride, 0.0015 M sodium citrate at 65-68° C., and
    (b) detecting hybridization of the polynucleotide within the sample, wherein hybridization indicates the presence of NTHi bacteria in the biological sample.

3. The method of claim 2 wherein the biological sample is selected from the group consisting of serum, sputum, ear fluid, blood, urine, lymphatic fluid, and cerebrospinal fluid.

4. A vector comprising the polynucleotide of claim 1.

5. The vector of claim 4, wherein the polynucleotide is operatively linked to an expression control sequence.

6. An isolated cell comprising the vector of claim 4.

7. A host cell comprising the vector of claim 5.

8. An isolated cell comprising the polynucleotide of claim 1.

* * * * *

UNITED STATES PATENT AND TRADEMARK OFFICE
CERTIFICATE OF CORRECTION

| | | |
|---|---|---|
| PATENT NO. | : 8,236,494 B2 | Page 1 of 1 |
| APPLICATION NO. | : 13/187989 | |
| DATED | : August 7, 2012 | |
| INVENTOR(S) | : Lauren O. Bakaletz et al. | |

It is certified that error appears in the above-identified patent and that said Letters Patent is hereby corrected as shown below:

In the Specification:

At column 1, line 17 insert

--Part of the work during the development of this invention was made with government support from the National Institutes of Health under grant number R01DC03915. The U.S. Government has certain rights in the invention.--

Signed and Sealed this
Twenty-third Day of October, 2012

David J. Kappos
*Director of the United States Patent and Trademark Office*